US012486219B2

(12) United States Patent
Bergeson et al.

(10) Patent No.: US 12,486,219 B2
(45) **Date of Patent: *Dec. 2, 2025**

(54) MODIFIED TETRACYCLINES FOR TREATMENT OF ALCOHOL USE DISORDER, PAIN AND OTHER DISORDERS INVOLVING POTENTIAL INFLAMMATORY PROCESSES

(71) Applicant: Texas Tech University System, Lubbock, TX (US)

(72) Inventors: Susan E. Bergeson, Lubbock, TX (US); Ted W. Reid, Lubbock, TX (US); Mayank Shashtri, Lubbock, TX (US); Peter Syapin, Camarillo, CA (US); Phat Tran, Lubbock, TX (US)

(73) Assignee: Texas Tech University System, Lubbock, TX (US)

( * ) Notice: Subject to any disclaimer, the term of this patent is extended or adjusted under 35 U.S.C. 154(b) by 70 days.

This patent is subject to a terminal disclaimer.

(21) Appl. No.: 17/251,469

(22) PCT Filed: Jun. 13, 2019

(86) PCT No.: PCT/US2019/036928

§ 371 (c)(1),
(2) Date: Dec. 11, 2020

(87) PCT Pub. No.: WO2019/241490

PCT Pub. Date: Dec. 19, 2019

(65) Prior Publication Data

US 2021/0403416 A1 Dec. 30, 2021

Related U.S. Application Data

(60) Provisional application No. 62/684,467, filed on Jun. 13, 2018, provisional application No. 62/684,509, filed on Jun. 13, 2018.

(51) Int. Cl.

| | |
|---|---|
| ***C07C 237/16*** | (2006.01) |
| ***A61B 5/00*** | (2006.01) |
| ***A61K 31/65*** | (2006.01) |
| ***C07C 237/26*** | (2006.01) |
| ***C07D 317/72*** | (2006.01) |

(52) U.S. Cl.
CPC .......... *C07C 237/26* (2013.01); *A61B 5/4848* (2013.01); *A61K 31/65* (2013.01); *C07D 317/72* (2013.01); *C07C 2603/46* (2017.05)

(58) Field of Classification Search
CPC .................................................. C07C 237/16
See application file for complete search history.

(56) References Cited

U.S. PATENT DOCUMENTS

| | | | |
|---|---|---|---|
| 2003/0166585 A1 | 9/2003 | Draper et al. | |
| 2004/0063674 A1 | 4/2004 | Levy et al. | |
| 2005/0048574 A1 | 3/2005 | Kantor et al. | |
| 2007/0093455 A1 | 4/2007 | Abato et al. | |
| 2010/0173991 A1 | 7/2010 | Lorenz et al. | |
| 2014/0155357 A1 | 6/2014 | Abato et al. | |
| 2015/0377894 A1 | 12/2015 | Helson | |
| 2017/0144979 A1* | 5/2017 | Duncan | C07C 323/60 |
| 2022/0040208 A1* | 2/2022 | Bergeson | C07D 317/72 |

FOREIGN PATENT DOCUMENTS

| | | | | |
|---|---|---|---|---|
| EP | 2659887 A1 | 11/2013 | | |
| WO | WO-03005971 A2 * | 1/2003 | | A61K 31/65 |
| WO | 2004006850 A2 | 1/2004 | | |
| WO | 2004064728 A2 | 8/2004 | | |
| WO | 2005/112945 A2 | 12/2005 | | |
| WO | 2009/012741 A1 | 1/2009 | | |

OTHER PUBLICATIONS

Han, H. "Targeted Prodrug Design to Optimize Drug Delivery." AAPS Pharmsci. (2000), vol. 2 (1) article 6, pp. 1-11. (Year: 2000).*

Ettmayer, P., et al. "Lessons Learned from Marketed and Investigational Prodrugs." J. Med. Chem. (2004) 47(10), pp. 2393-2404. (Year: 2004).*

Testa, B. "Prodrug research: futile or fertile?" Biochem. Pharm. (2004) 68, pp. 2097-2106. (Year: 2004).*

American Chemical Society. Chemical Abstract Service. RN 1629023-37-5. Entered into STN: Oct. 16, 2014. (Year: 2014).*

Agrawal, R. G. et al. 2011. 'Minocycline reduces ethanol drinking', Brain, behavior, and immunity, 25 Suppl 1: S165-9.

Agrawal, R. G. et al. 2014. 'Bioinformatics analyses reveal age-specific neuroimmune modulation as a target for treatment of high ethanol drinking', Alcoholism, clinical and experimental research, 38: 428-37.

Bergeson, S. E. et al. 2016. 'Binge Ethanol Consumption Increases Inflammatory Pain Responses and Mechanical and Cold Sensitivity: Tigecycline Treatment Efficacy Shows Sex Differences', Alcoholism, clinical and experimental research, 40: 2506-15.

Bergeson, S. E. et al. 2016. 'Tigecycline Reduces Ethanol Intake in Dependent and Nondependent Male and Female C57BL/6J Mice', Alcoholism, clinical and experimental research, 40: 2491-98.

(Continued)

*Primary Examiner* — John S Kenyon
(74) *Attorney, Agent, or Firm* — Edwin S. Flores; Daniel J. Chalker; Chalker Flores, LLP

(57) ABSTRACT

The present invention includes novel molecules and methods for using the same to treat Alcohol Use Disorder (AUD), Substance Use Disorder (SUD), tobacco use, pain, or proinflammatory disorders comprising: identifying a subject in need of treatment for at least one of AUD, SUD, pain, or a proinflammatory disorder; and providing the subject with an effective amount of a modified minocycline to ameliorate or eliminate the AUD, SUD, pain, or proinflammatory disorder and that has reduced, or no, antimicrobial activity, wherein the modified tetracycline has a formula, e.g., or the modified doxycycline, minocycline, and tigecycline and their tautomerized structures, where the R-groups shown in the minocycline example above could be different combination of halogen, acetyl ester, methyl ester, and diacetal.

18 Claims, 30 Drawing Sheets

(56) References Cited

OTHER PUBLICATIONS

Blednov, Y. A. et al. 2011. 'Activation of inflammatory signaling by lipopolysaccharide produces a prolonged increase of voluntary alcohol intake in mice', Brain, behavior, and immunity, 25 Suppl 1: S92-S105.
Craig, RG et al., A chemically modified tetracycline inhibits streptozotocin-induced diabetic depression of skin collagen synthesis and steady-state type I procollagen mRNA, Biochimica et Biophysica Acta (3), pp. 250-260, 1998.
Griffin, MO et al., Tetracyclines: a pleitropic family of compounds with promising therapeutic properties. Review of the literature, American Journal of Physiology Cell Physiology 299(3), pp. 1-24 (pp. C539-C548), 2010.
International Search Report and Written Opinion PCT/US2019/036928 dated Aug. 27, 2019.
Lew, MA et al., Antifungal Activity of Four Tetracycline Analogues against Candida albicans in Vitro: Potentiation by Amphotericin B, The Journal of Infectious Diseases, vol. 136, Issue 2, pp. 263-270, 1977.
Liu, Yet al., A Chemically Modified Tetracycline (CMT-3) Is a New Antifungal Agent, Antimicrobial Agents and Chemotherapy vol. 46, No. 5, pp. 1447-1454, 2002.
Martinez, J. M. et al. 2016. 'Effective Reduction of Acute Ethanol Withdrawal by the Tetracycline Derivative, Tigecycline, in Female and Male DBA/2J Mice', Alcoholism, clinical and experimental research, 40: 2499-505.
Montesinos, J. et al. 2016. 'Impact of the Innate Immune Response in the Actions of Ethanol on the Central Nervous System', Alcoholism, clinical and experimental research, 40: 2260-70.
Rhodes, J. S. et al. 2005. 'Evaluation of a simple model of ethanol drinking to intoxication in C57BL/6J mice', Physiology & Behavior, 84: 53-63.
Schedlbauer, A., T. et al. 2015. 'Structural characterization of an alternative mode of tigecycline binding to the bacterial ribosome', Antimicrobial agents and chemotherapy, 59: 2849-54.
Syapin, P. J. et al. 2016. 'Effective Reduction in High Ethanol Drinking by Semisynthetic Tetracycline Derivatives', Alcoholism, clinical and experimental research, 40: 2482-90.
Craig, R.G. et al. "A chemically modified tetracycline inhibits streptozotocin-induceddiabetic depression of skin collagen synthesis and steady-state type I procollagen mRNA." Biochim BioRhY.S Acta. Apr. 24, 1998; 1402(3):250-60.
Griffin, Michael O. et al. "Tetracyclines: a pleitropic family of compounds with promising therapeutic properties. Review of the literature", Am J Physiol Cell Physiol. Sep. 2010; 299(3): C539-C548.
Hutchinson, Mark R. et al. "Minocycline suppresses morphine-induced respiratory depression, suppresses morphine-induced reward, and enhances systemic morphine-induced analgesia", Brain, Behavior and Immunity 22(8): 1248-1256, 2009.
International Search Report [ISA/US] PCT/US2019/036892 dated Sep. 17, 2019.
International Search Report [ISA/US] PCT/US2019/036928 dated Aug. 27, 2019.
Lew, Michael A. et al. "Antifungal Activity of Four Tetracycline Analogues against Candida albicans in Vitro: Potentiation by Amphotericin B" The Journal of Infectious Diseases, vol. 136, Issue 2, Aug. 1977, pp. 263-270.
Liy, Yu et al. "A Chemically Modified Tetracycline (CMT-3) Is a New Antifungal Agent" Antimicrobial Agents and Chemotherapy, May 2002, p. 1447-1454.
Schedlbauer, A. et al. 2015. "Structural characterization of an alternative mode of tigecycline binding to the bacterial ribosome", Antimicrobial agents and chemotherapy, 59: 2849-54.

* cited by examiner

A. CMM1-2

MODIFIED TETRACYCLINES FOR TREATMENT OF ALCOHOL USE DISORDER, PAIN AND OTHER DISORDERS INVOLVING POTENTIAL INFLAMMATORY PROCESSES

CROSS-REFERENCE TO RELATED APPLICATIONS

This application claims priority to and is the National Stage of International Application No. PCT/US2019/036928, filed on Jun. 13, 2019 and claims priority to U.S. Provisional Application Ser. No. 62/684,467, filed Jun. 13, 2018, and U.S. Provisional Application Ser. No. 62/684,509, filed Jun. 13, 2018, the entire contents of which are incorporated herein by reference.

STATEMENT OF FEDERALLY FUNDED RESEARCH

This invention was made with government support under NIH AA021142 awarded by the National Institute of Alcohol Abuse and Alcoholism (NIAAA). The government has certain rights in the invention.

TECHNICAL FIELD OF THE INVENTION

The present invention relates in general to the field of novel tetracycline derivatives with reduced antimicrobial activity for use in treating disorders of the central nervous system.

BACKGROUND OF THE INVENTION

Without limiting the scope of the invention, its background is described in connection with modified tetracyclines.

Alcohol use disorder (AUD) or alcoholism is a condition that affects roughly 5% of individuals worldwide. AUD is characterized by an increased tolerance to alcohol and a physical dependence on alcohol making it hard for an individual to control intake. Some of the long-term effects of ingesting ethanol include cognitive and psychological changes, liver cirrhosis, gastritis, cardiomyopathy, anemia, and certain types of cancers. Alcoholism is caused by a complex mixture of genetic and environmental factors. There have been several genes linked to the way people metabolize alcohol and the development of AUD. The availability of alcohol also contributed to the number of people with AUD. Alcohol is the most available and widely abused recreational drug with beer being the third-most popular drink behind water and tea. There are currently very few methods for treating alcoholism outside of rehabilitation therapy which can be costly and very public. There is an unsatisfied need for a pharmaceutical component that is able to help combat the debilitating effects of AUD.

One such modified tetracycline derivative is taught in U.S. Patent Publication No. 20100173991, filed by Lorenz, et al., and entitled "Method for the synthesis of A-ring aromatized acetyl minocyclines". Briefly, these applicants are said to teach a less complex method for the production of A-ring aromatized acetyl minocyclines of the formula:

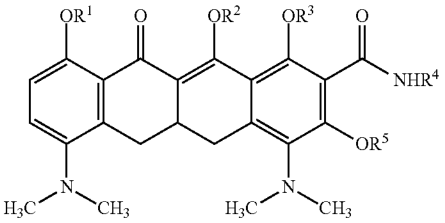

wherein R1 to R5 are acetyl and/or H, in which minocycline hydrochloride is reacted with acetic anhydride in the presence of a proton catcher and the reaction product is subjected to chromatographic filtration using a carrier material and an eluant. The eluant is distilled off, and the product is subsequently cleaned by recrystallization. However, this application is silent on the treatment of dependency disorders and only teaches the treatment of neurodegeneration.

Another such modified tetracycline derivative is taught in Patent Publication No. WO2009012741, also filed by Lorenz, et al., entitled "Method for the synthesis of A-ring aromatized acetyl minocyclines". The application is said to teach a method for the production of A-ring aromatized acetyl minocyclines that is less complex. The method for the production of A-ring aromatized acetyl minocyclines of the formula (I), wherein R1 to R5=acetyl and/or H is achieved when minocycline hydrochloride is reacted with acetic anhydride in the presence of a proton catcher, the reaction product is subjected to chromatographic filtration using a carrier material and an eluant. The eluant is then distilled off, and the product is subsequently cleaned by recrystallization. Like the application described hereinabove, this application is also silent on the treatment of dependency disorders and only teaches the treatment of neurodegeneration.

However, a need remains for novel molecules for the treatment of alcohol consumption, including, but not limited to high drinking levels, withdrawal symptoms and increased sensitization and duration of pain, and alter innate immune responses and reduce tobacco consumption and all aspects of the addiction process of other drugs subject to abuse, including opioids (Mark R. Hutchinson, Alexis L. Northcutt, Lindsey W. Chao, Jeffrey J. Kearney, Yingning Zhang, Debra L. Berkelhammer, Lisa C. Loram, Robert R. Rozeske, Sondra T. Bland, Steven F. Maier, Todd T. Gleeson, and Linda R. Watkins, Minocycline suppresses morphine-induced respiratory depression, suppresses morphine-induced reward, and enhances systemic morphine-induced analgesia, Brain, Behavior and Immunity 22(8): 1248-1256, 2009).

SUMMARY OF THE INVENTION

In another embodiment, the present invention includes a modified tetracycline molecule, pharmaceutically acceptable salts, pro-drugs, biologically active metabolites, and tautomers thereof of formulas 1 to 85:

1.
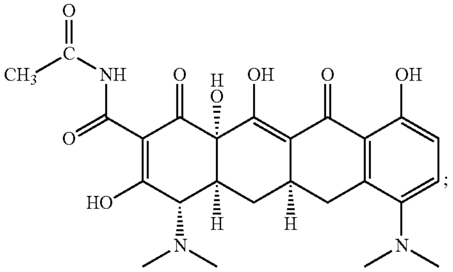
2.
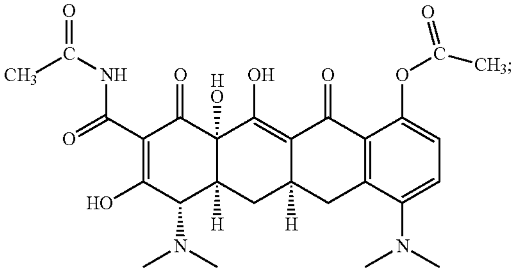
3.
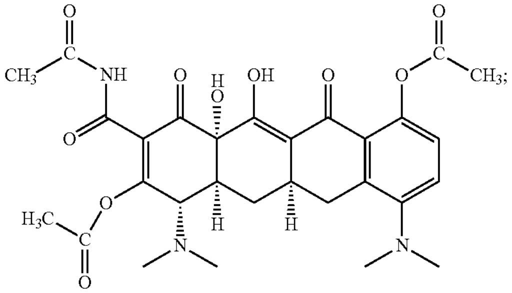
4.
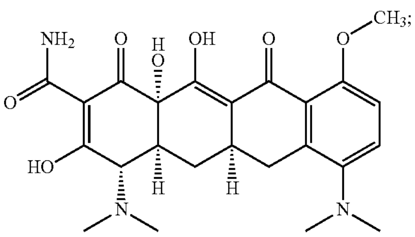
5.
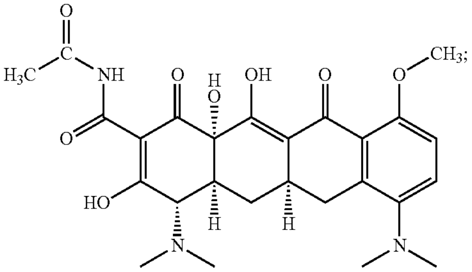
-continued
6.
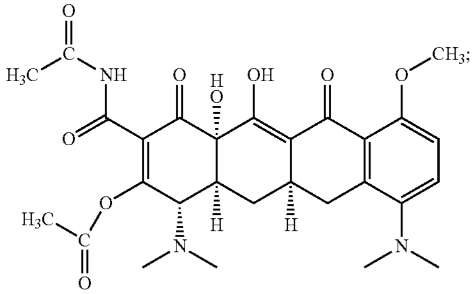
7.
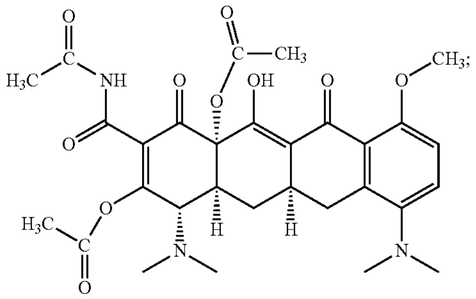
8.
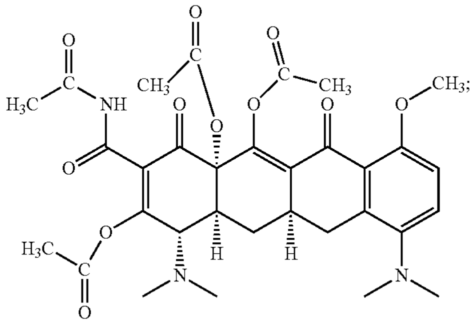
9.
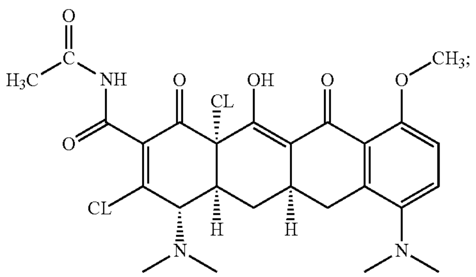
10.
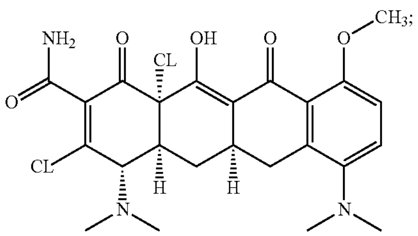

-continued
11.
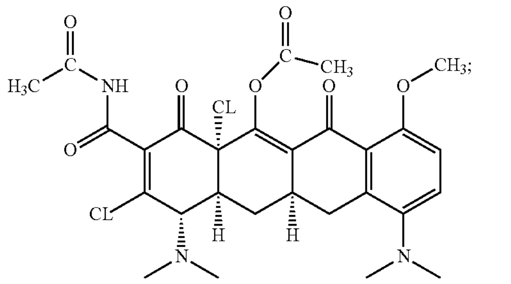
12.
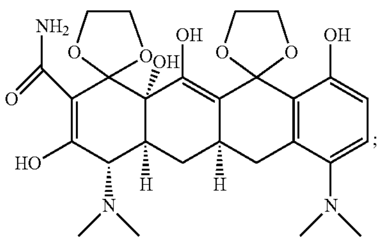
13.
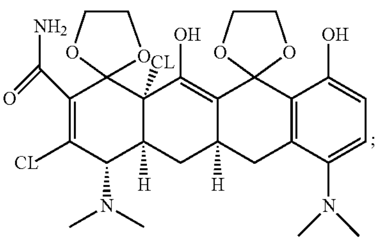
14.
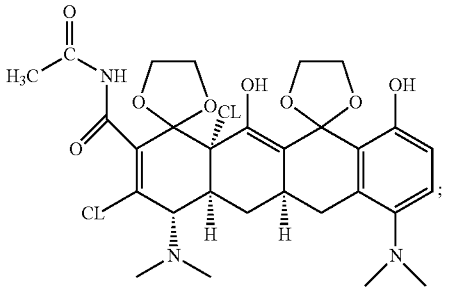
15.
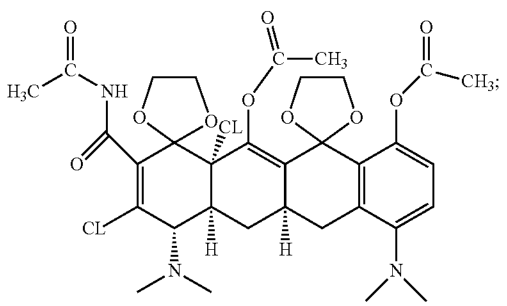
-continued
16.
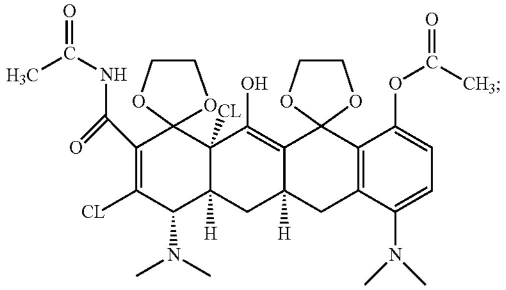
17.
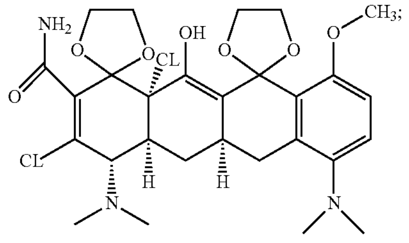
18.
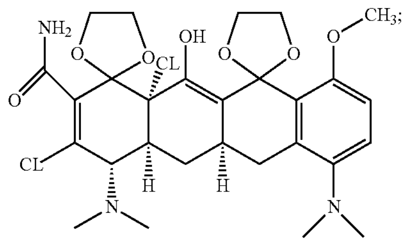
19.
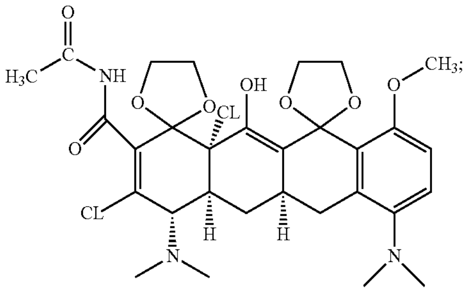
20.
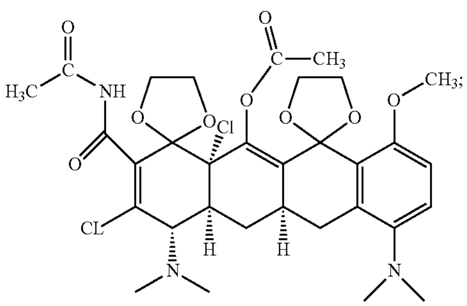

-continued
21.
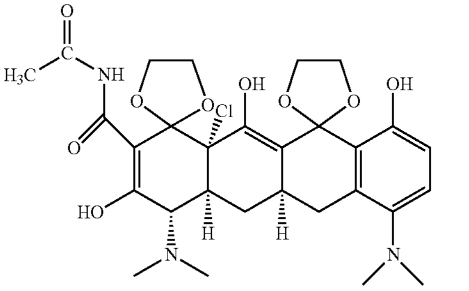
22.
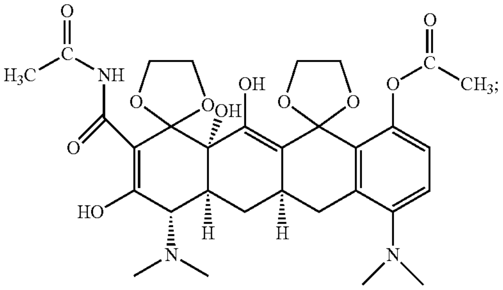
23.
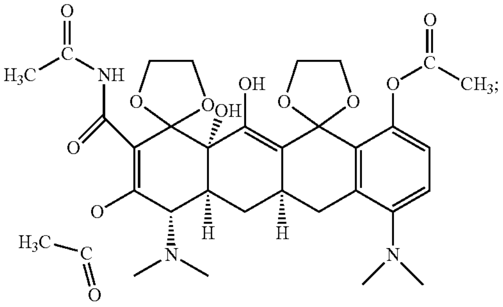
24.
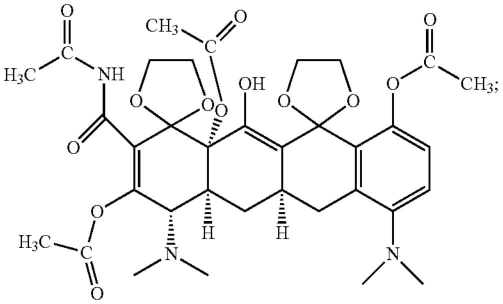
25.
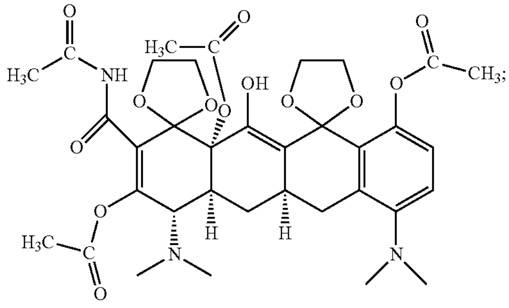
-continued
26.
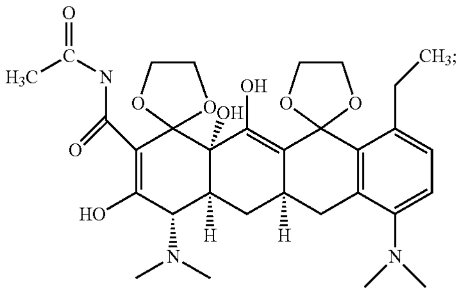
27.
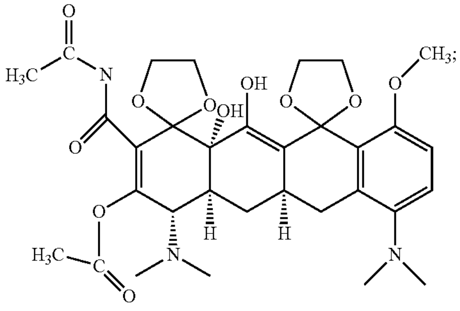
28.
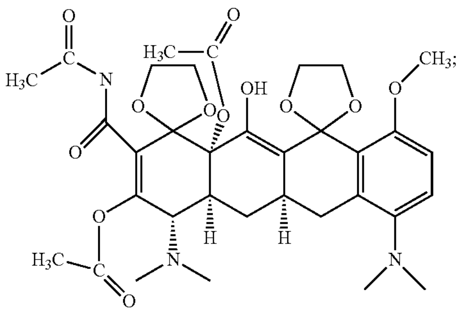
29.
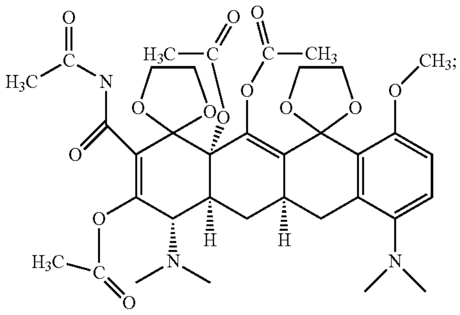
30.
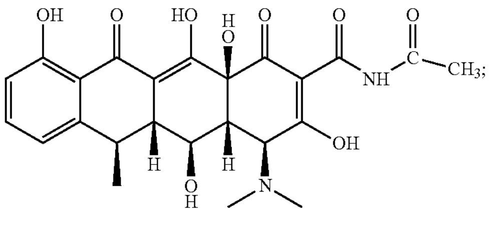

-continued
31.
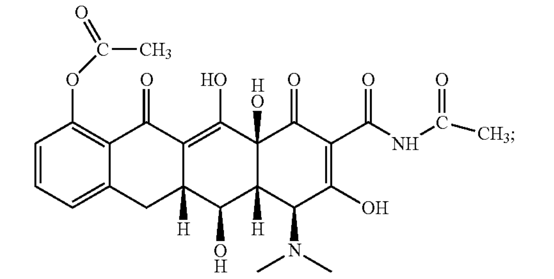
32.
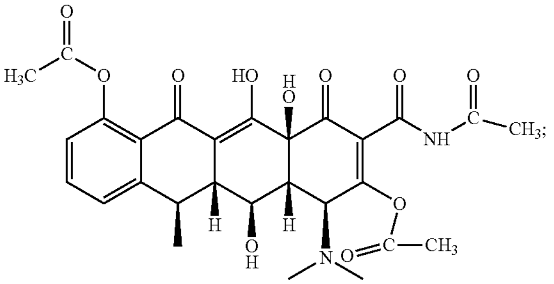
33.
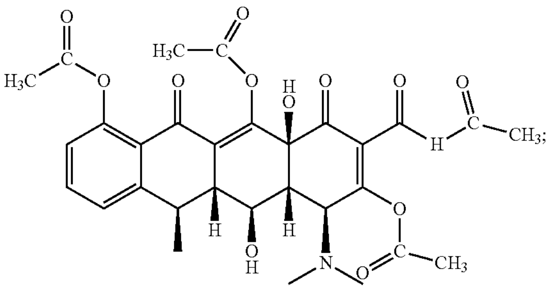
34.
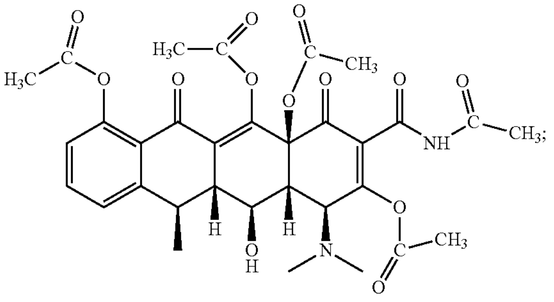
35.
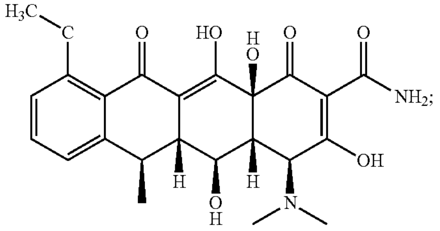
-continued
36.
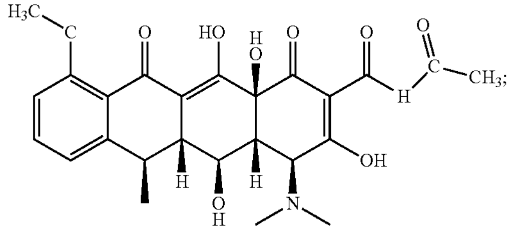
37.
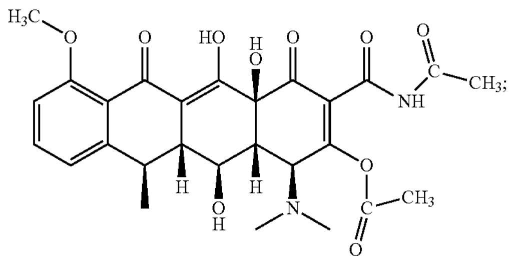
38.
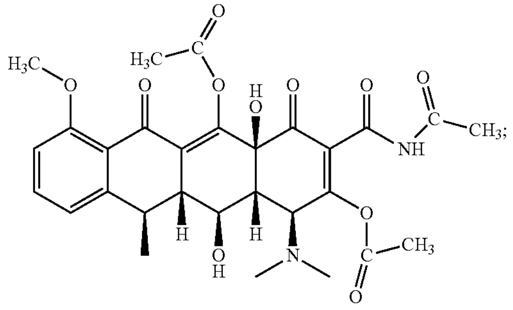
39.
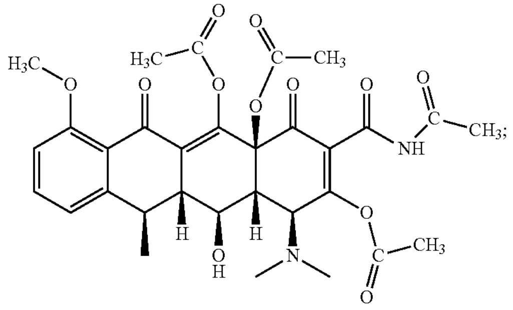
40.
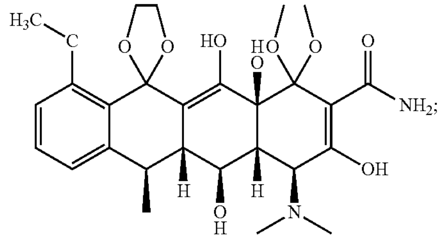

-continued
41.
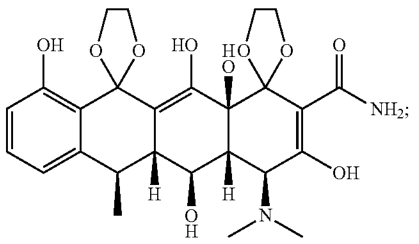
42.
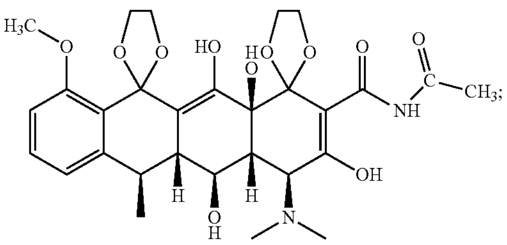
43.
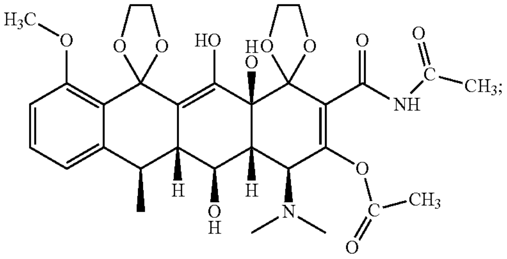
44.
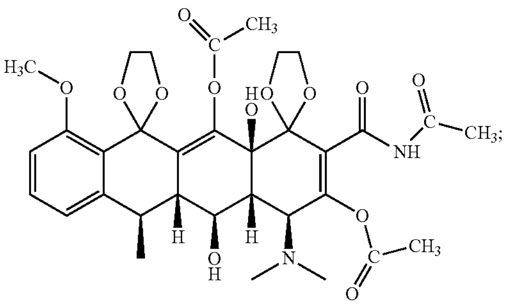
45.
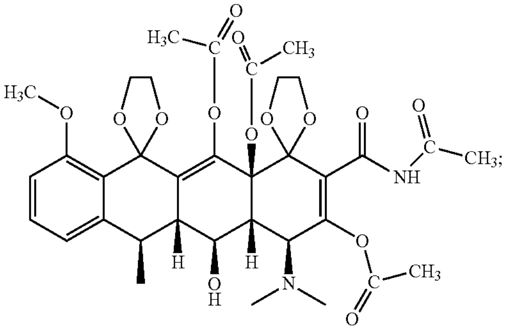
-continued
46.
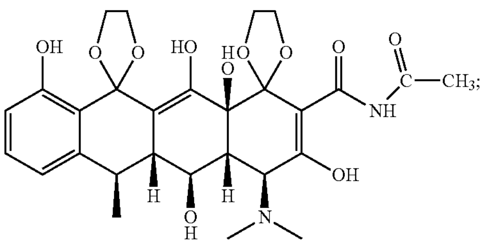
47.
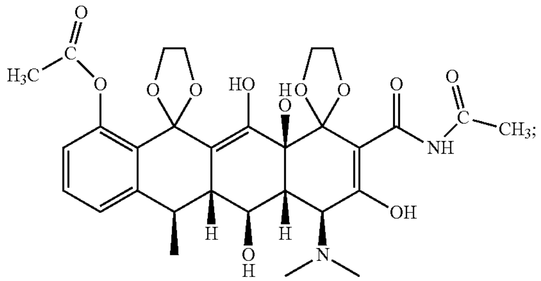
48.
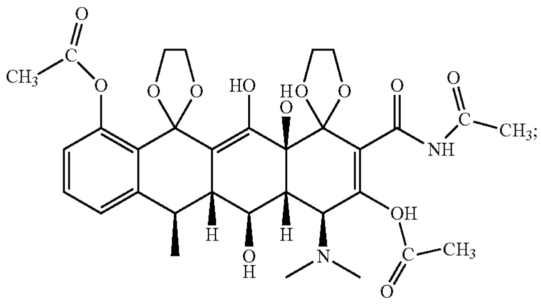
49.
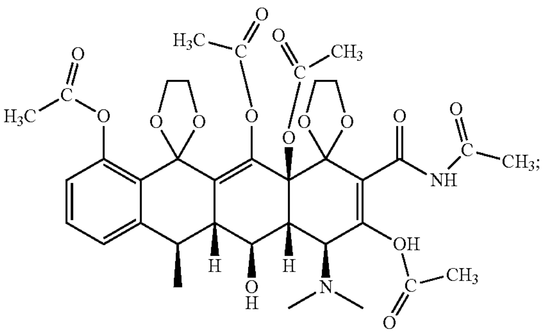
50.
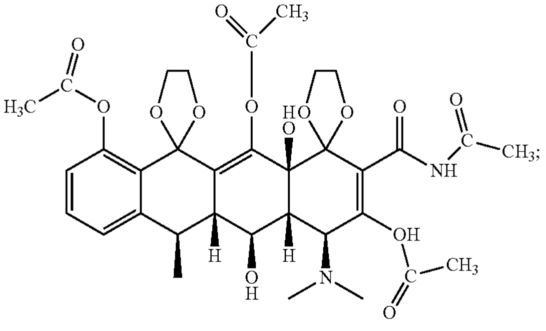

-continued
51.
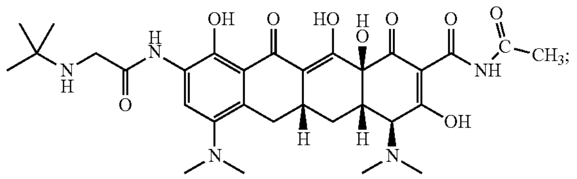
52.
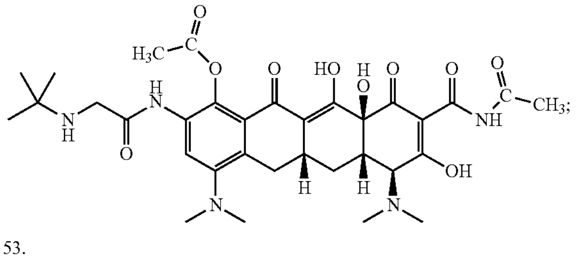
53.
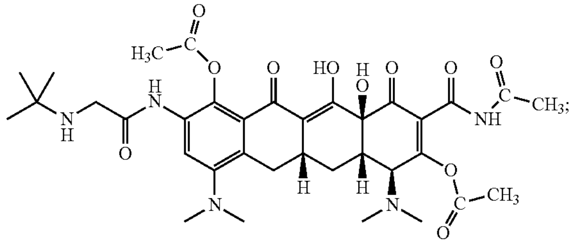
54.
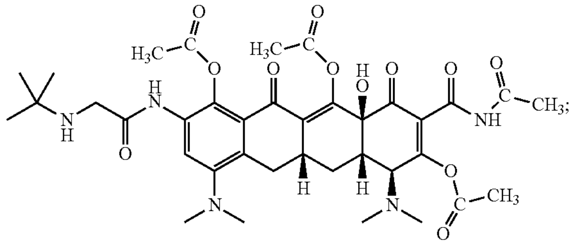
55.
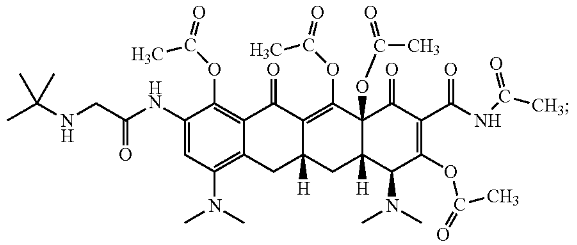
56.
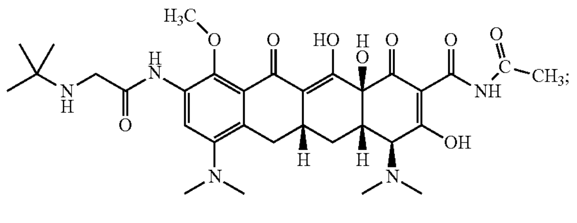
-continued
57.
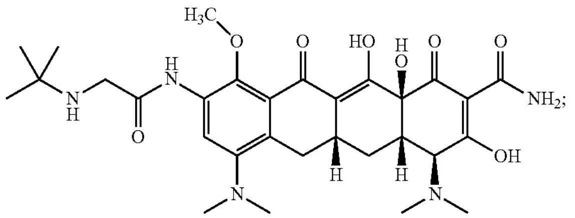
58.
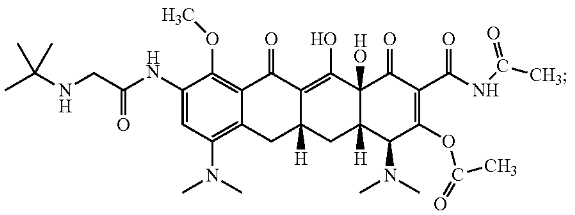
59.
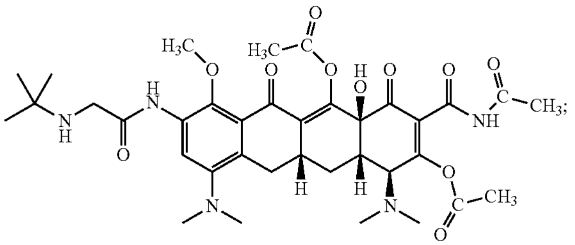
60.
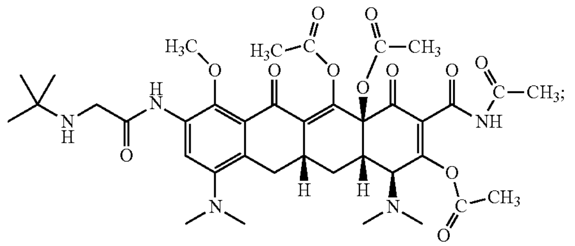
61.
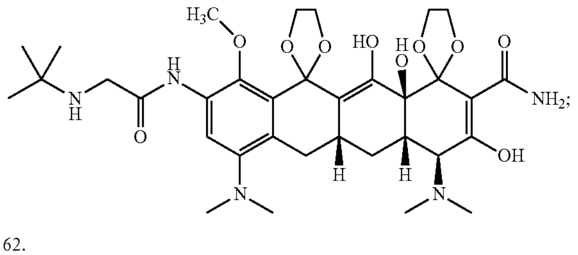
62.
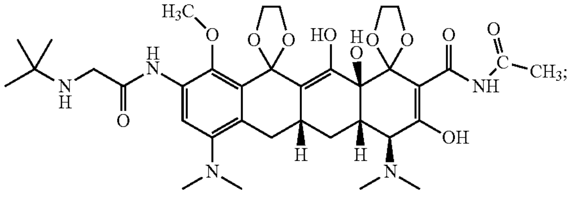

-continued
63.
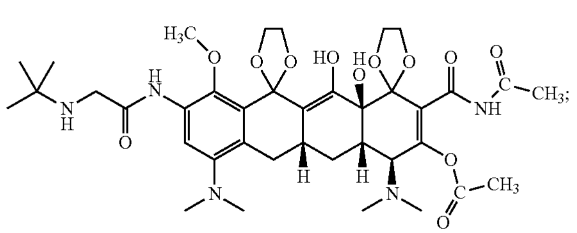
64.
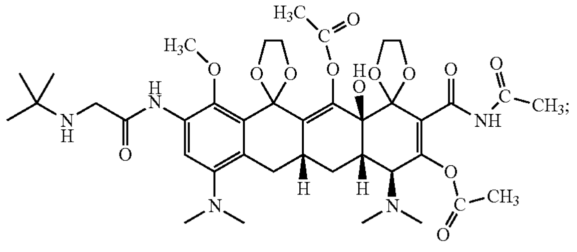
65.
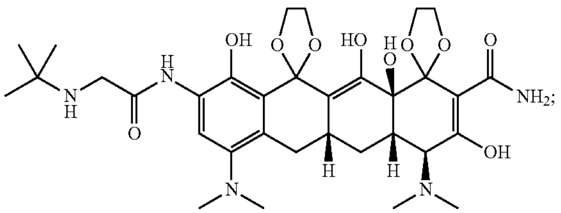
66.
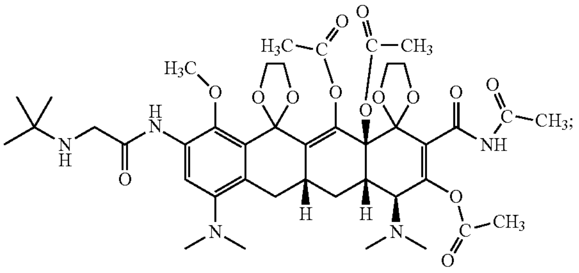
67.
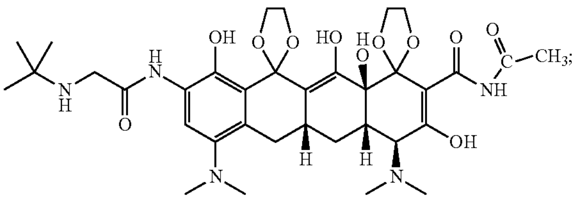
68.
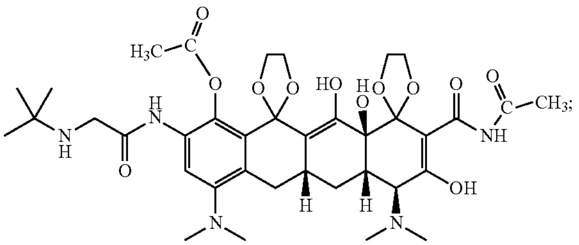
-continued
69.
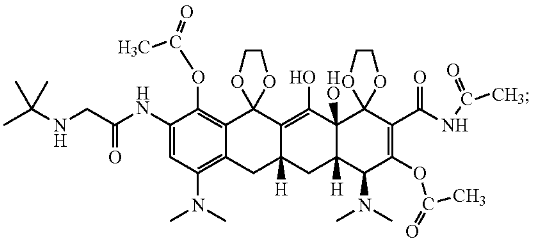
or
70.
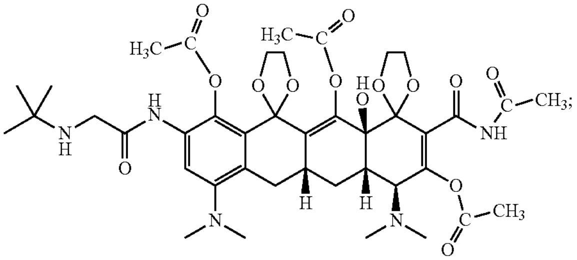
71.
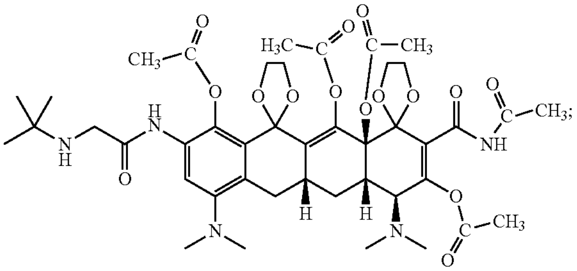
72.
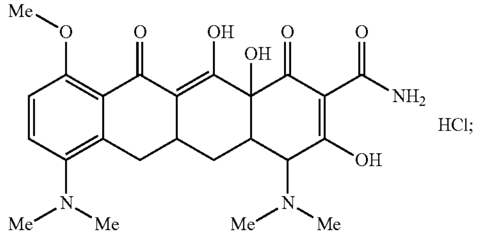
73.
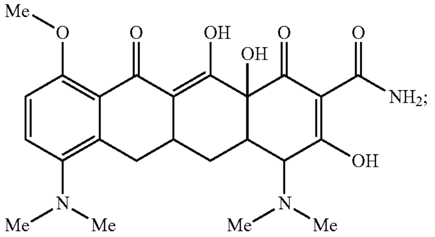
74.
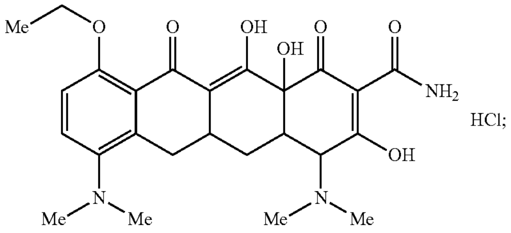

-continued

75.

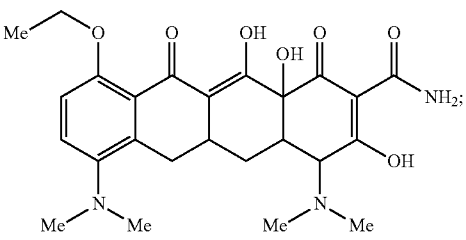

76.

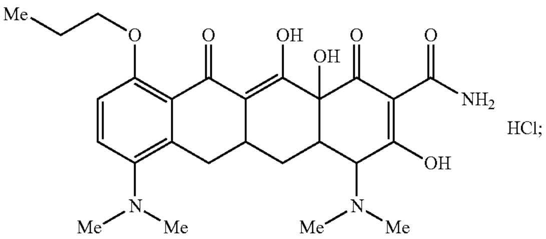

77.

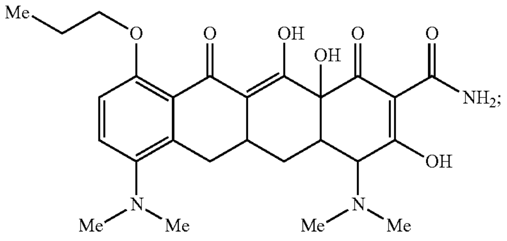

78.

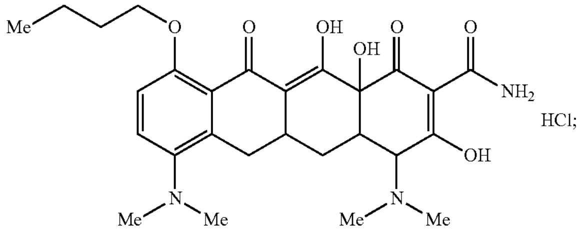

79.

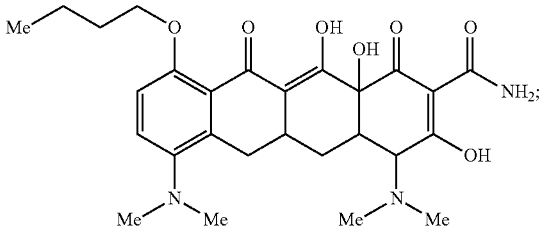

80.

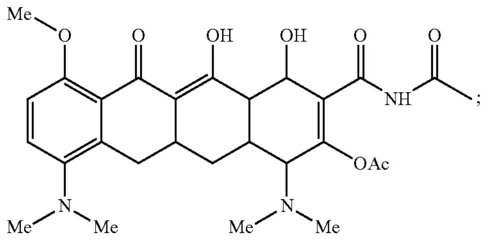

-continued

81.

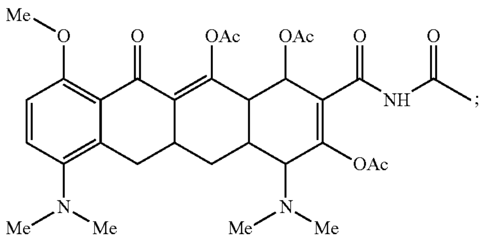

82.

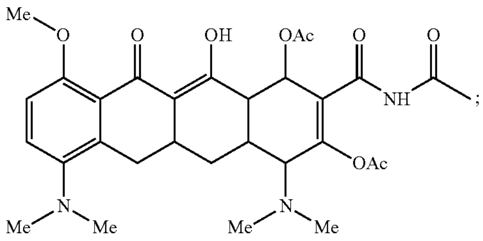

83.

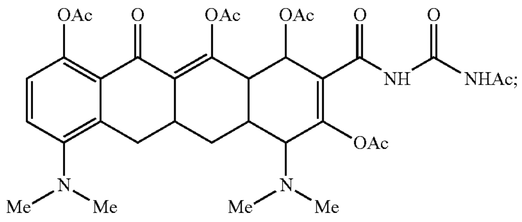

84.

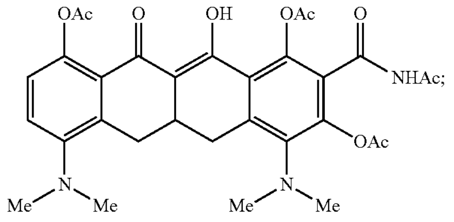

or

85.

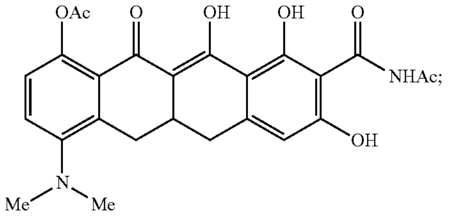

wherein the doxycycline, minocycline, and tigecycline structures are modified to prevent binding of the molecule to a ribosome. In one aspect, the molecule has reduced or substantially no antibacterial activity. In another aspect, the molecule has reduced or substantially no antifungal activity. In another aspect, the molecule is provided in an amount that inhibits Alcohol Use Disorder (AUD), Substance Use Disorder (SUD, tobacco use, pain and disorders involving potential inflammatory processes. In another aspect, the ribosome is a bacterial ribosome. In another aspect, the modification at least one of: produces steric hindrance, blocks hydrogen bonding, or change coordination with divalent cations. In another aspect, the molecule further comprises pharmaceutically acceptable buffer, excipient, filler, or carrier. In another aspect, the molecule is formulated administration orally, enterally, intramuscularly, parenterally, intravenously, or intraperitoneally.

In another embodiment, the present invention includes a pharmaceutical composition comprising a compound of Formula 1 to 85, pharmaceutically acceptable salts, prodrugs, biologically active metabolites, and tautomers thereof.

In another embodiment, the present invention includes a method of treating Alcohol Use Disorder (AUD), Substance Use Disorder (SUD, tobacco use, pain, or proinflammatory disorders comprising: providing the subject with an effective amount of one or more modified tetracyclines of Formula 1 to 85 to ameliorate or eliminate the AUD, SUD, pain, or proinflammatory disorder and that reduced, or no, antimicrobial activity. In one aspect, the molecule has reduced or substantially no antibacterial activity. In another aspect, the molecule has reduced or substantially no antifungal activity. In another aspect, the molecule inhibits Alcohol Use Disorder (AUD), Substance Use Disorder (SUD, pain and disorders involving potential inflammatory processes. In another aspect, the modified molecule is a doxycycline, minocycline, or tigecycline or their tautomeric structures. In another aspect, the ribosome is a bacterial ribosome. In another aspect, the modification at least one of: produces steric hindrance, blocks hydrogen bonding, or change coordination with divalent cations. In another aspect, the molecule further comprises pharmaceutically acceptable buffer, excipient, filler, or carrier. In another aspect, the molecule is formulated administration orally, enterally, intramuscularly, parenterally, intravenously, or intraperitoneally.

In another embodiment, the present invention includes a method of treating Alcohol Use Disorder (AUD), Substance Use Disorder (SUD, tobacco use, pain, or proinflammatory disorders comprising: identifying a subject in need of treatment for at least one of AUD, SUD, pain, or a proinflammatory disorder; and providing the subject with an effective amount of one or more modified tetracyclines of Formula 1 to 85 to ameliorate or eliminate the AUD, SUD, pain, or proinflammatory disorder and that reduced, or no, antimicrobial activity. In another aspect, the molecule has reduced or substantially no antibacterial activity. In another aspect, the molecule has reduced or substantially no antifungal activity. In another aspect, the molecule inhibits Alcohol Use Disorder (AUD), Substance Use Disorder (SUD, pain and disorders involving potential inflammatory processes. In another aspect, the modified molecule is a doxycycline, minocycline, or tigecycline or their tautomeric structures. In another aspect, the ribosome is a bacterial ribosome. In another aspect, the modification at least one of: produces steric hindrance, blocks hydrogen bonding, or change coordination with divalent cations. In another aspect, the molecule further comprises pharmaceutically acceptable buffer, excipient, filler, or carrier. In another aspect, the molecule is formulated administration orally, enterally, intramuscularly, parenterally, intravenously, or intraperitoneally.

In another embodiment, the present invention includes a method of evaluating a candidate drug believed to be useful in treating Alcohol Use Disorder (AUD), Substance Use Disorder (SUD, including for opioids, tobacco use, pain, or proinflammatory disorders, the method comprising: a) measuring the Alcohol Use Disorder (AUD), Substance Use Disorder (SUD, tobacco use, pain, or proinflammatory disorders from a set of patients; b) administering a candidate drug to a first subset of the patients, and a placebo to a second subset of the patients, wherein the candidate drug is a modified doxycycline, minocycline, tigecycline and their tautomeric structures that have different combinations of halogen, acetyl ester, methyl ester, and diacetal having formula 1 to 85; c) repeating step a) after the administration of the candidate drug or the placebo; and d) determining if the candidate drug reduces the Alcohol Use Disorder (AUD), Substance Use Disorder (SUD, pain, or proinflammatory disorders that is statistically significant as compared to any reduction occurring in the second subset of patients, wherein a statistically significant reduction indicates that the candidate drug is useful in treating Alcohol Use Disorder (AUD), Substance Use Disorder (SUD, tobacco use, pain, or proinflammatory disorders. In another aspect, the molecules have moderate to no antibacterial activity. In another aspect, the molecules have moderate to no antifungal activity. In another aspect, the molecules inhibit Alcohol Use Disorder (AUD), Substance Use Disorder (SUD, pain and disorders involving potential inflammatory processes. In another aspect, the modified molecules is a doxycycline, minocycline, or tigecycline or their tautomeric structures. In another aspect, the ribosome is a bacterial ribosome. In another aspect, the modification at least one of: produces steric hindrance, blocks hydrogen bonding, or change coordination with divalent cations.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

Figure 1:
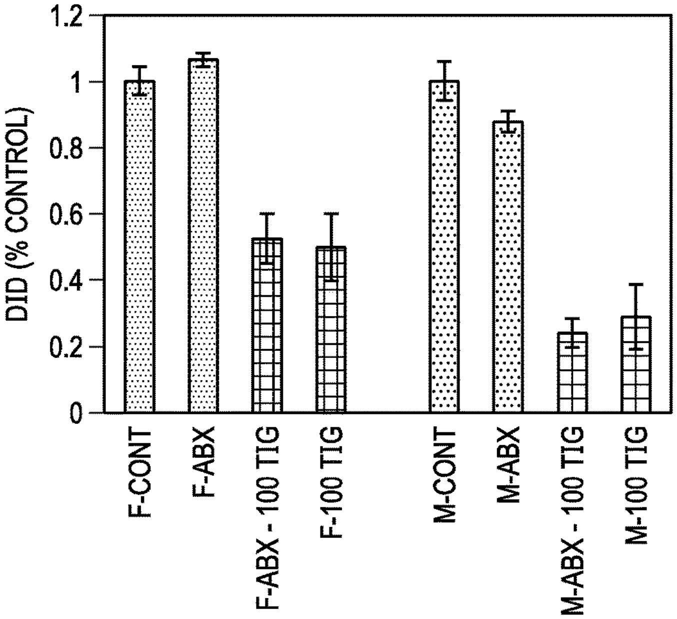
FIG. 1 is a graph that shows "sterilization" of the GI microbiome had no apparent effect on DID ethanol consumption or efficacy of tigecycline to reduce drinking.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not limit the invention, except as outlined in the claims.

The present invention is directed to modification of tetracyclines with R6'=H, such as doxycycline, minocycline and tigecycline, by acetylation or other modification such that the molecule loses most, or all, of its antibacterial properties, yet retain the ability to reduce negative traits related to alcohol consumption, including, but not limited to high drinking levels, withdrawal symptoms and increased sensitization and duration of pain, and reduce tobacco consumption. In addition, the novel molecules can also be used to treat disorders that have an innate immune component. The invention involves any tetracycline that does not bind to its site of action in a bacterium. The modification of tetracyclines at R6' in which R6' is not H, may act by different mechanisms, such as, steric hindrance, stereo chemistry, lack of hydrogen binding, transport into the bacteria, etc., however, the modification must allow it to still retain its ability to reduce high drinking levels, withdrawal symptoms and increased sensitization and duration of pain, and reduce tobacco consumption.

Only three pharmacotherapeutic treatments for Alcohol Use Disorder (AUD) are FDA approved and none are widely used (<10% of AUD patients) or show a strong effect to reduce risky- or dependence-based drinking in the long-term (<20% see sustained decreased drinking outcomes). Unfortunately, approximately 10% of the US population suffers from AUD and over 5% of all medical morbidities share risky ethanol consumption as an underlying issue. As a consequence, intoxication, in general, and 'alcohol addiction' (severe AUD), in particular, are important clinical problems. Given the limited pharmacotherapeutic choice, there is a compelling need for continued development of new treatments across the AUD spectrum (mild to severe DSM-V classification). In fact, improved treatments targeting high alcohol consumption and withdrawal-related symptoms are desirable as precipitating withdrawal can be a medical emergency with risk for death. To date, drugs targeting drinking do not protect against withdrawal, and drugs used to reduce withdrawal symptoms are often co-addictive with alcohol.

The present inventors recently showed that tetracycline analogs were preclinically efficacious to reduce high alcohol consumption, withdrawal symptoms and alcohol-mediated pain sensitization and now have exciting preliminary data showing efficacy for an improved chemically modified minocycline (CMM) (Bergeson, Blanton, et al. 2016; Martinez et al. 2016; Bergeson, Nipper, et al. 2016; Syapin, Martinez, Curtis, Marquardt, Allison, Groot, Baby, Al-Hasan, Segura, et al. 2016). Further, the inventors have previously found tetracycline analogs, including doxycycline, minocycline, and tigecycline to be efficacious against various aspects of Alcohol Use Disorder (AUD), including cessation of drinking, withdrawal symptoms and sensitization and increased duration of pain (Bergeson, Blanton, et al. 2016; Martinez et al. 2016; Bergeson, Nipper, et al. 2016; Syapin, Martinez, Curtis, Marquardt, Allison, Groot, Baby, Al-Hasan, Segura-Ulate, et al. 2016; Agrawal et al. 2014; Agrawal et al. 2011). However, despite these encouraging results, the present inventors have found that the effect of these tetracyclines was through a central nervous system (CNS) function and not mediated in any part by changes in resident bacteria; see FIGS. 1 and 2. The data shown are key to understanding that the tetracyclines could be modified to remove the antibiotic property and still remain useful for AUD treatment. Other literature suggests that alcohol effects may be mediated, at least in part, by bacteria or their components (Blednov et al. 2011); for a recent review, see (Montesinos, Alfonso-Loeches, and Guerri 2016). However, despite this controversy in the literature, the present invention is the first to show that the action of the known CMMs does not require antibiotic properties.

fied to lose its bacterial ribosome binding component. Removal of anti-microbial properties should reduce side effects and avoid increased drug resistance.

TABLE 1

Tetracycline derivative structures

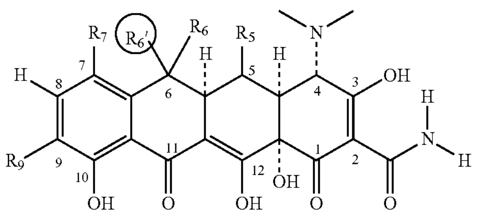

| Drug Name | R5 | R6 | R6' | R7 | R9 | LogD | LogP |
|---|---|---|---|---|---|---|---|
| Tetracycline | H | $CH_3$ | OH | H | H | −3.55 | −1.47 |
| Oxytetracycline | OH | $CH_3$ | OH | H | H | −4.25 | −1.5 |
| Chlortetracycline | H | $CH_3$ | OH | Cl | H | −2.43 | 0.33 |
| Demeclocycline | H | H | OH | Cl | H | −3.40 | −1.07 |
| Doxycycline* | OH | $CH_3$ | H | H | H | −3.29 | −0.54 |
| Minocycline* | H | H | H | $N(CH_3)_2$ | H | −2.25 | 0.20 |
| Tigecycline* | H | H | H | $N(CH_3)_2$ | $NHCOCH_2NHC(CH_3)_3$ | −2.73 | −1.30 |

*Semi-synthetic tetracycline?

FIG. 1 is a graph that shows that "sterilization" of the GI microbiome had no apparent effect on DID ethanol consumption or efficacy of tigecycline to reduce drinking Given the ability of the gut microbiome to change behavior, the present inventors determined whether tigecycline, a broad spectrum antibiotic, might work through modulation of the gut bacterial flora. A ten-day "sterilization" treatment with ampicillin, neomycin, metronidozale and vancomycin was used. Bedding was changed daily to avoid repopulation. DID was started on day 11 after one day of no metronidazole. Tigecycline was given at 100 mg/kg intraperitoneal (i.p.) n=7, mean±SEM. No significant difference was found for either DID alone or tigecycline treatment suggesting no role for microbiota signaling in alcohol consumption or tigecycline efficacy.

Figure 2:
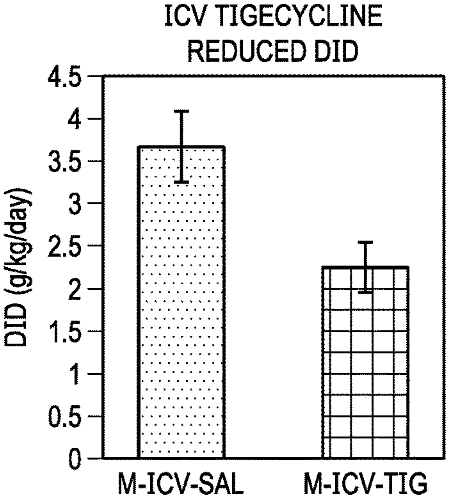
FIG. 2 is a graph that shows intracerebroventricular (ICV) Tigecycline reduced DID consumption.

FIG. 2 is a graph that shows that intracerebroventricular (ICV) Tigecycline reduced DID consumption. To test the hypothesis that tigecycline works at the level of the CNS, rather than the PNS, 3 ul of drug (9 mg/ml) was given icy 20 hrs prior to DID testing. n=9-11, mean±SEM, **$p<0.01$. The results suggest that tigecycline acts via the CNS to reduce alcohol consumption.

Thus, the present inventors recognized for the first time that the mechanism of action of the CMM for use in Alcohol Use Disorder, pain and other disorders involving potential inflammatory processes does not involve tetracycline's general antibiotic properties. Thus, the present inventors tested several tetracyclines to determine structural or functional components that contributed to the AUD treatment efficacy. As shown in Table 1, it appears that the C6' hydrogen is, at least in part necessary to convey the positive action on AUD-related traits, but not those known to bind to the A-site of the bacterial ribosome (Schedlbauer et al. 2015).

Figure 6A:
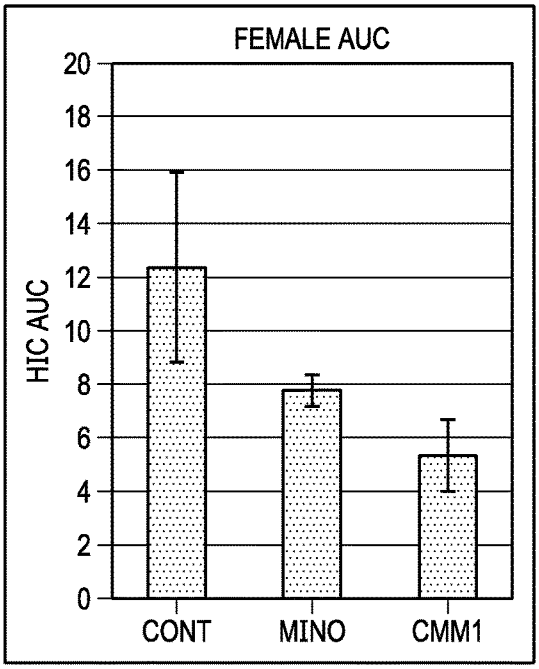
FIGS. 6A and 6B are graphs that show that acetylated minocycline, CMM1, reduced alcohol withdrawal symptoms. Female (FIG. 6A) and male (FIG. 6B) DBA/2J mice were tested with CMM1, 100 mg/kg p.o., at 2 hrs following 4 g/kg 20% ethanol in saline.
Figure 6B:
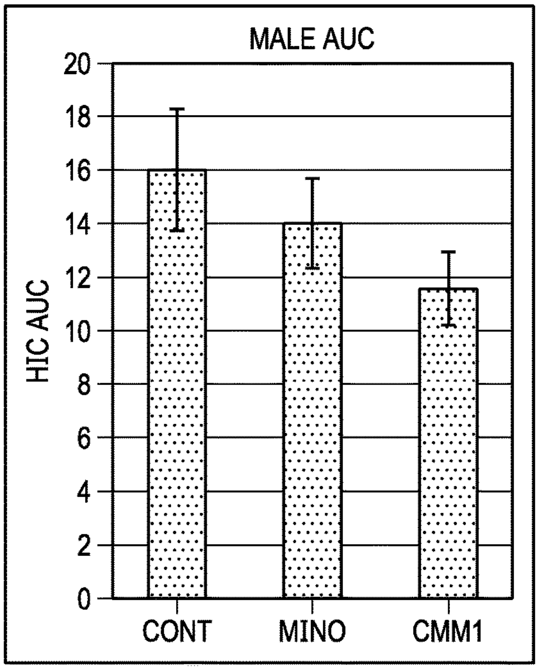
Figure 7:
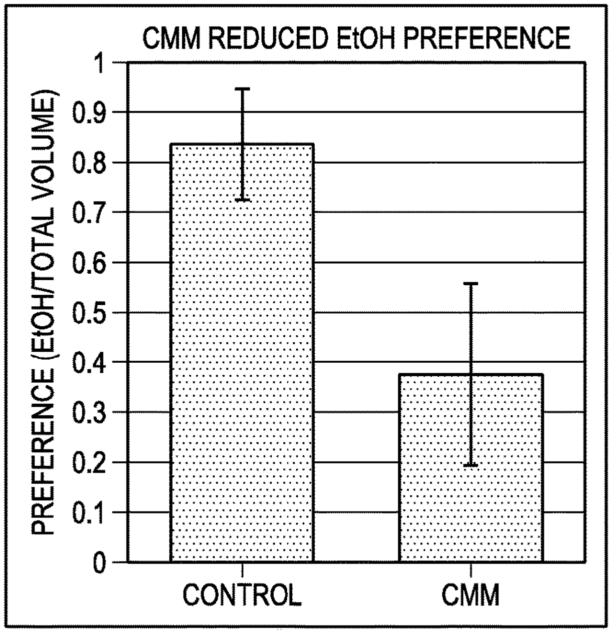
FIG. 7 is a graph that shows that CMM1 reduced alcohol consumption and preference in swine.

Table 1. Of seven tetracyclines tested against AUD traits (Syapin, Martinez, Curtis, Marquardt, Allison, Groot, Baby, Al-Hasan, Segura-Ulate, et al. 2016) only doxycycline, minocycline and tigecycline were effective. Shown in grey highlight is that the R6' group is the only difference between the effective and non-effective tetracycline drugs, and together with our unpublished data in FIGS. 1 and 2, indicated that the structure of the molecule could be modi- Next, the inventors modified minocycline by acetylation (FIG. 3) and determined its loss of antibiotic properties, see FIGS. 4A and 4B. In addition, the inventors tested the CMM1 compound in mice using the Drinking In the Dark model (Rhodes et al. 2005) to show that the ability to reduce alcohol consumption was retained (FIGS. 5A to 5D). Ability to reduce alcohol withdrawal symptoms was detected and is shown in FIGS. 6A and 6B. Finally, efficacy of 10 mg/kg per os (p.o.) to reduce high drinking was confirmed in swine (FIG. 7).

Figure 8A:
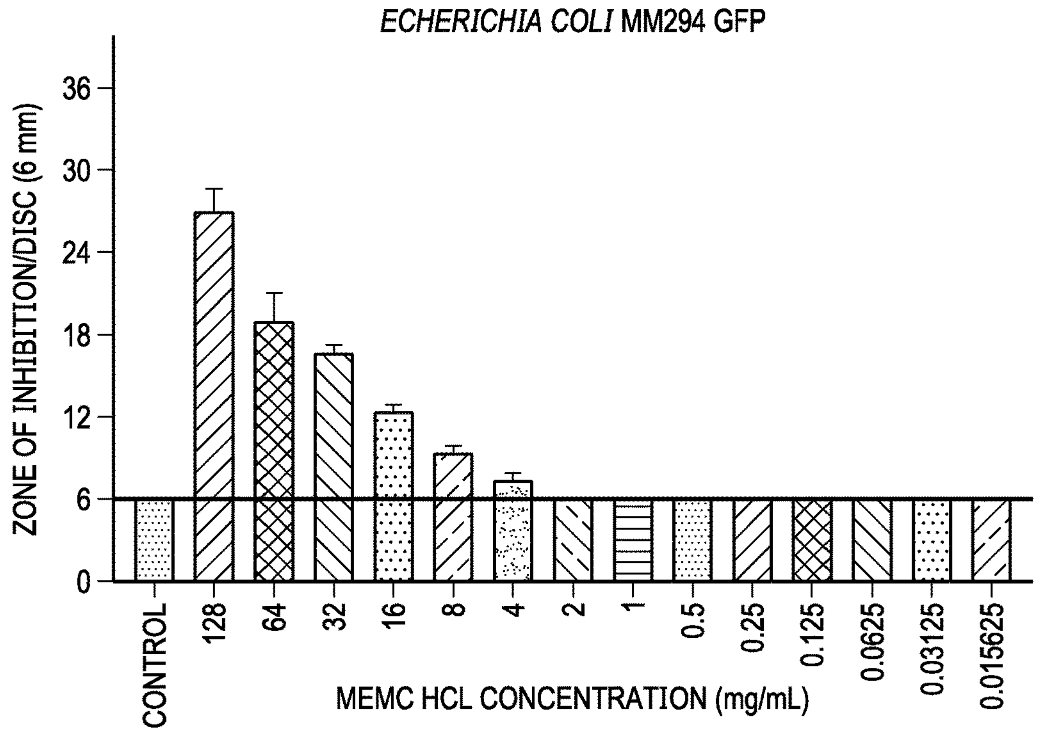
FIGS. 8A to 8C show the activity of Methyl Ether Minocycline (4,7-Bis-dimethylamino-3,12,12a-trihydroxy-10-methoxy-1,11-dioxo-1,4,4a,5,5a,6,11,12a-octahydro-naphthacene-2-carboxylic acid amide, Hydrochloride), as shown with FIG. 8A *E coli* MM294 GFP zone of inhibition, FIG. 8B *E coli* MM294 GFP CFU/disc, and FIG. 8C reduction of binge ethanol consumption.
Figure 8B:
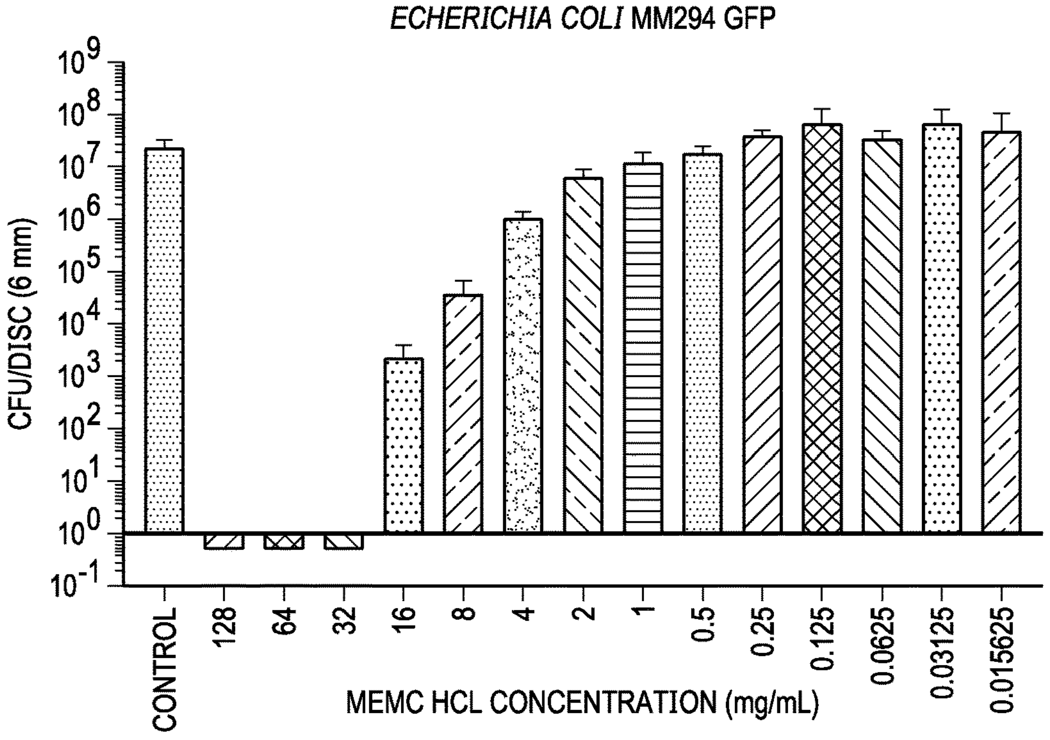

These initial findings with acetylation of minocycline can be expanded to further substitutions at the various positions (R1 to R5) following the teachings of the present invention. Briefly, the process taught herein is an example of modifications that change the affinity of tetracycline analogs to bind the bacterial ribosome. Thus, any such modification could include changes to produce steric hindrance, block hydrogen bonding, change coordination with divalent cations, or any other means to change affinity for ribosomal binding. FIGS. 8A-B includes a list of molecules for use with the present invention.

Figure 3:
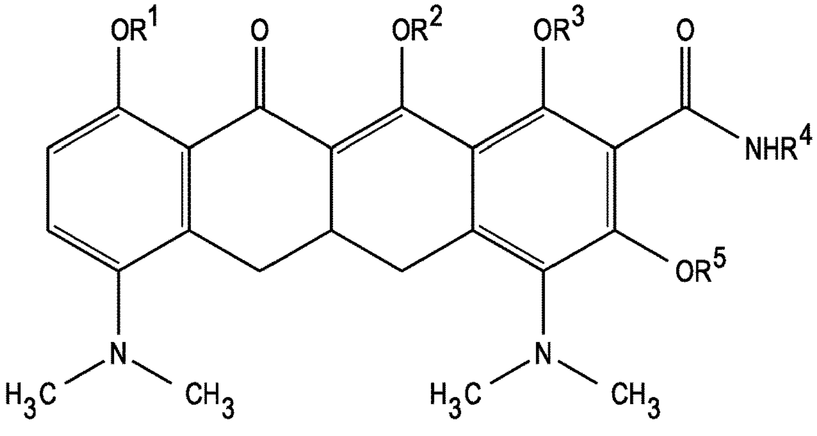
FIG. 3 shows the structures of acetylated CMM1 and CMM2, in which all R=acetate for CMM1, and for CMM2 all R=acetate, except R4=H.

FIG. 3 shows the structures of acetylated CMM1 and CMM2, in which all R=acetate for CMM1, and for CMM2 all R=acetate, except R4=H.

Figure 4A:
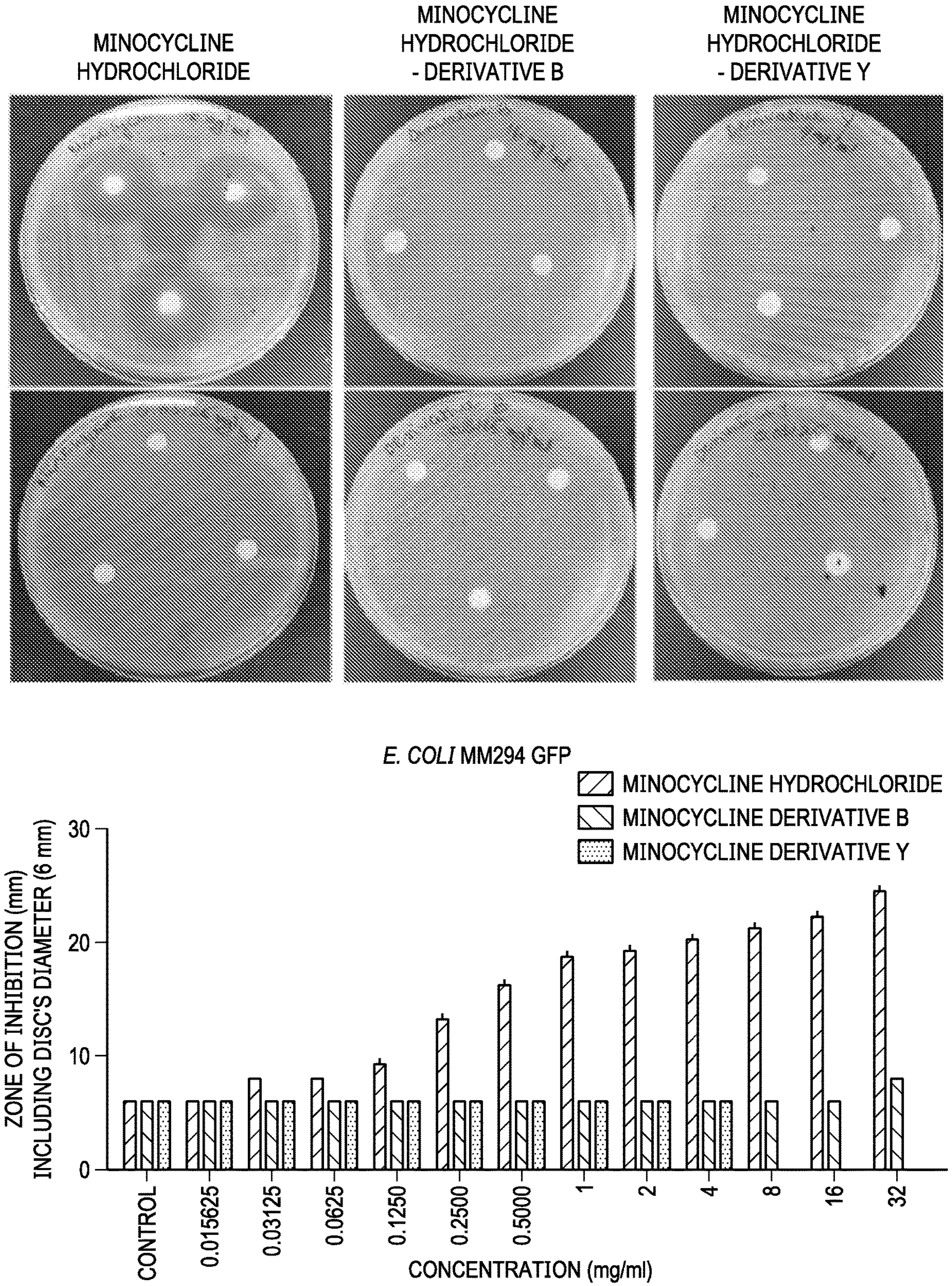
FIGS. 4A and 4B show that Minocycline acetate derivatives eliminated *E. coli* bactericidal action.
Figure 4B:
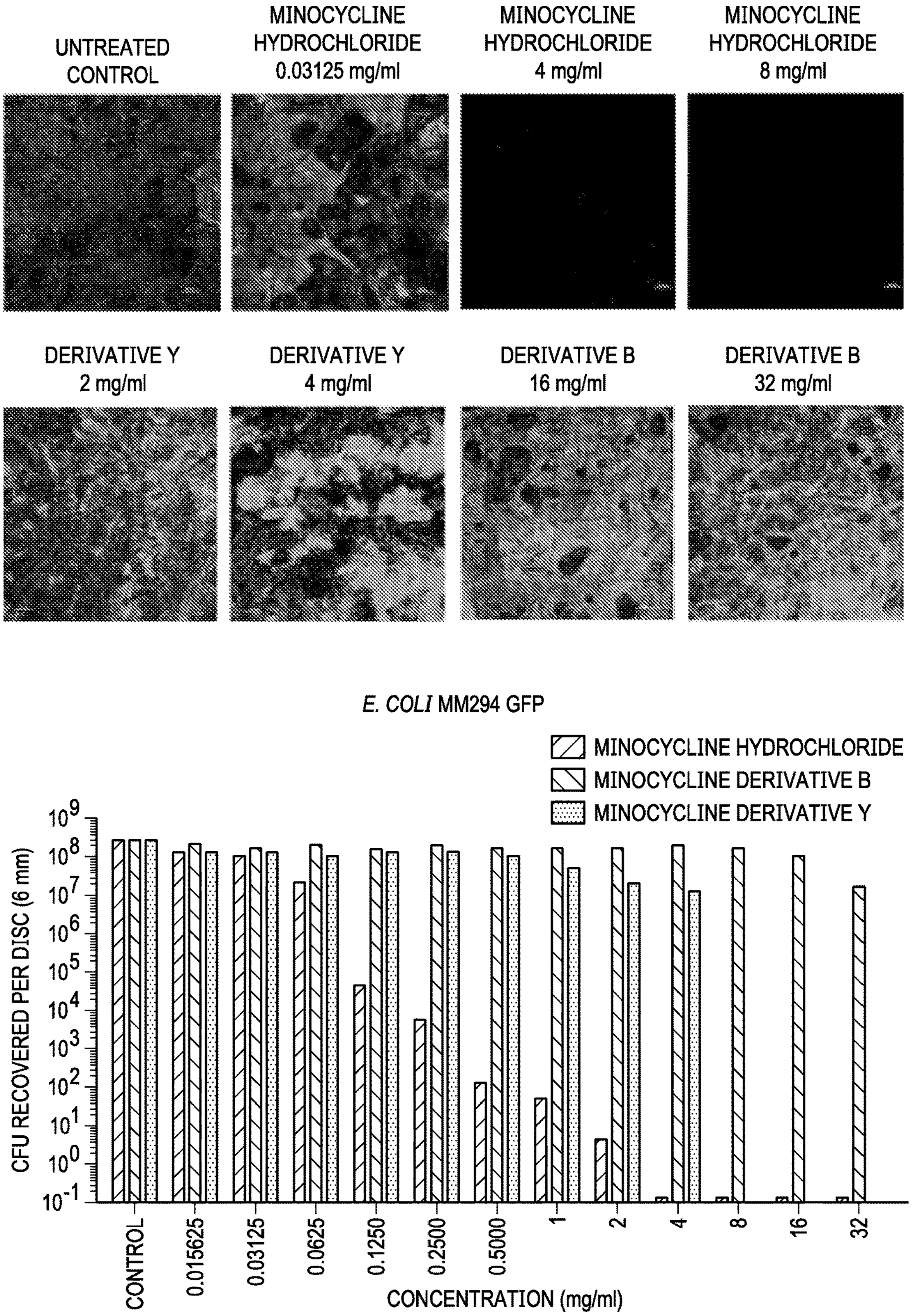
Figure 5A:
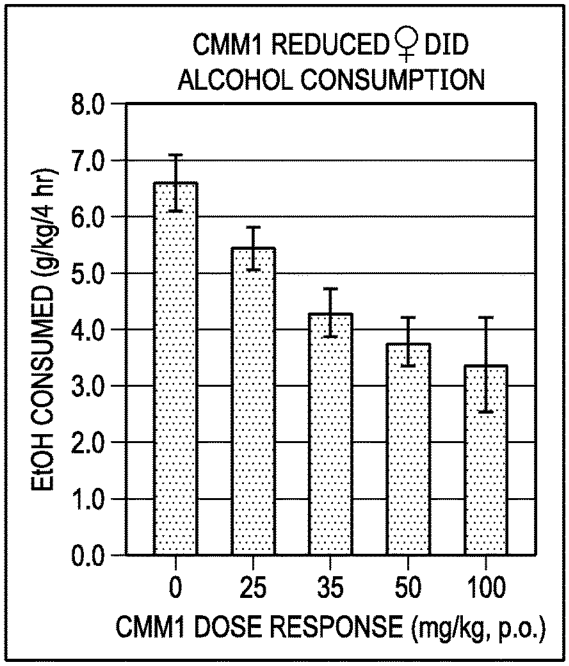
FIGS. 5A to 5D shows the results from using CMM1-Acetylated minocycline derivative reduced ethanol consumption.
Figure 5B:
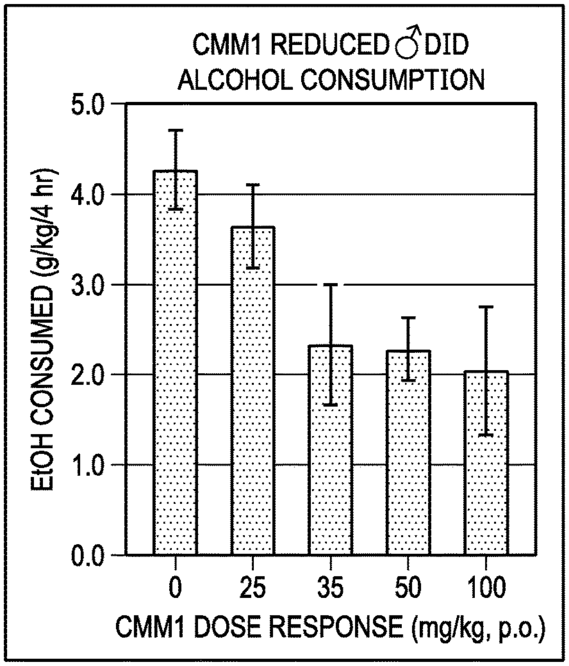
Figure 5C:
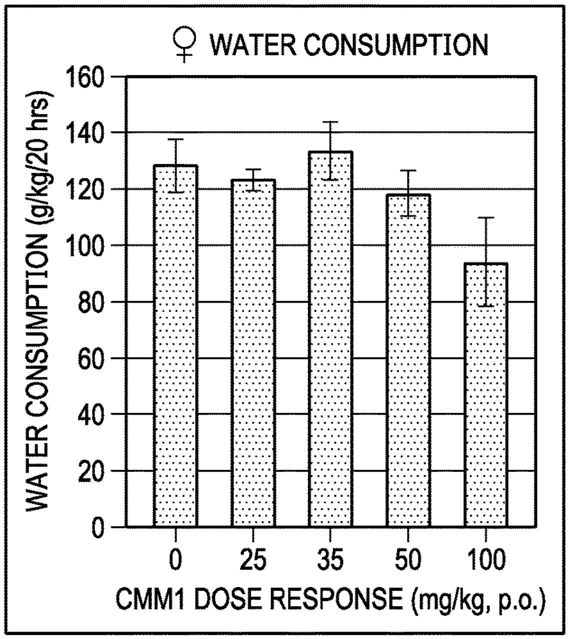
Figure 5D:
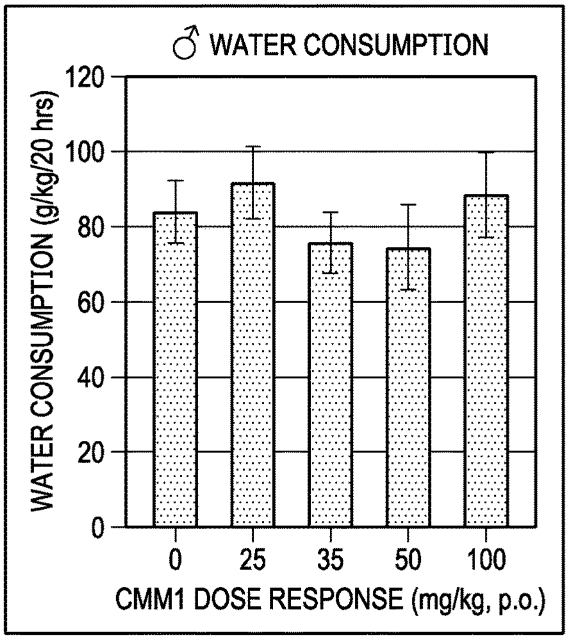

FIGS. 4A and 4B show that Minocycline acetate derivatives eliminated *E. coli* bactericidal action. Minocycline and two acetylated derivatives, CMM1 (B) and CMM2 (Y), were tested in a dose response manner for A) zone of inhibition (ZOI) and B) recovered colony forming units (CFU) per disk. Data indicate a loss of antibiotic activity even at high doses.

FIGS. 5A to 5D are graphs that show that CMM1-Acetylated minocycline derivative reduced ethanol consumption. Using a standard Drinking In the Dark (DID) murine model of binge drinking, we tested the effect of 0, 25, 35, 50 and 100 mg/kg per os (p.o.) acetylated minocycline (derivative Y, or CMM1) vs control. As shown above, the derivative significantly reduced drinking (n=4/group, p=0.004). These results show that acetylated minocycline, CMM1, reduced alcohol consumption in a dose-dependent response.

FIGS. 6A and 6B are graphs that show that acetylated minocycline, CMM1, reduced alcohol withdrawal symptoms. Female and male DBA/2J mice were tested with CMM1, 100 mg/kg per p.o., at 2 hrs following 4 g/kg 20% ethanol in saline. Shown are the Handling Induced Convulsion scores, background subtracted and summed over 24 hours. CMM1 was more effective in females, and reduced onset, peak and duration of withdrawal symptoms. Note, that CMM1 was more effective than the parent drug, minocycline. Mean±SEM, n=5/group.

FIG. 7 is a graph that shows that CMM1 reduced alcohol consumption and preference in swine. Large White x Landrace hybrid swine were given a water vs 5% ethanol in a two-bucket choice. Total ethanol consumption and alcohol preference was reduced by CMM1. Mean±SEM, n=3/group.

The compounds of the present invention have the following formulas, and include pharmaceutically acceptable salts, pro-drugs, biologically active metabolites, and tautomers thereof:

1.

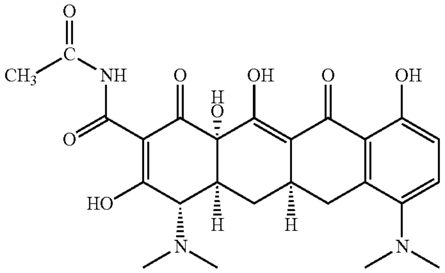

2.

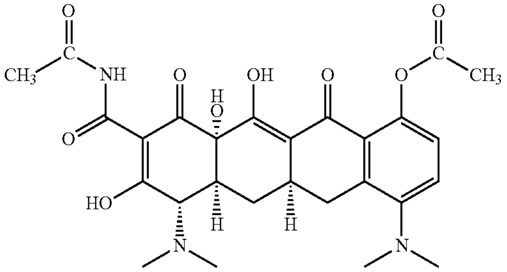

3.

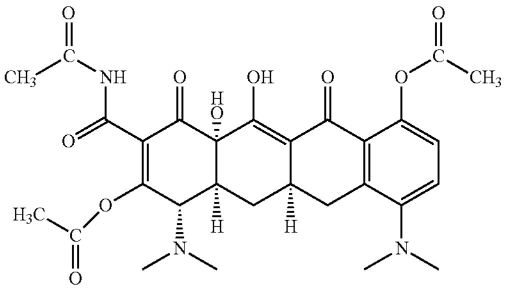

4.

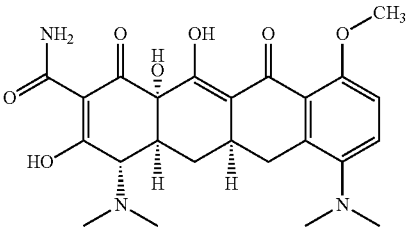

-continued

5.

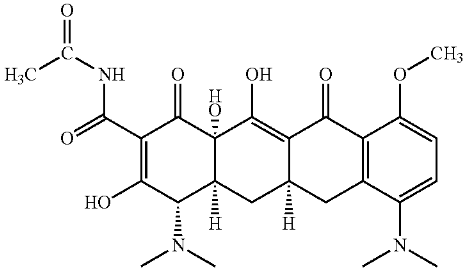

6.

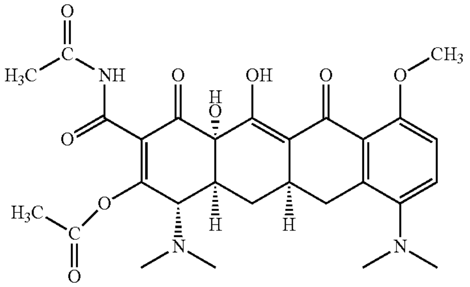

7.

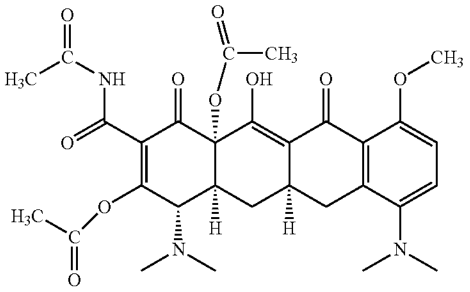

8.

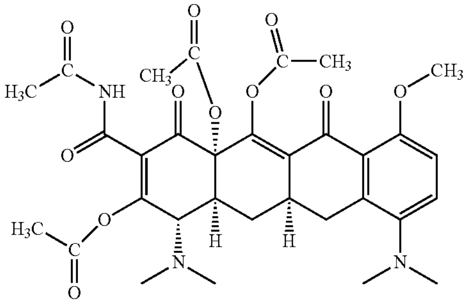

9.

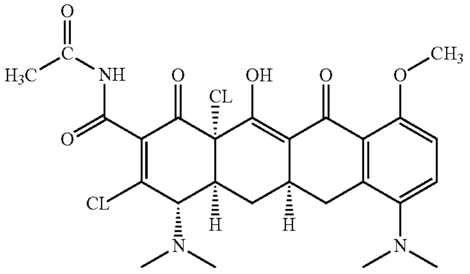

-continued
10.
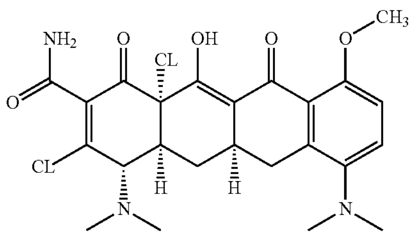
11.
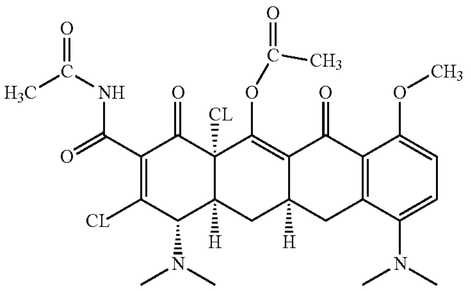
12.
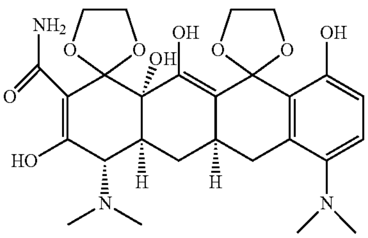
13.
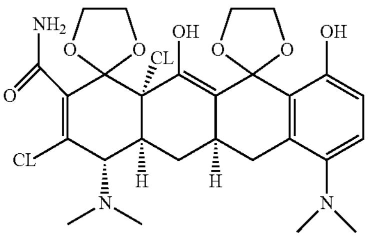
14.
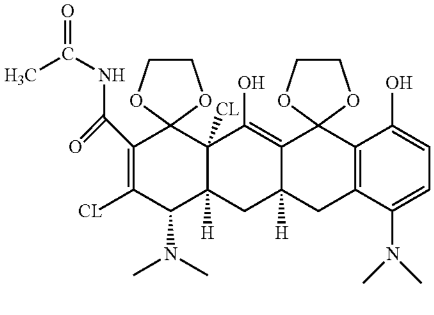
-continued
15.
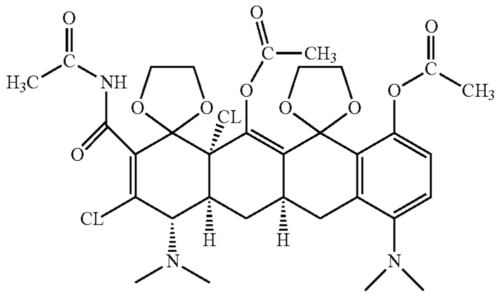
16.
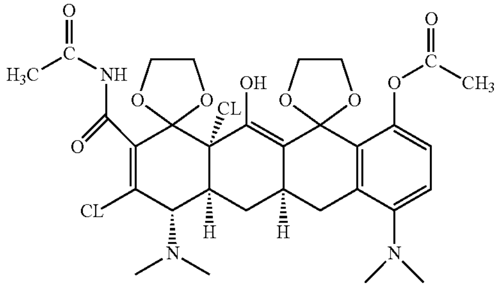
17.
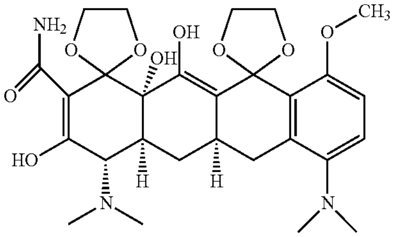
18.
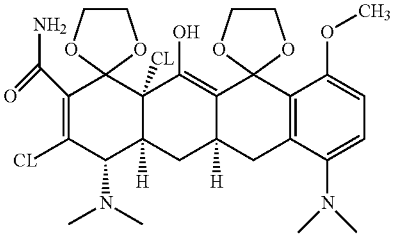
19.
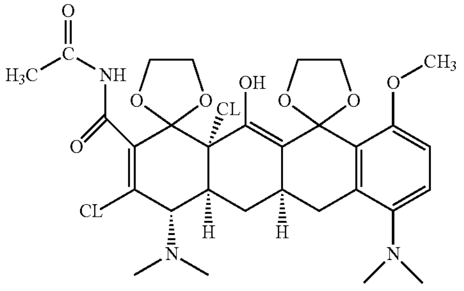

-continued
20.
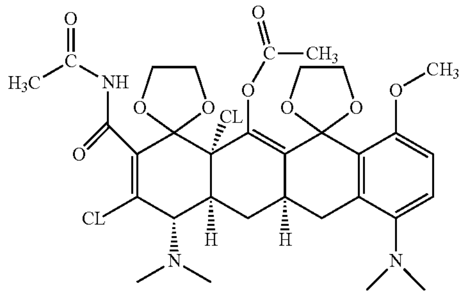
21.
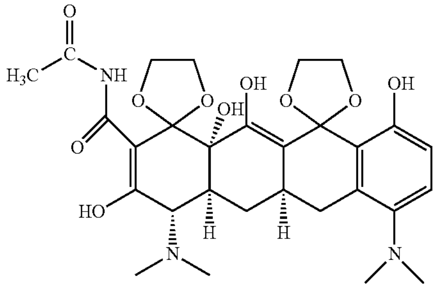
22.
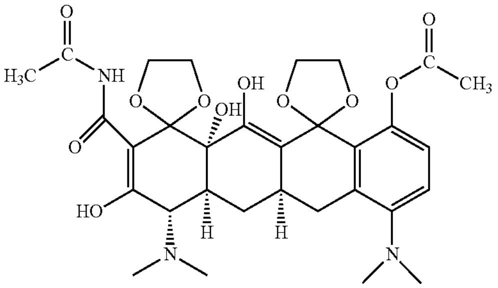
23.
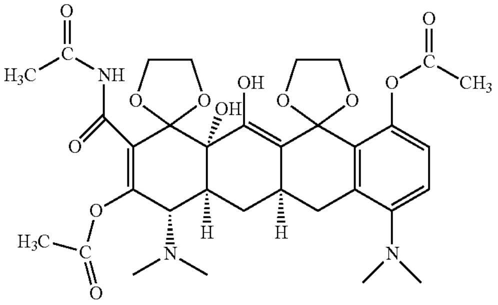
24.
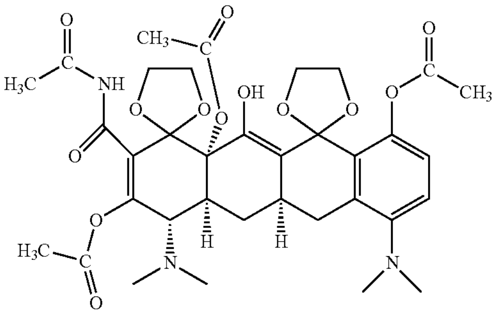
-continued
25.
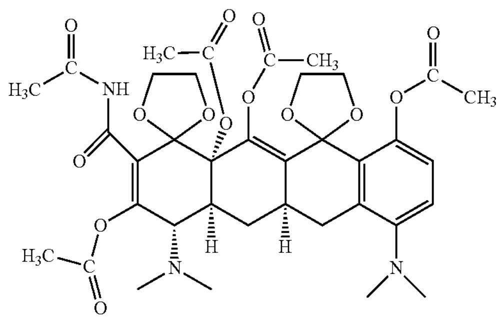
26.
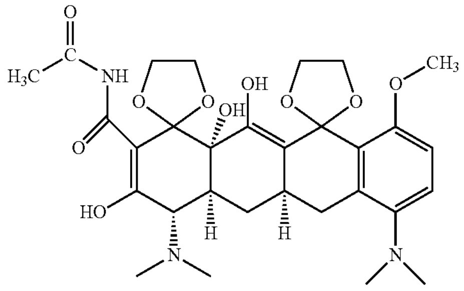
27.
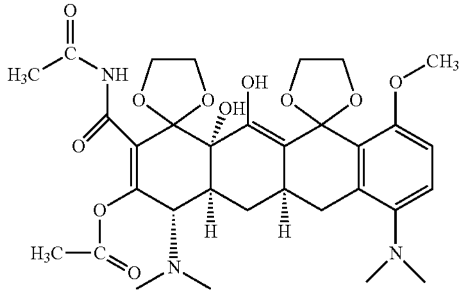
28.
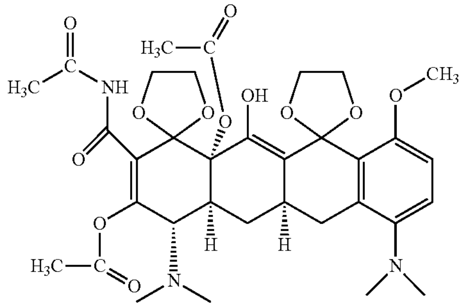
29.
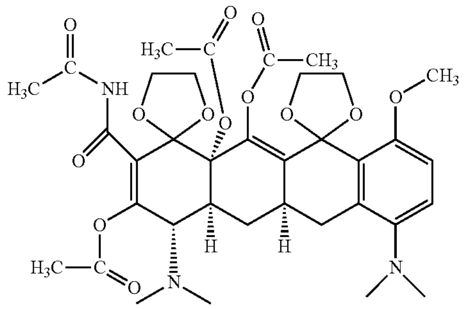

-continued
30.
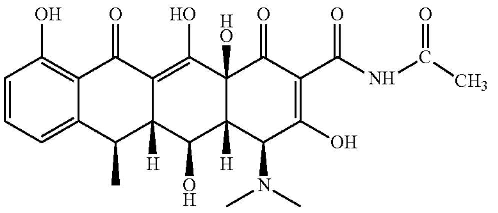
31.
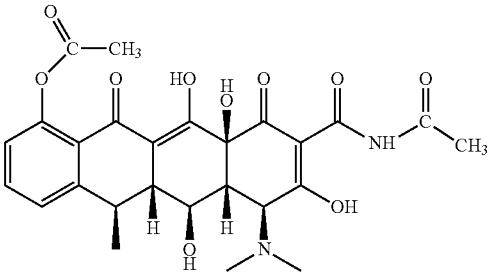
32.
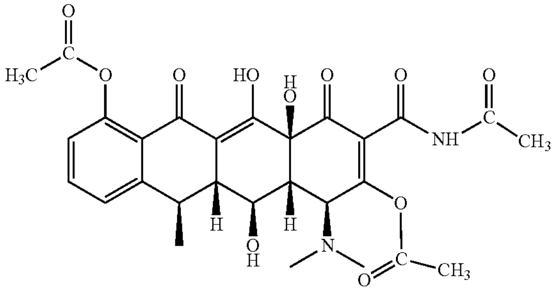
33.
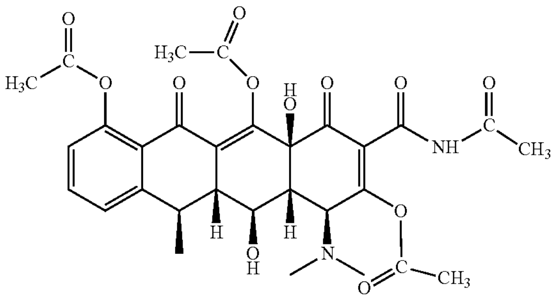
34.
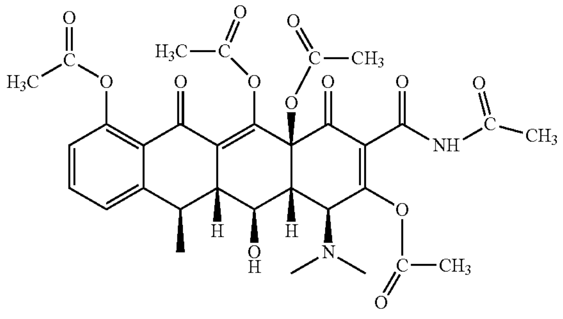
-continued
35.
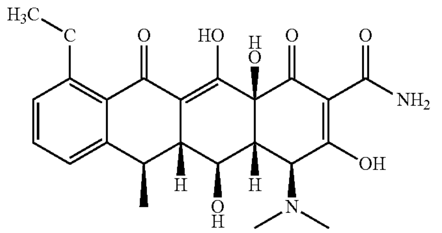
36.
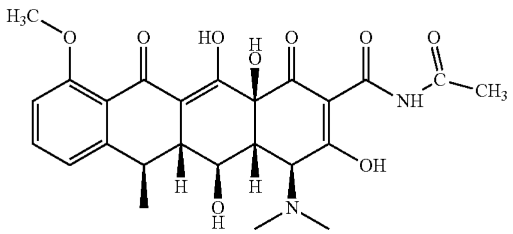
37.
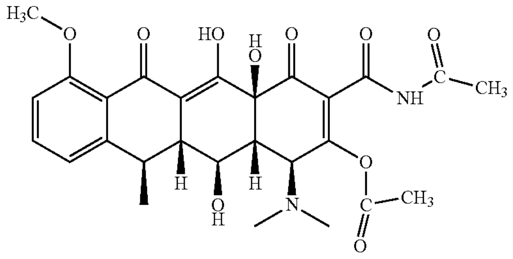
38.
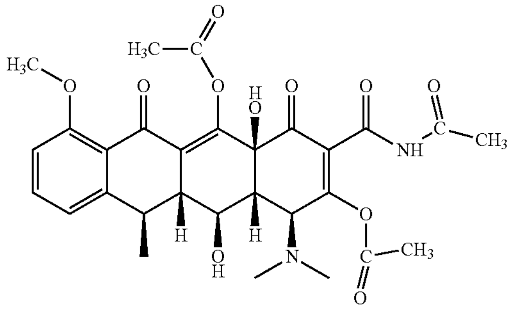
39.
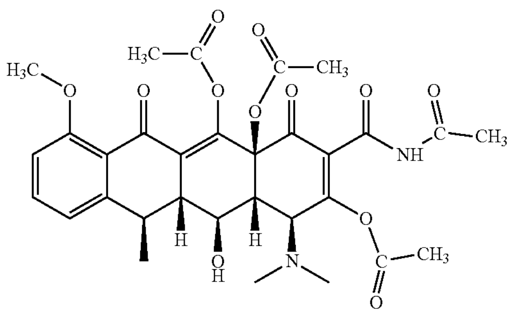

-continued
40.
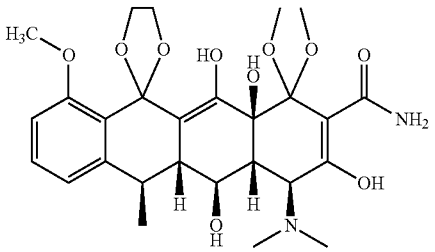
41.
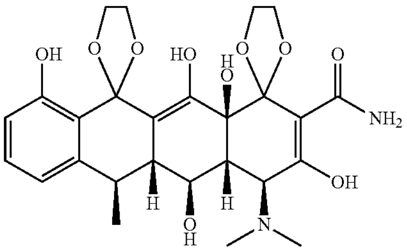
42.
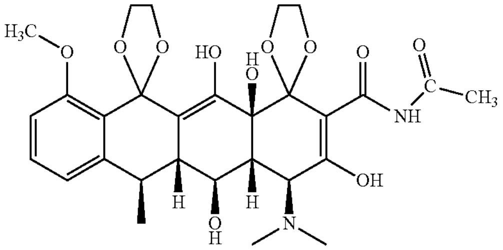
43.
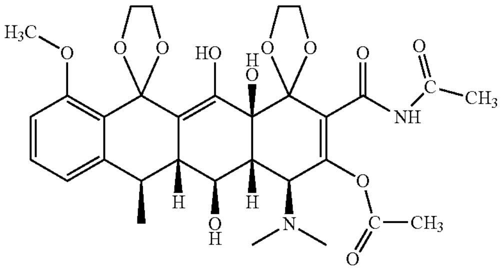
44.
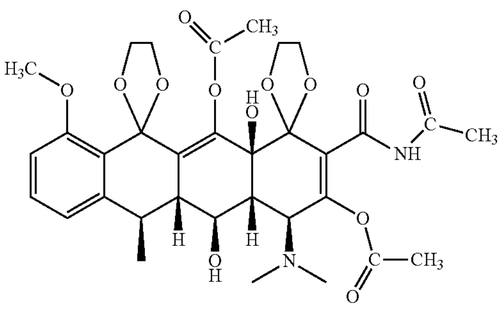
-continued
45.
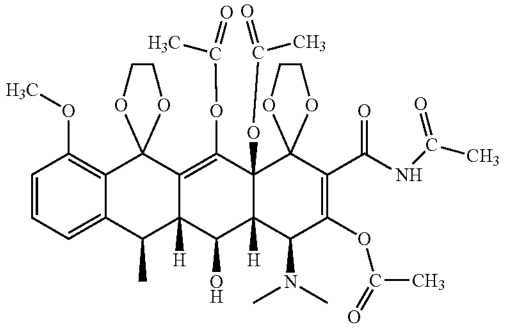
46.
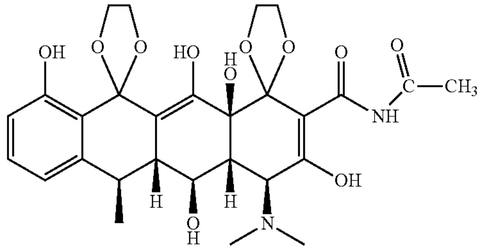
47.
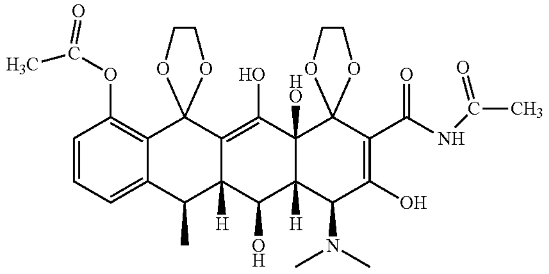
48.
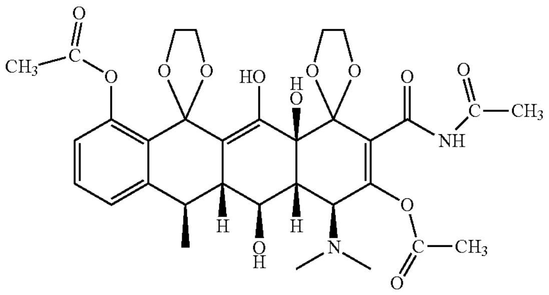
49.
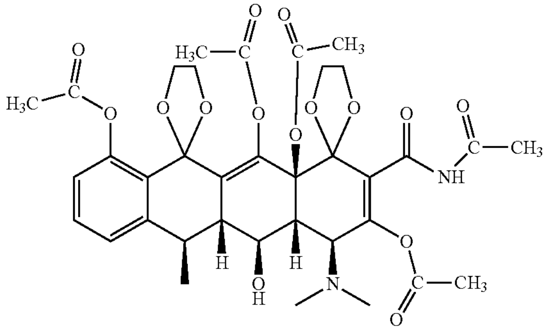

-continued
50.
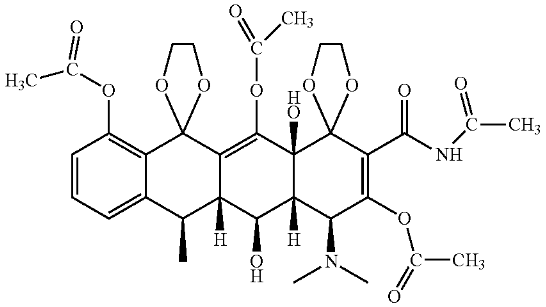
51.
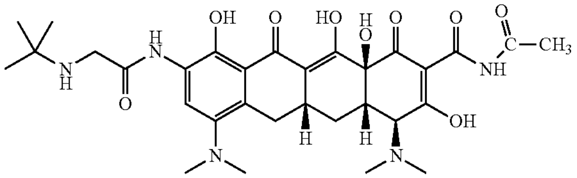
52.
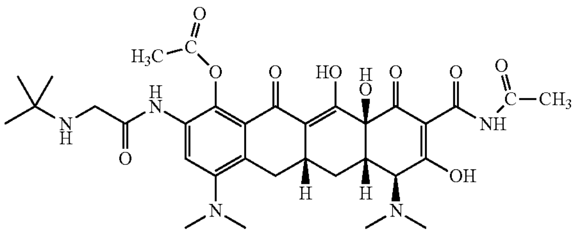
53.
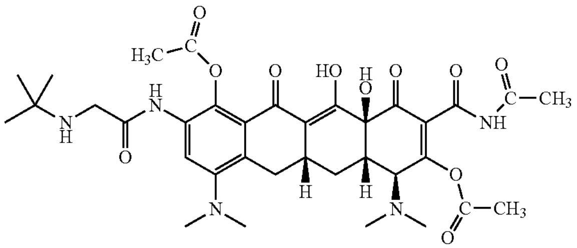
54.
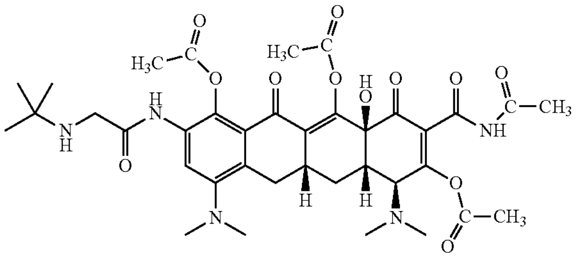
55.
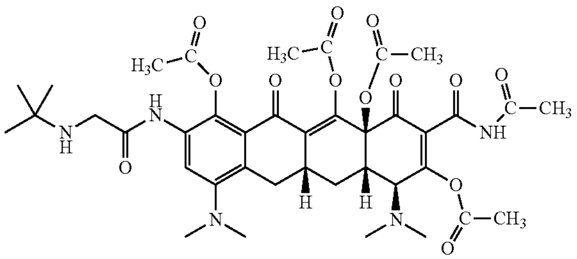
-continued
56.
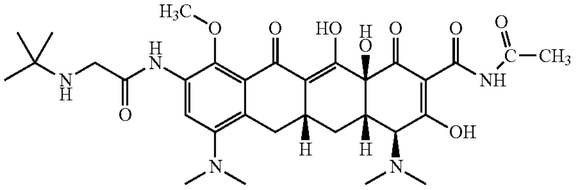
57.
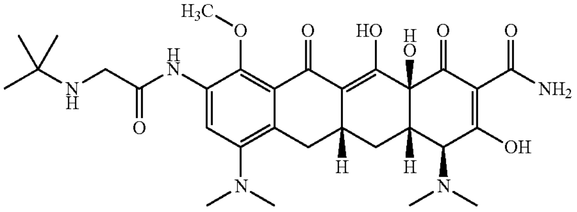
58.
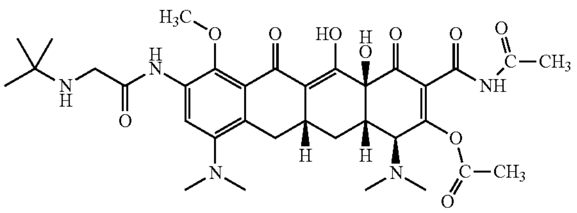
59.
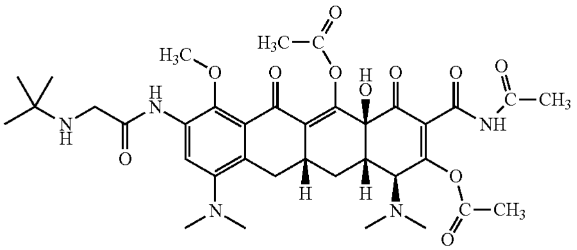
60.
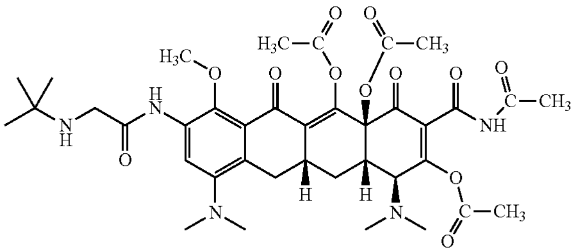
61.
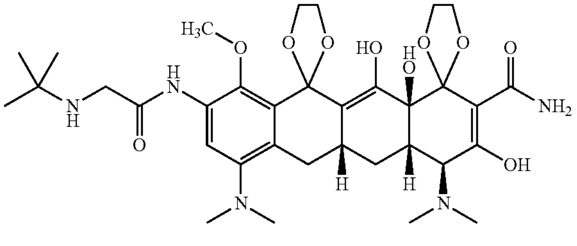

-continued
62.
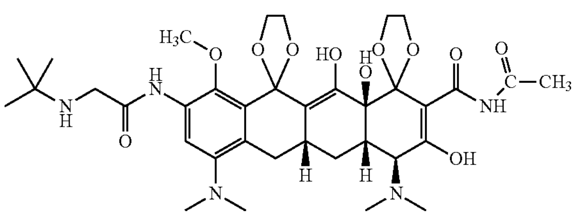
63.
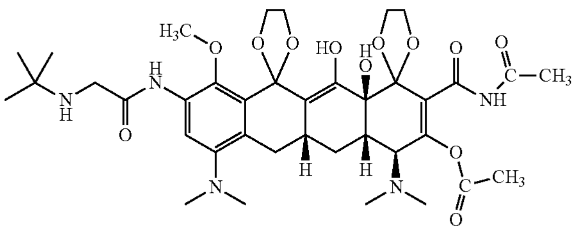
64.
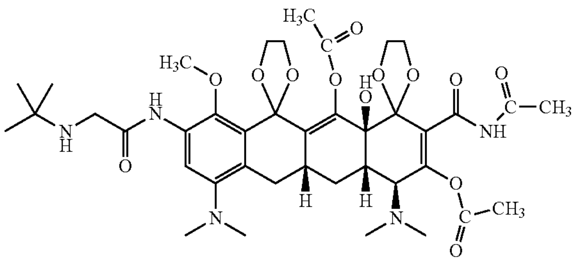
65.
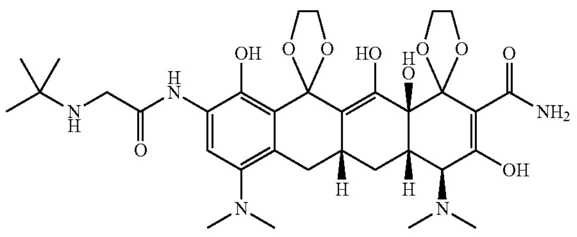
66.
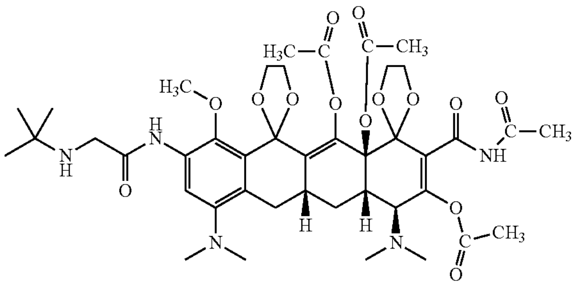
67.
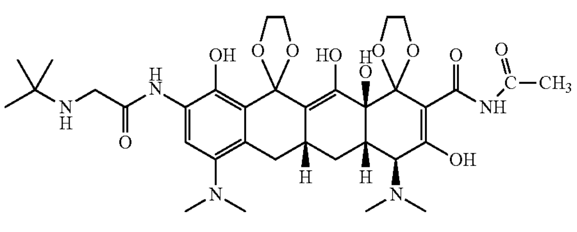
-continued
68.
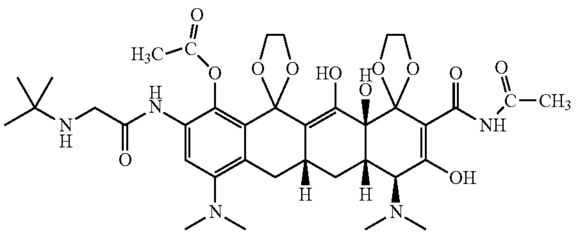
69.
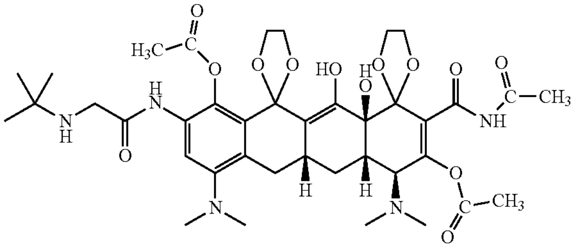
70.
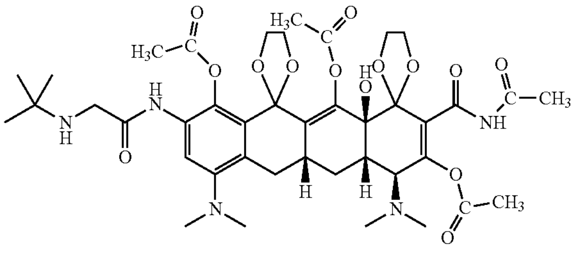
71.
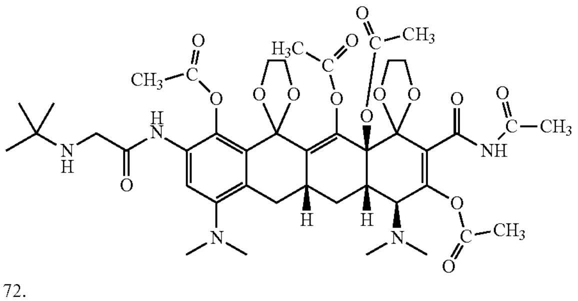
72.
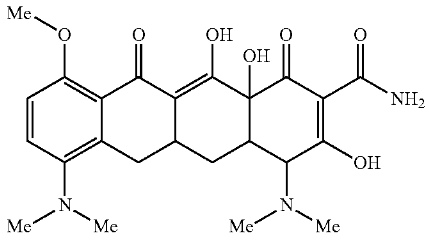
HCl;
73.
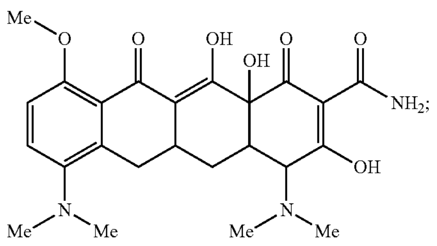

-continued
74.
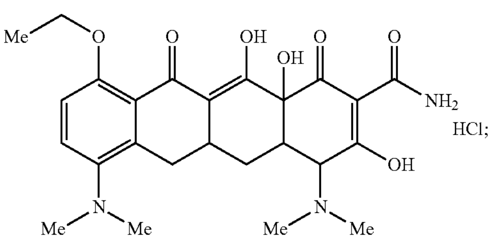
75.
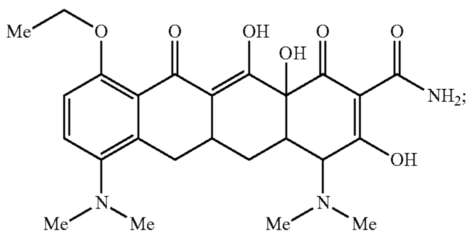
76.
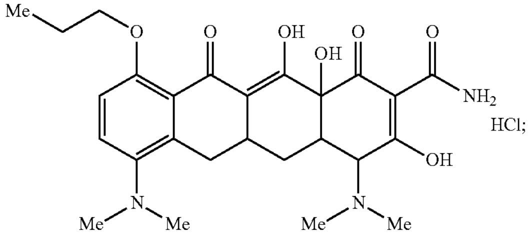
77.
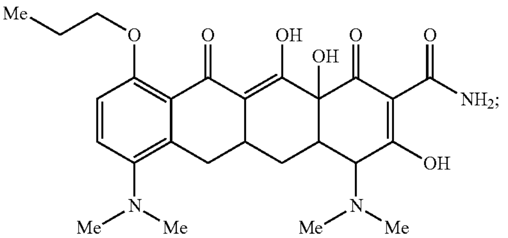
78.
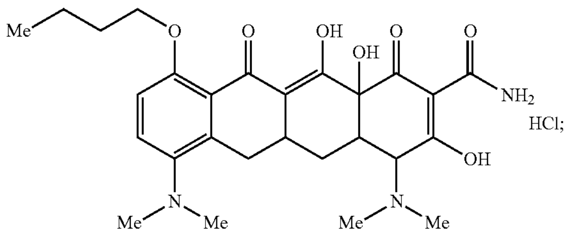
79.
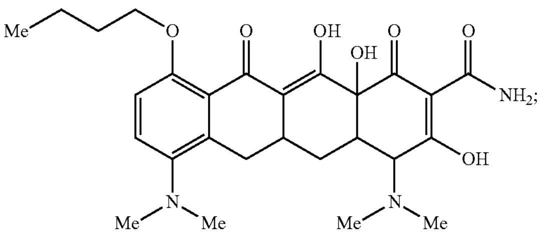
-continued
80.
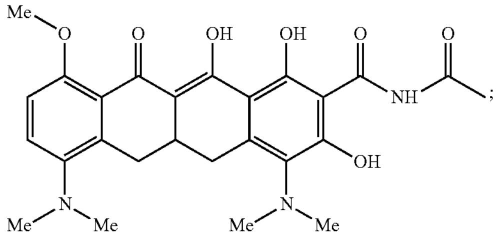
81.
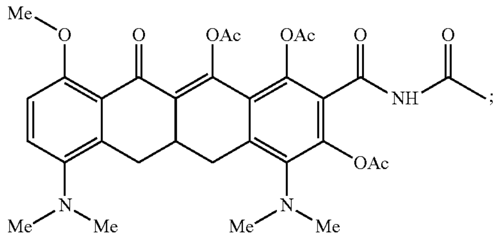
82.
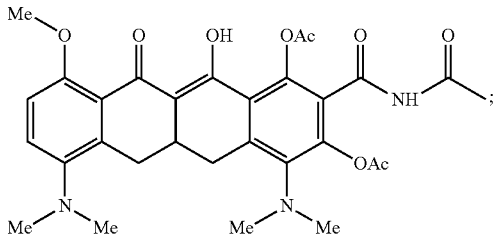
83.
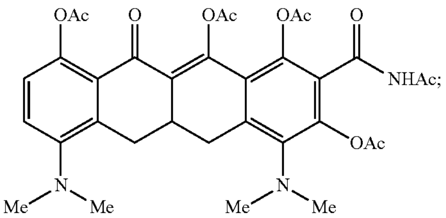
84.
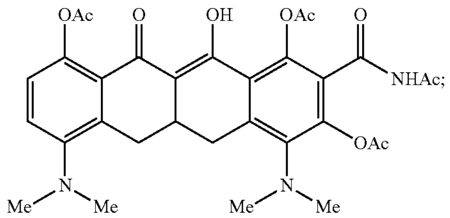
or
85.
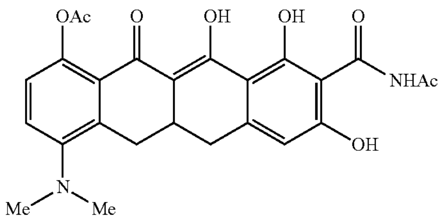

Table 2 includes a list that compares additional minocycline derivatives of the present invention to minocycline and, e.g., its HCl salt.

| S.N o | ChemDraw's Structure | ChemDraw's Names | Commercial Names (or) Given Names |
|---|---|---|---|
| 1 | 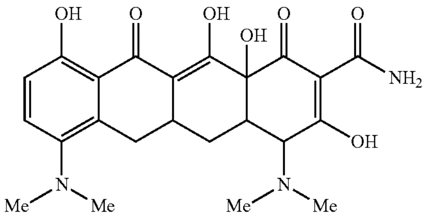 [SMILES: CN(C)c1ccc(O)c2c1CC1CC3C(N(C)C)C(O)=C(C(N)=O)C(=O)C3(O)C(O)=C1C2=O] | 4.7-Bis-dimcthylamino-3,10,12,12a-tctrahydroxy-1,11-dioxo-1,4.4a,5,5a,6,11,12 a-octahydro-naphthacene-2-carboxylic acid amide | Minocycline (MC) |
| 2 | 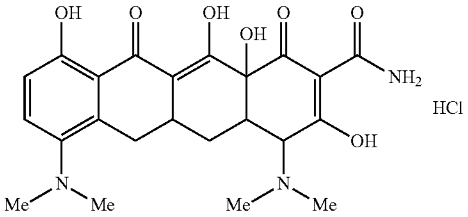 [SMILES: CN(C)c1ccc(O)c2c1CC1CC3C(N(C)C)C(O)=C(C(N)=O)C(=O)C3(O)C(O)=C1C2=O ; Cl] | 4.7-Bis-dimethylamino-3,10,12,12a-tetrahydroxy-1,11-dioxo-1,4,4a,5,5a,6,11,12a-a-octahydro-naphthacene-2-carboxylic acid amide. Hydrochloride | Minocycline hydrochloride (MC•HCl) |
| 3 | 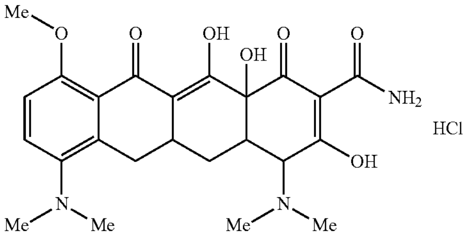 [SMILES: COc1ccc(N(C)C)c2c1C(=O)C1=C(O)C3(O)C(=O)C(C(N)=O)=C(O)C(N(C)C)C3CC1C2 ; Cl] | 4,7-Bis-dimethylamino-3,12,12a-trihydroxy-10-methoxy-1,11-dioxo-1,4,4a,5,5a,6,l1,12a-octahydro-naphthacene-2-carboxylic acid amide. Hydrochloride | Methyl Ether Minocycline. Hydrochloride (MEMC•HCl) |
| 4 | 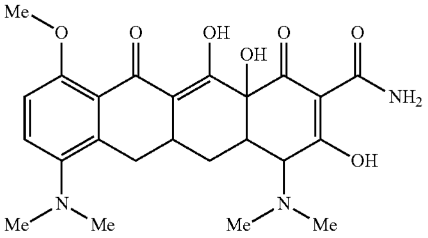 [SMILES: COc1ccc(N(C)C)c2c1C(=O)C1=C(O)C3(O)C(=O)C(C(N)=O)=C(O)C(N(C)C)C3CC1C2] | 4,7-Bis-dimethylamino-3,12,12a-trihydroxy-10-methoxy-1,11-dioxo-1,4,4a,5,5a,6,11,12a-octahydro-naphthacene-2-carboxylic acid amide | Methyl Ether Minocycline (MEMC) |
| 5 | 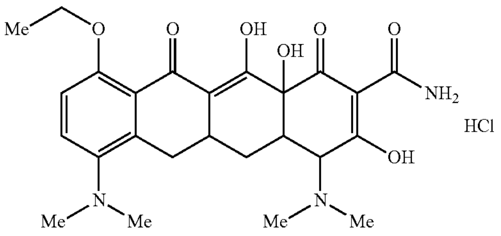 [SMILES: CCOc1ccc(N(C)C)c2c1C(=O)C1=C(O)C3(O)C(=O)C(C(N)=O)=C(O)C(N(C)C)C3CC1C2 ; Cl] | 4.7-Bis-dimethylamino-10-ethoxy-3,12,12a-trihydroxy-1,11-dioxo-1,4,4a,5,5a,6,11,12a-octahydro-naphthacene-2-carboxylic acid amide. Hydrochloride | Ethyl Ether Minocycline. Hydrochloride (EEMC•HCl) |
| 6 | 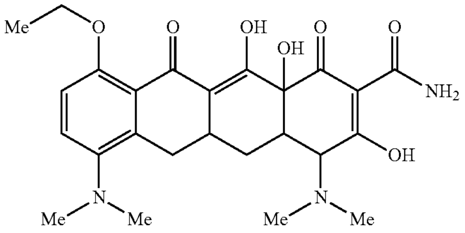 [SMILES: CCOc1ccc(N(C)C)c2c1C(=O)C1=C(O)C3(O)C(=O)C(C(N)=O)=C(O)C(N(C)C)C3CC1C2] | 4.7-Bis-dimethylamino-10-ethoxy-3,12,12a-trihydroxy-1,11-dioxo-1,4,4a,5,5a,6,11,12a-octahydro-naphthacene-2-carboxylic acid amide | Ethyl Ether Minocycline (EEMC) |

-continued

| S.No | ChemDraw's Structure | ChemDraw's Names | Commercial Names (or) Given Names |
|---|---|---|---|
| 7 | 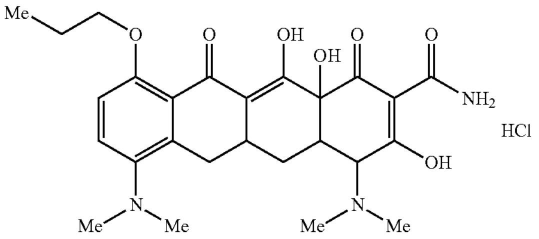 [SMILES: CCCOc1ccc(N(C)C)c2c1C(=O)C1=C(O)C3(O)C(=O)C(C(N)=O)=C(O)C(N(C)C)C3CC1C2 ; Cl] | 4.7-Bis-dimethylamino-3,12,12a-trihydroxy-1,11-dioxo-10-propoxy-1,4,4a,5,5a,6,11,12a-octahydro-naphthacene-2-carboxylic acid amide. Hydrochloride | Propyl Ether Minocycline. Hydrochloride (PEMC•HCl) |
| 8 | 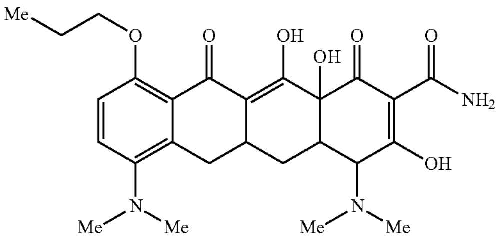 [SMILES: CCCOc1ccc(N(C)C)c2c1C(=O)C1=C(O)C3(O)C(=O)C(C(N)=O)=C(O)C(N(C)C)C3CC1C2] | 4,7-Bis-dimethylamino-3,12,12a-trihydroxy-1,11-dioxo-10-propoxy-l,4,4a,5,5a,6,11,12a-octahydro-naphthacene-2-carboxylic acid amide | Propyl Ether Minocycline (PEMC) |
| 9 | 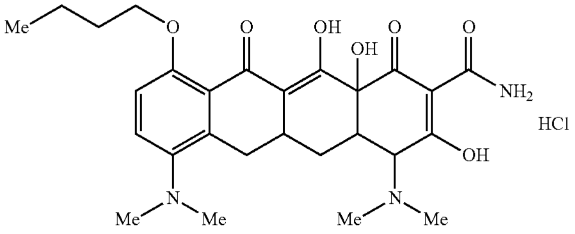 [SMILES: CCCCOc1ccc(N(C)C)c2c1C(=O)C1=C(O)C3(O)C(=O)C(C(N)=O)=C(O)C(N(C)C)C3CC1C2 ; Cl] | 10-Butoxy-4.7-bis-dimcthylamino-3,12,12a-trihydroxy-1,11-dioxo-l,4,4a,5,5a,6,l1,12a-octahydro-naphthacene-2-carboxylic acid amide. Hydrochloride | Butyl Ether Minocycline . . . Hydrochloride (BEMC•HCl) |
| 10 | 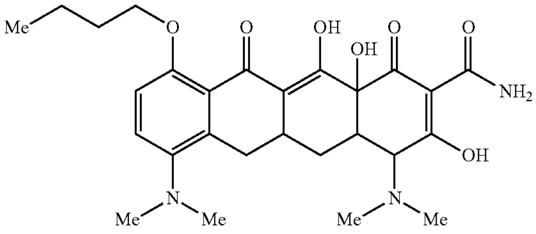 [SMILES: CCCCOc1ccc(N(C)C)c2c1C(=O)C1=C(O)C3(O)C(=O)C(C(N)=O)=C(O)C(N(C)C)C3CC1C2] | 10-Butoxy-4,7-bis-dimethylamino-3,12,12a-trihydroxy-1,11-dioxo-l,4,4a,5,5a,6,11,12a-octahydro-naphthacene-2-carboxylic acid amide | Butyl Ether Minocycline (BEMC) |
| 11 | 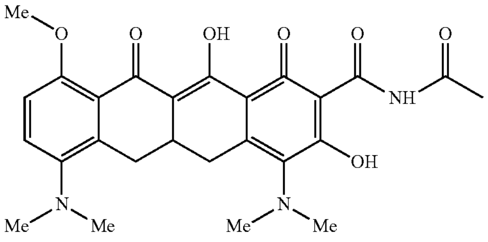 | 4,7-Bis-dimcthylamino-1,3,12-trihydroxy-10-methyloxy-11-oxo-5,5a,6,11-tetrahydro-naphthacene-2-carboxylic acid acetyl-amide | Methyl Ether N-Monoacetate Minocycline (MEMAMC) |
| 12 | 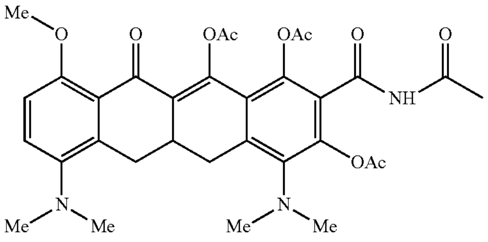 [SMILES: COc1ccc(N(C)C)c2c1C(=O)C1=C(OC(C)=O)c3c(c(N(C)C)c(OC(C)=O)c(C(=O)NC(C)=O)c3OC(C)=O)CC1C2] | Acetic acid 4,5-diacetoxy-3-acetylcarbamoyl-1,10-bis-dimethylamino-7-mcthoxy-6-oxo-6,11,1la,12a-tctrahydro-naphthacene-2-yl ester | Methyl Ether Tctra acetate Minocycline (METAMC) |

-continued

| S.No | ChemDraw's Structure | ChemDraw's Names | Commercial Names (or) Given Names |
|---|---|---|---|
| 13 | 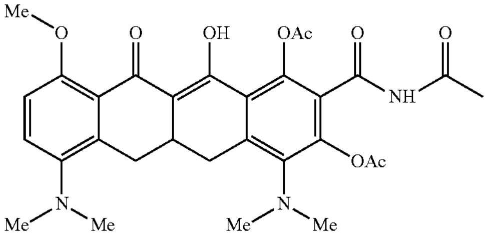 [SMILES: COc1ccc(N(C)C)c2c1C(=O)C1=C(O)c3c(c(N(C)C)c(OC(C)=O)c(C(=O)NC(C)=O)c3OC(C)=O)CC1C2] | Acetic acid 4-acetoxy-3-acetylcarbamoyl-1,10-bis-dimcthylamino-5-hydroxy-7-methoxy-6-oxo-6,11,11a,12-tetrahydro-naphthacen-2-yl ester | Methyl Ether Tri acetate Minocycline (METrAMC) |
| 14 | 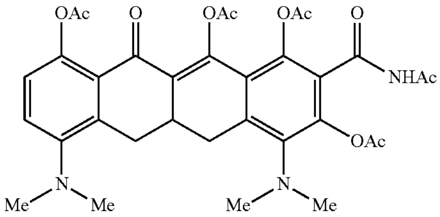 [SMILES: CC(=O)NC(=O)c1c(OC(C)=O)c2c(c(N(C)C)c1OC(C)=O)CC1Cc3c(N(C)C)ccc(OC(C)=O)c3C(=O)C1=C2OC(C)=O] | Acetic acid 3,10,12-triacetoxy-2-acetylcarbamoyl-4,7-bis-dimethylamino-11-oxo-5,5a,6,11-tetrahydro-naphthacen-1-yl ester | Penta acetyl Minocycline (PAMC) |
| 15 | 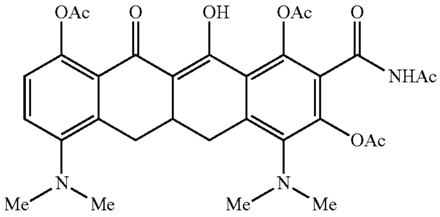 [SMILES: CC(=O)NC(=O)c1c(OC(C)=O)c2c(c(N(C)C)c1OC(C)=O)CC1Cc3c(N(C)C)ccc(OC(C)=O)c3C(=O)C1=C2O] | Acetic acid 3,10-diacetoxy-2-acetylcarbamoyl-4,7-bis-dimethylamino-12-hydroxy-11-oxo-5,5a,6,11-tetrahydro-naphthacen-1-yl ester | Tetra acetyl Minocycline (TAMC) |
| 16 | 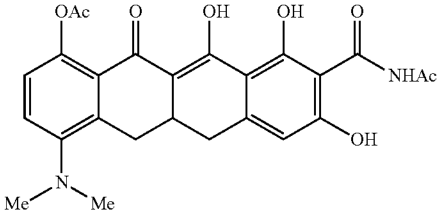 [SMILES: CC(=O)NC(=O)c1c(O)cc2c(c1O)C(O)=C1C(=O)c3c(OC(C)=O)ccc(N(C)C)c3CC1C2] | Acetic acid 9-acctylcarbamoyl-4-dimethylamino-8,10,11-trihydroxy-12-oxo-5,5a,6,12-tetrahydro-naphthacen-1-yl ester | De Methyl Diacetatc Minocycline (DMDAMC) |

Figure 8C:
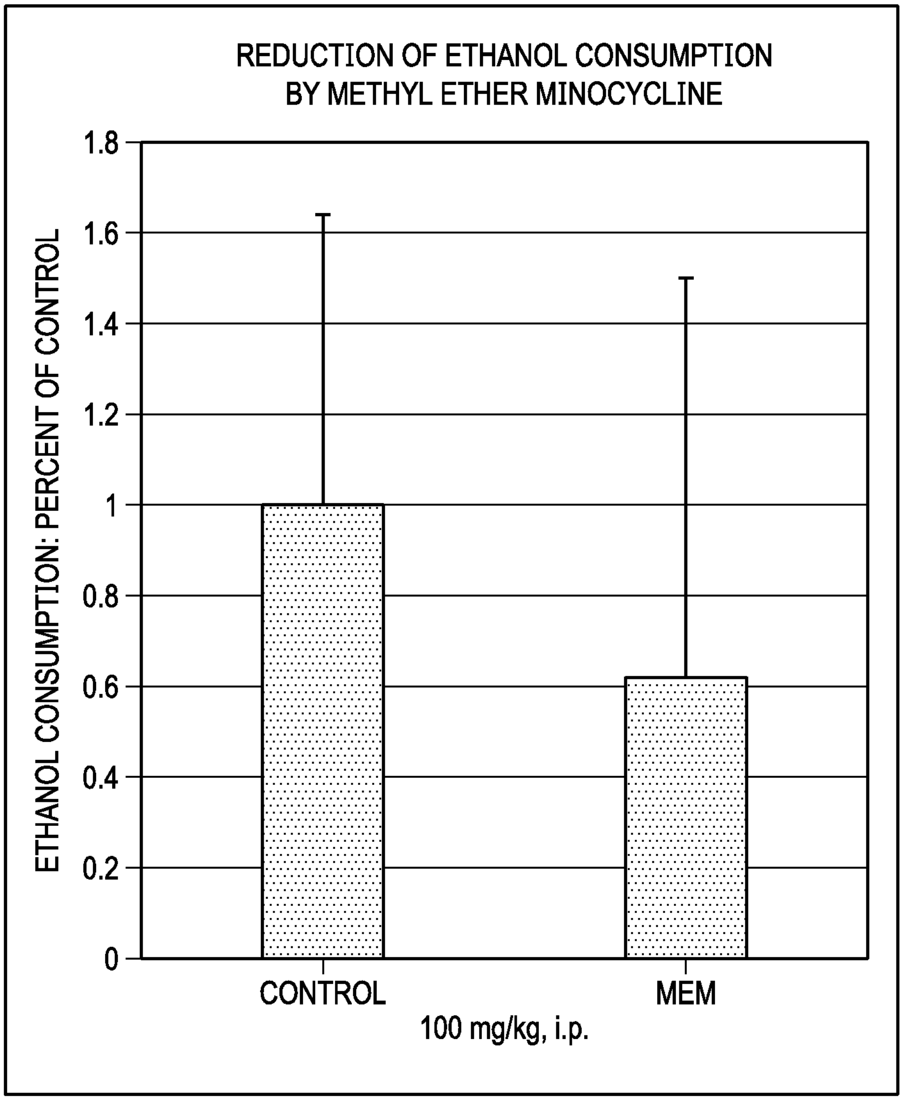

FIGS. 8A to 8C show the activity of Methyl Ether Minocycline (4,7-Bis-dimethylamino-3,12,12a-trihydroxy-10-methoxy-1,11-dioxo-1,4,4a,5,5a,6,11,12a-octahydro-naphthacene-2-carboxylic acid amide, Hydrochloride), as shown with FIG. 8A *E coli* MM294 GFP zone of inhibition, FIG. 8B *E coli* MM294 GFP CFU/disc, and FIG. 8C reduction of binge ethanol consumption.

Figure 9A:
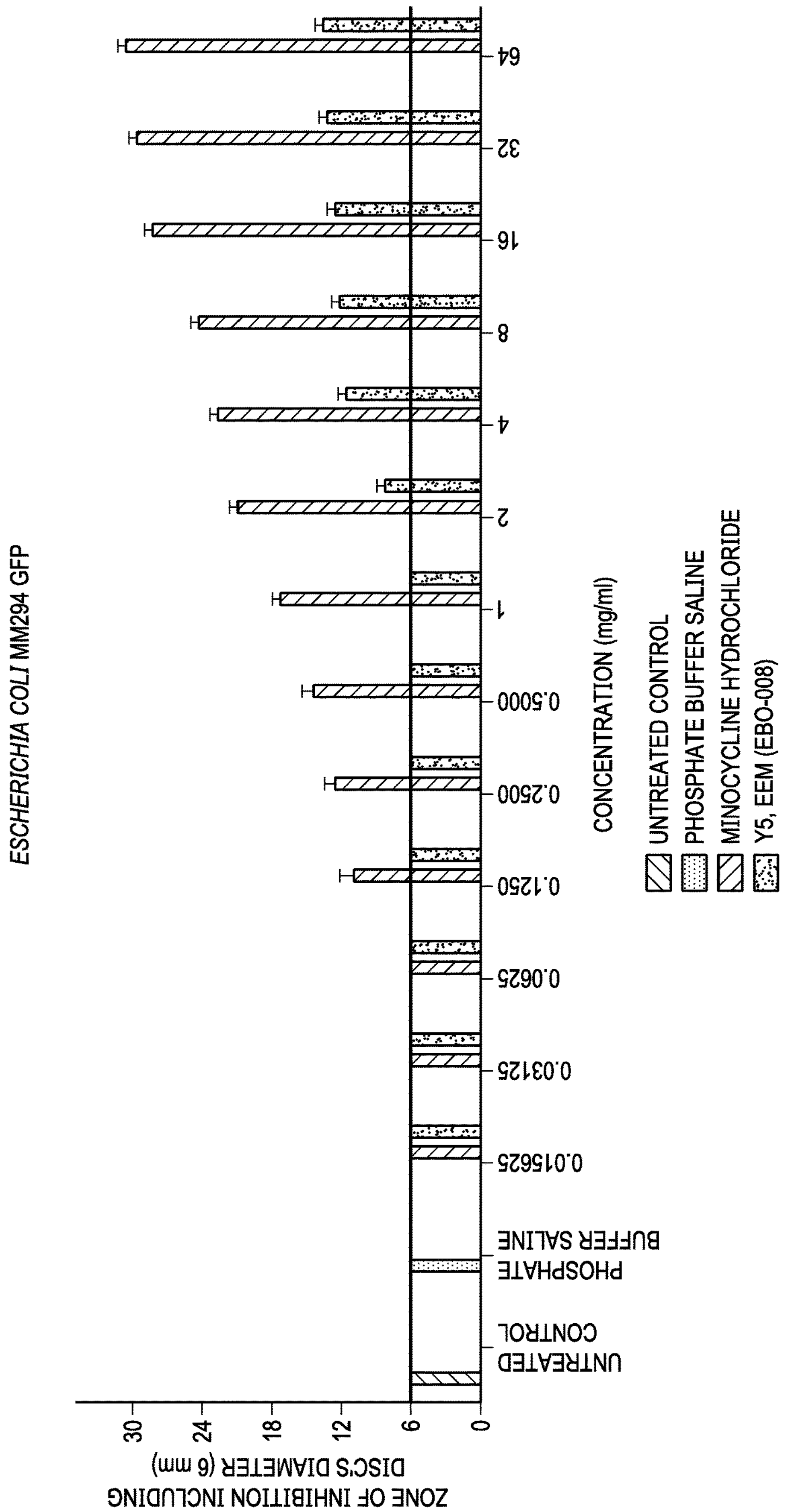
FIGS. 9A to 9E show the activity of Ethyl Ether Minocycline (4,7-Bis-dimethylamino-10-ethoxy-3,12,12a-trihydroxy-1,11-dioxo-1,4,4a,5,5a,6,11,12a-octahydro-naphthacene-2-carboxylic acid amide, and the Hydrochloride salt), as shown with FIG. 9A *E. coli* MM294 GFP zone of inhibition, FIG. 9B *E. coli* MM294 GFP CFU/disc, FIG. 9C *E. coli* MM294 GFP zone of inhibition with the hydrochloride salt, FIG. 9D *E. coli* MM294 GFP CFU/disc inhibition with the hydrochloride salt, and FIG. 9E reduction of binge ethanol consumption.
Figure 9B:
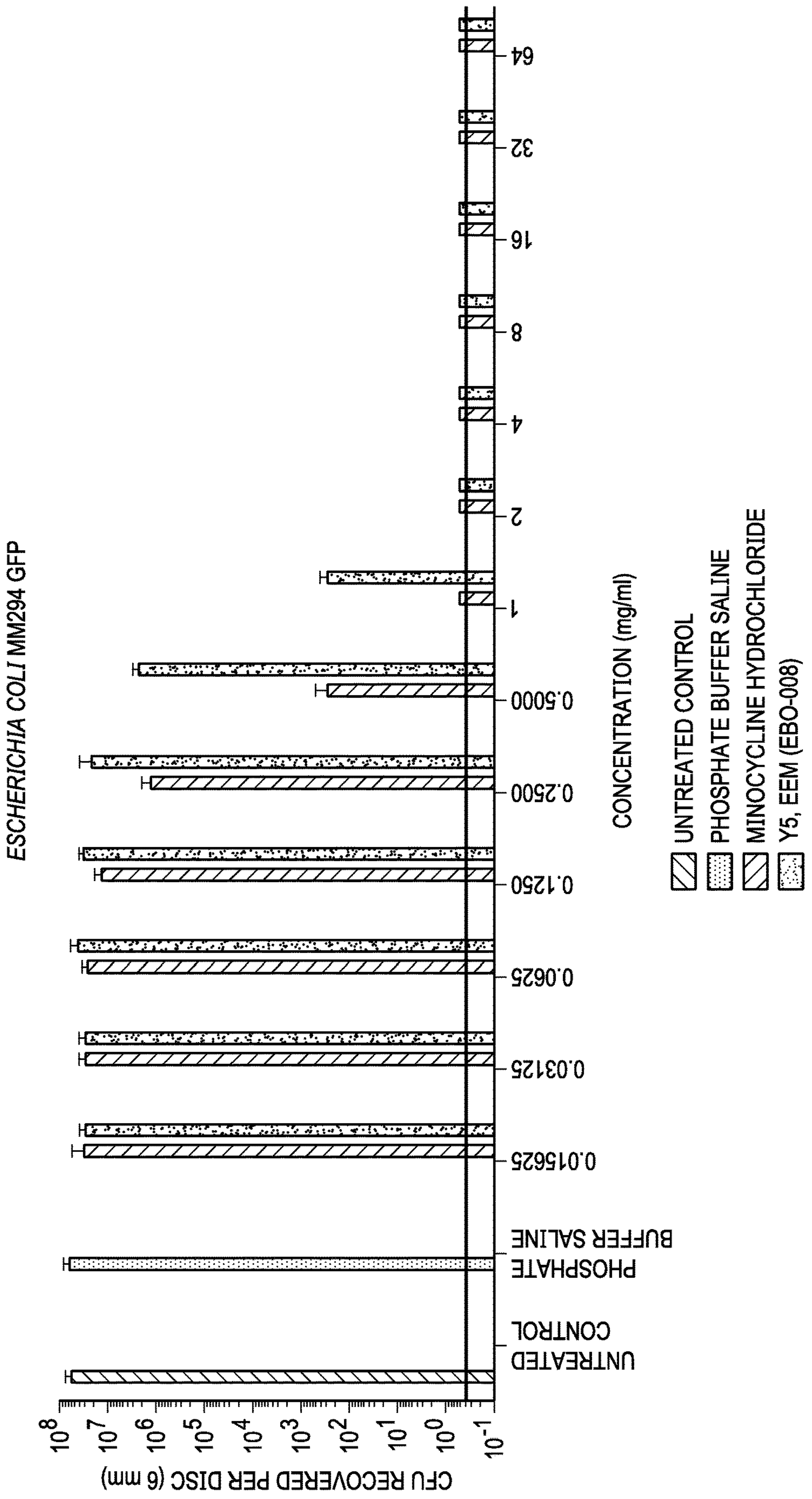
Figure 9C:
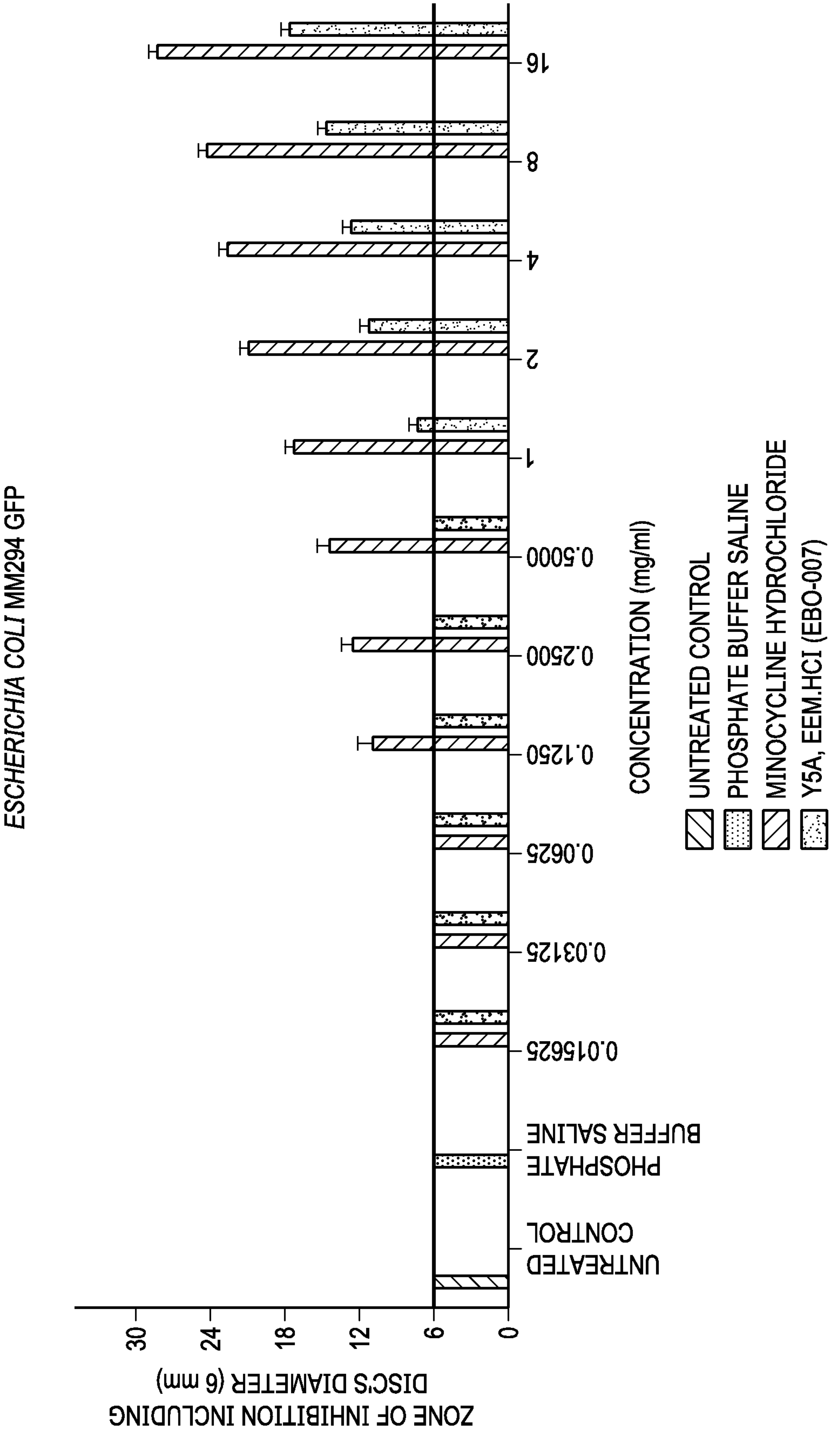
Figure 9D:
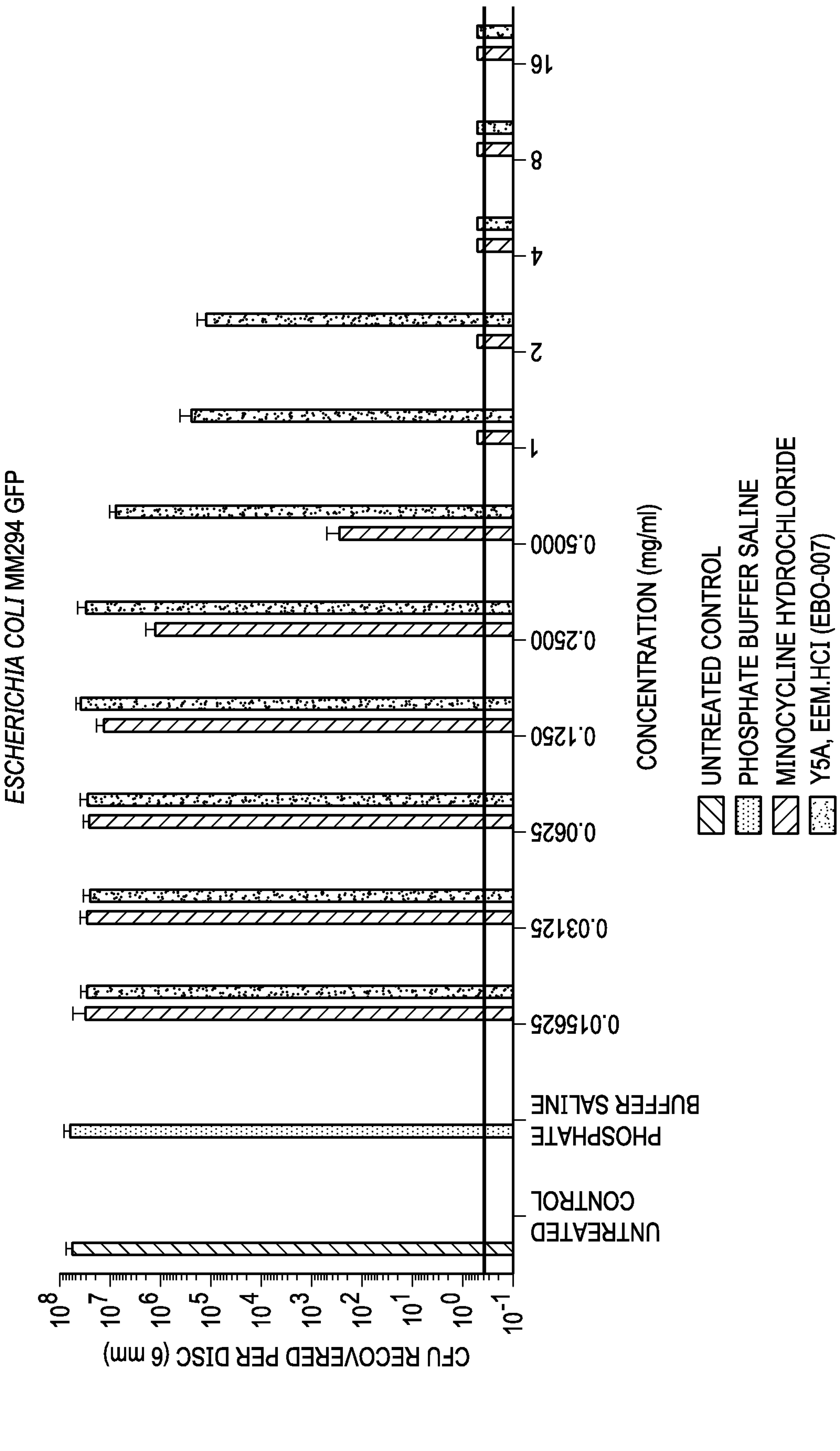
Figure 9E:
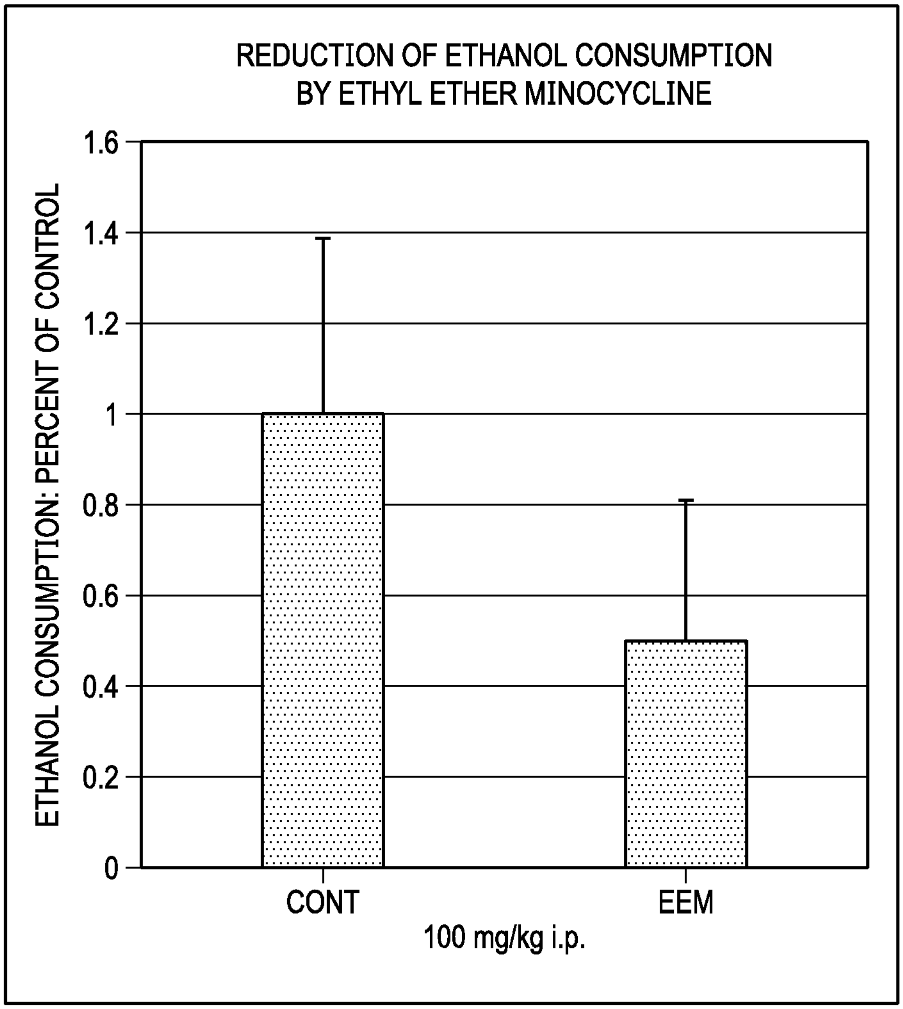

FIGS. 9A to 9E show the activity of Ethyl Ether Minocycline (4,7-Bis-dimethylamino-10-ethoxy-3,12,12a-trihydroxy-1,11-dioxo-1,4,4a,5,5a,6,11,12a-octahydro-naphthacene-2-carboxylic acid amide, and the Hydrochloride salt), as shown with FIG. 9A *E. coli* MM294 GFP zone of inhibition, FIG. 9B *E. coli* MM294 GFP CFU/disc, FIG. 9C *E. coli* MM294 GFP zone of inhibition with the hydrochloride salt, FIG. 9D *E. coli* MM294 GFP CFU/disc inhibition with the hydrochloride salt, and FIG. 9E reduction of binge ethanol consumption.

Figure 10A:
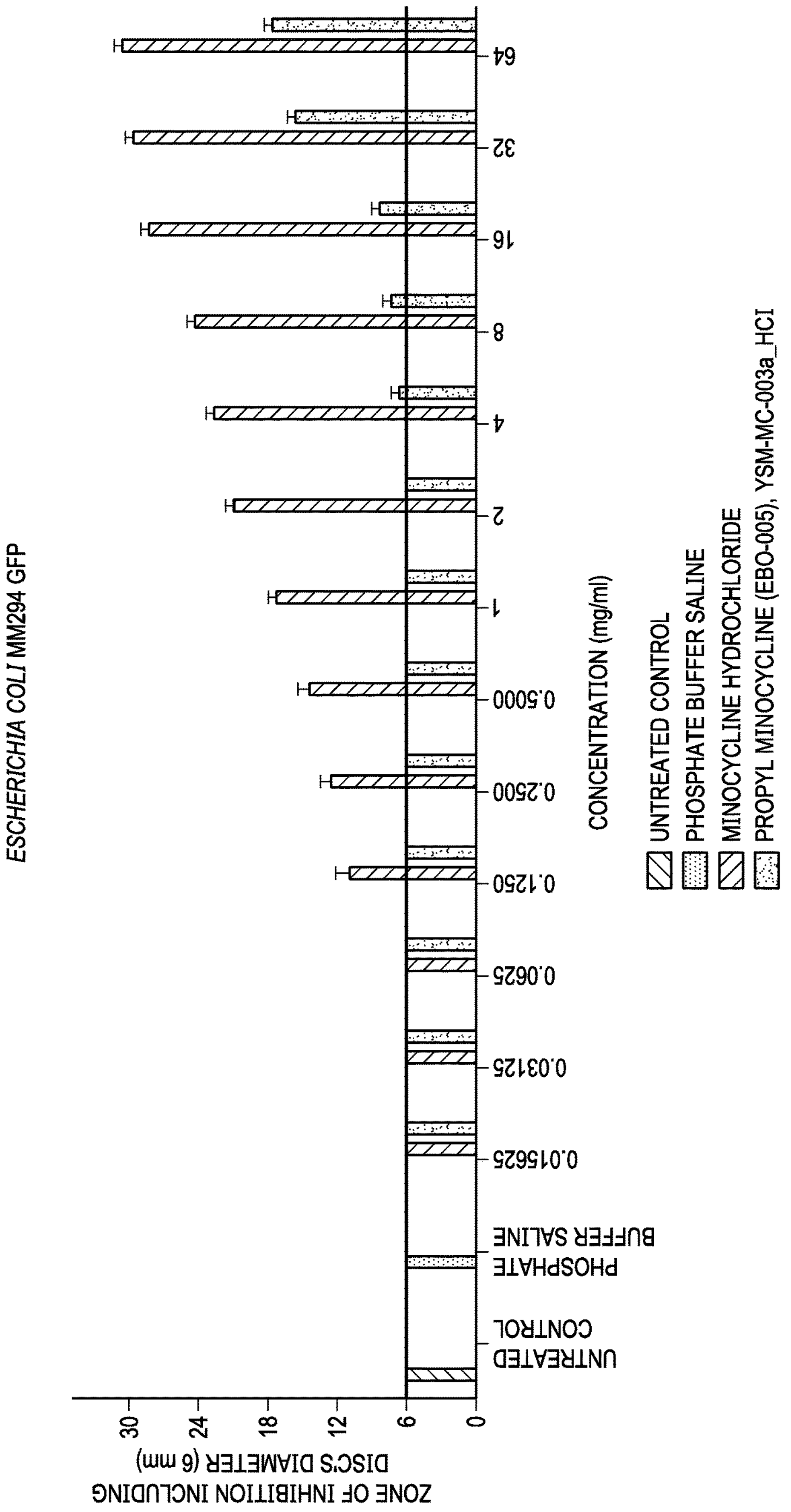
FIGS. 10A to 10E show the activity of Propyl Ether Minocycline (4,7-Bis-dimethylamino-3,12,12a-trihydroxy-1,11-dioxo-10-propoxy-1,4,4a,5,5a,6,11,12a-octahydro-naphthacene-2-carboxylic acid amide, and the Hydrochloride salt), as shown with FIG. 10A *E. coli* MM294 GFP zone of inhibition, FIG. 10B *E. coli* MM294 GFP CFU/disc, FIG. 10C *E. coli* MM294 GFP zone of inhibition with the hydrochloride salt, FIG. 10D *E. coli* MM294 GFP CFU/disc inhibition with the hydrochloride salt, and FIG. 10E reduction of binge ethanol consumption.
Figure 10B:
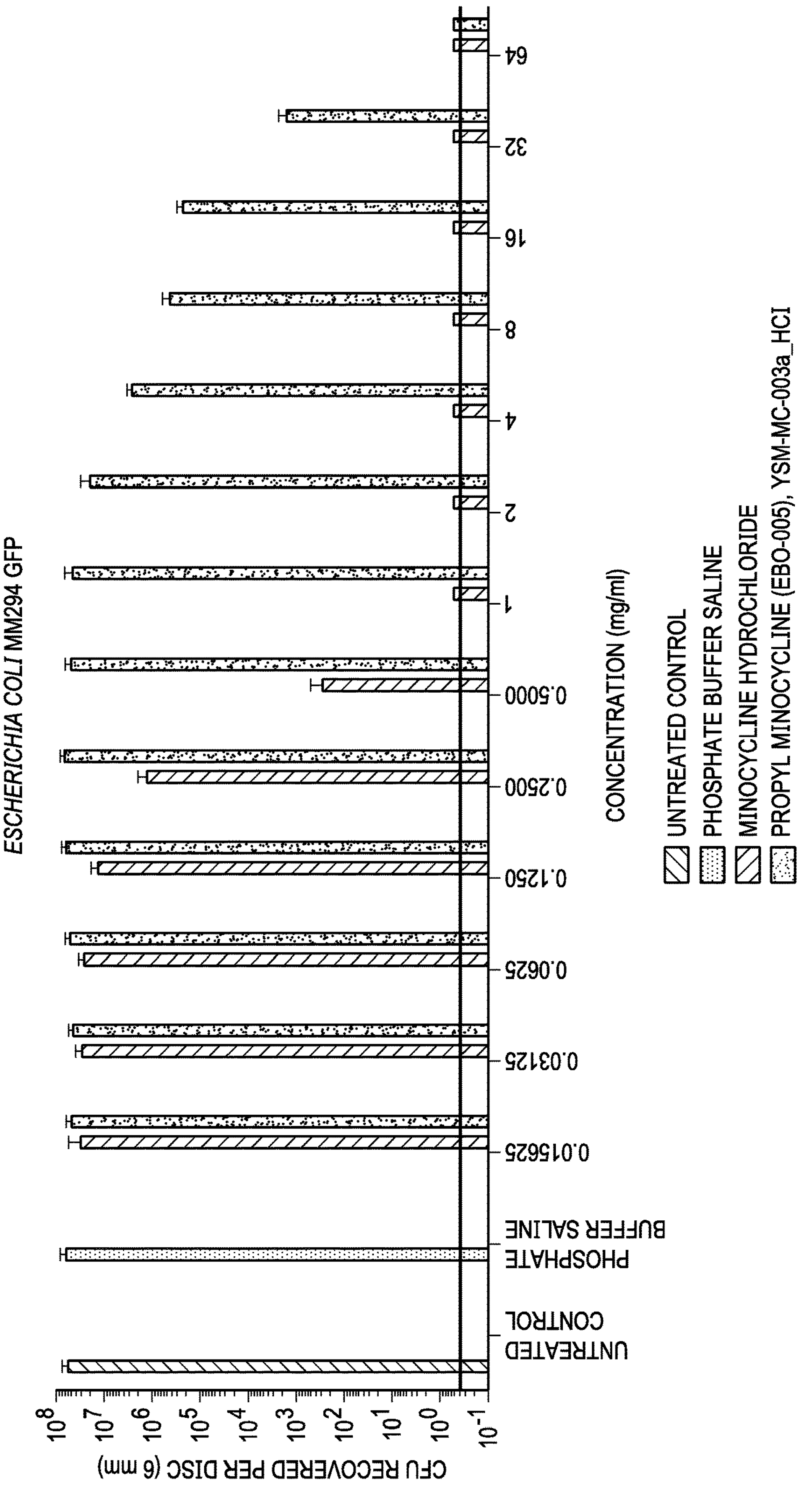
Figure 10C:
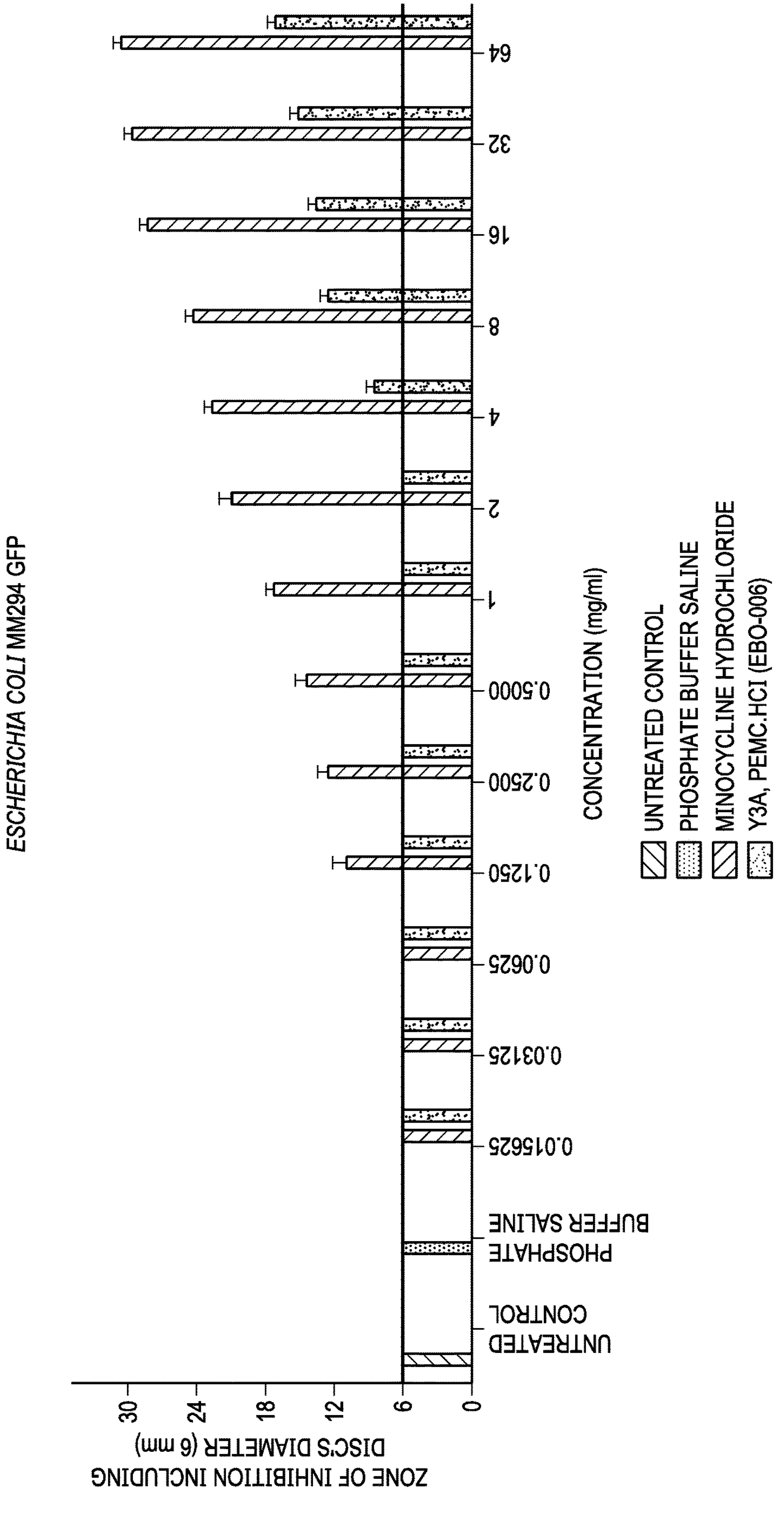
Figure 10D:
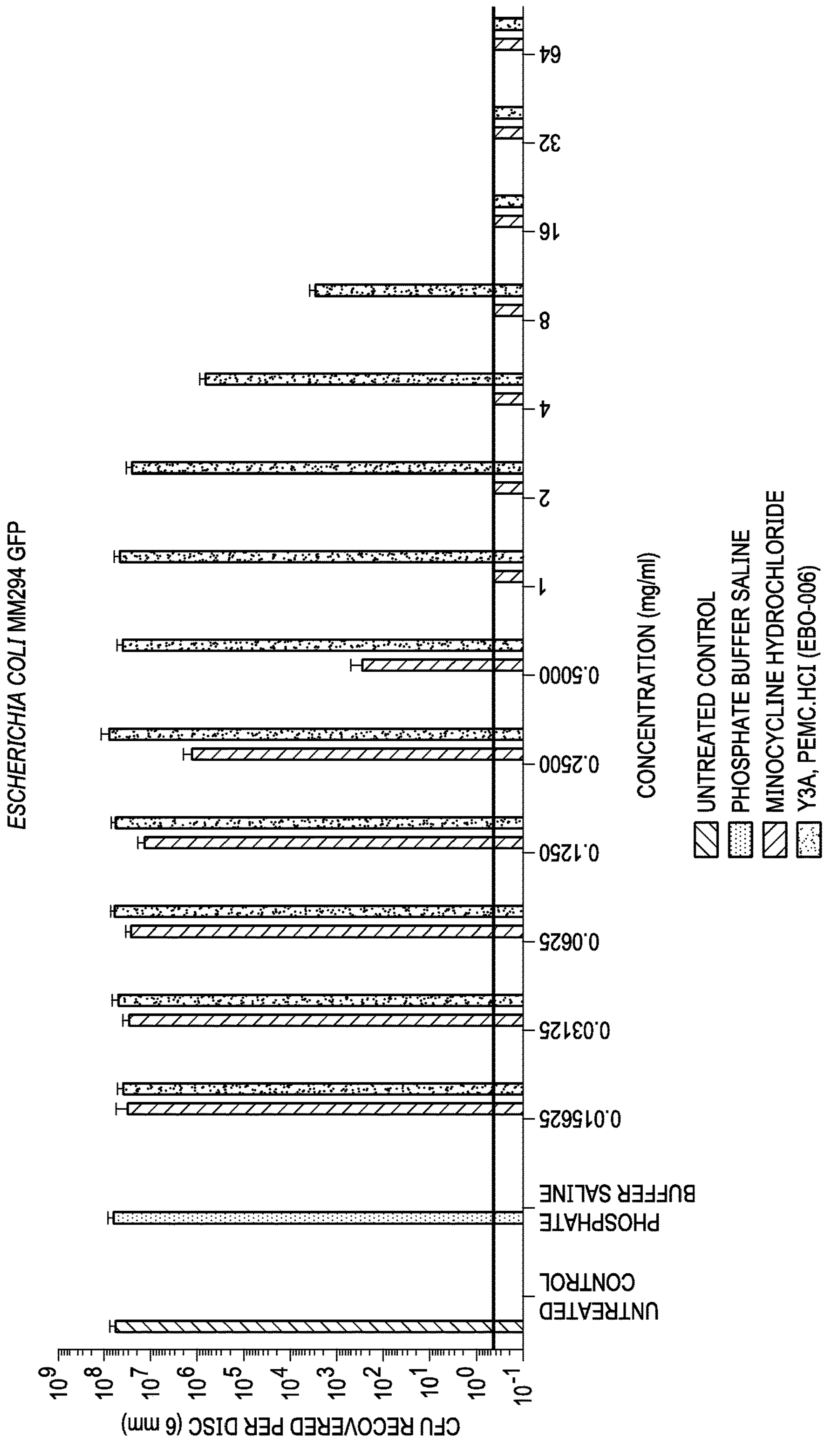
Figure 10E:
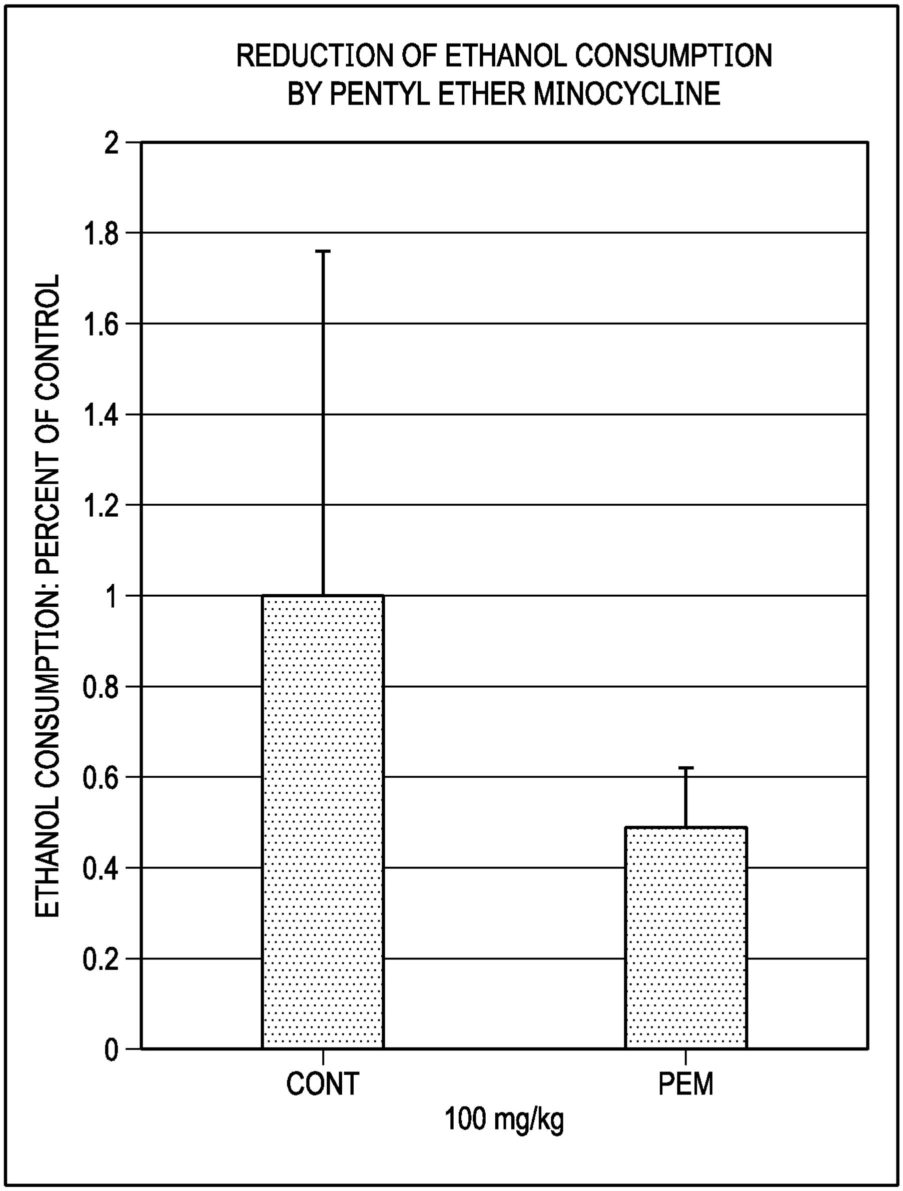

FIGS. 10A to 10E show the activity of Propyl Ether Minocycline (4,7-Bis-dimethylamino-3,12,12a-trihydroxy-1,11-dioxo-10-propoxy-1,4,4a,5,5a,6,11,12a-octahydro-naphthacene-2-carboxylic acid amide, and the Hydrochloride salt), as shown with FIG. 10A *E. coli* MM294 GFP zone of inhibition, FIG. 10B *E. coli* MM294 GFP CFU/disc, FIG. 10C *E. coli* MM294 GFP zone of inhibition with the hydrochloride salt, FIG. 10D *E. coli* MM294 GFP CFU/disc inhibition with the hydrochloride salt, and FIG. 10E reduction of binge ethanol consumption.

Figure 11A:
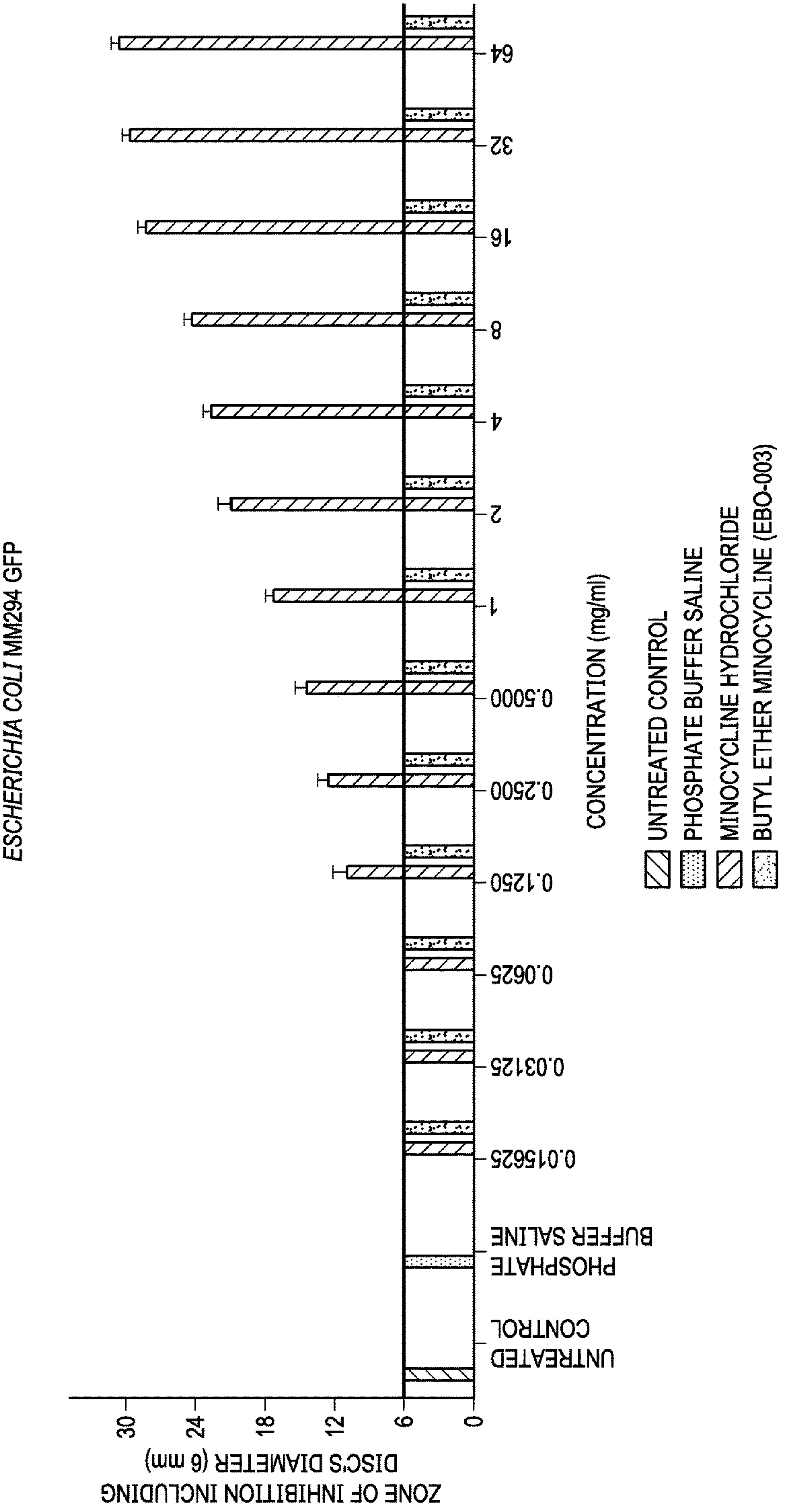
FIGS. 11A to 11C show the activity of Butyl Ether Minocycline (10-Butoxy-4,7-bis-dimethylamino-3,12,12a-trihydroxy-1,11-dioxo-1,4,4a,5,5a,6,11,12a-octahydro-naphthacene-2-carboxylic acid amide, and the Hydrochloride salt), as shown with FIG. 11A *E. coli* MM294 GFP zone of inhibition, FIG. 11B *E. coli* MM294 GFP CFU/disc, and FIG. 11C reduction of binge ethanol consumption.
Figure 11B:
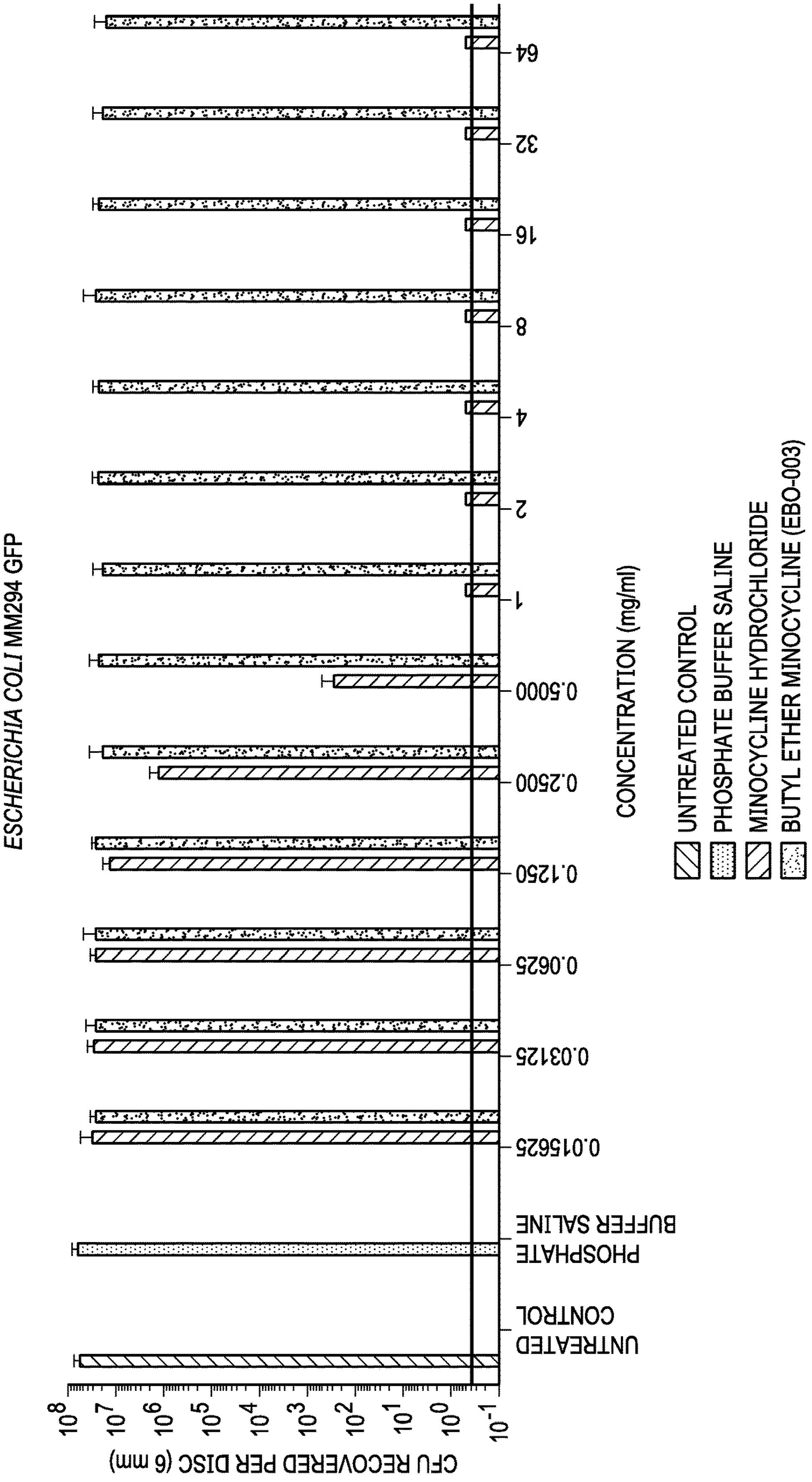
Figure 11C:
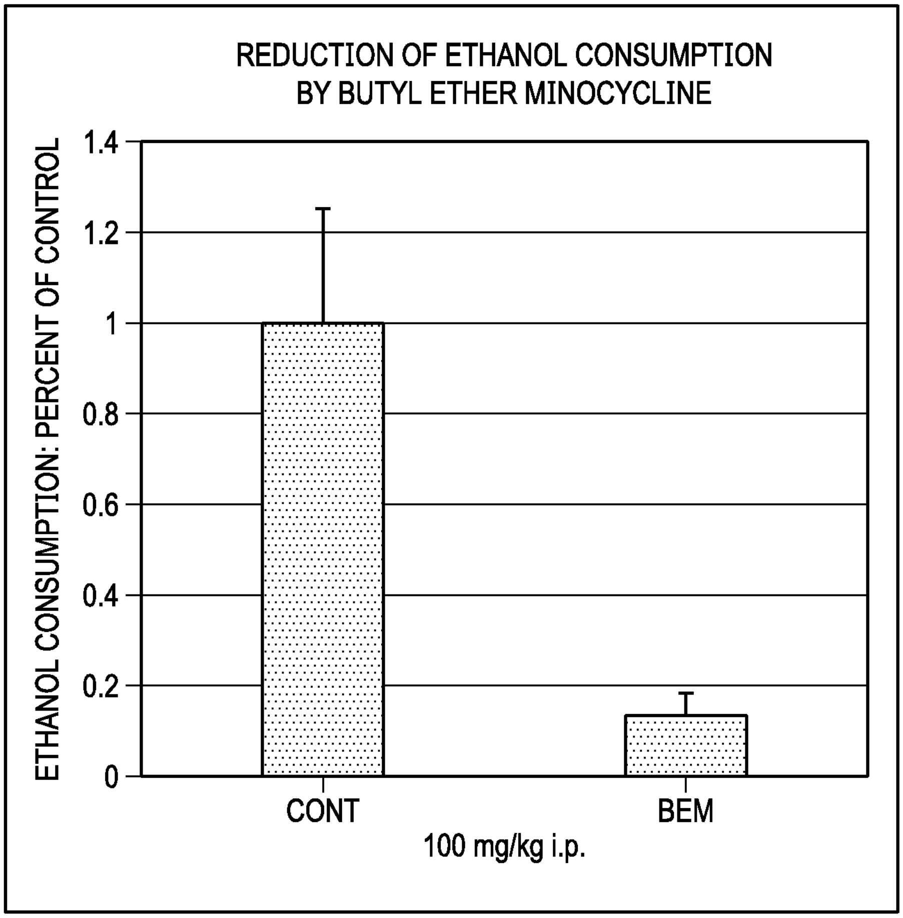

FIGS. 11A to 11C show the activity of Butyl Ether Minocycline (10-Butoxy-4,7-bis-dimethylamino-3,12,12a-trihydroxy-1,11-dioxo-1,4,4a,5,5a,6,11,12a-octahydro-naphthacene-2-carboxylic acid amide, and the Hydrochloride salt), as shown with FIG. 11A *E. coli* MM294 GFP zone of inhibition, FIG. 11B *E. coli* MM294 GFP CFU/disc, and FIG. 11C reduction of binge ethanol consumption.

Figure 12A:
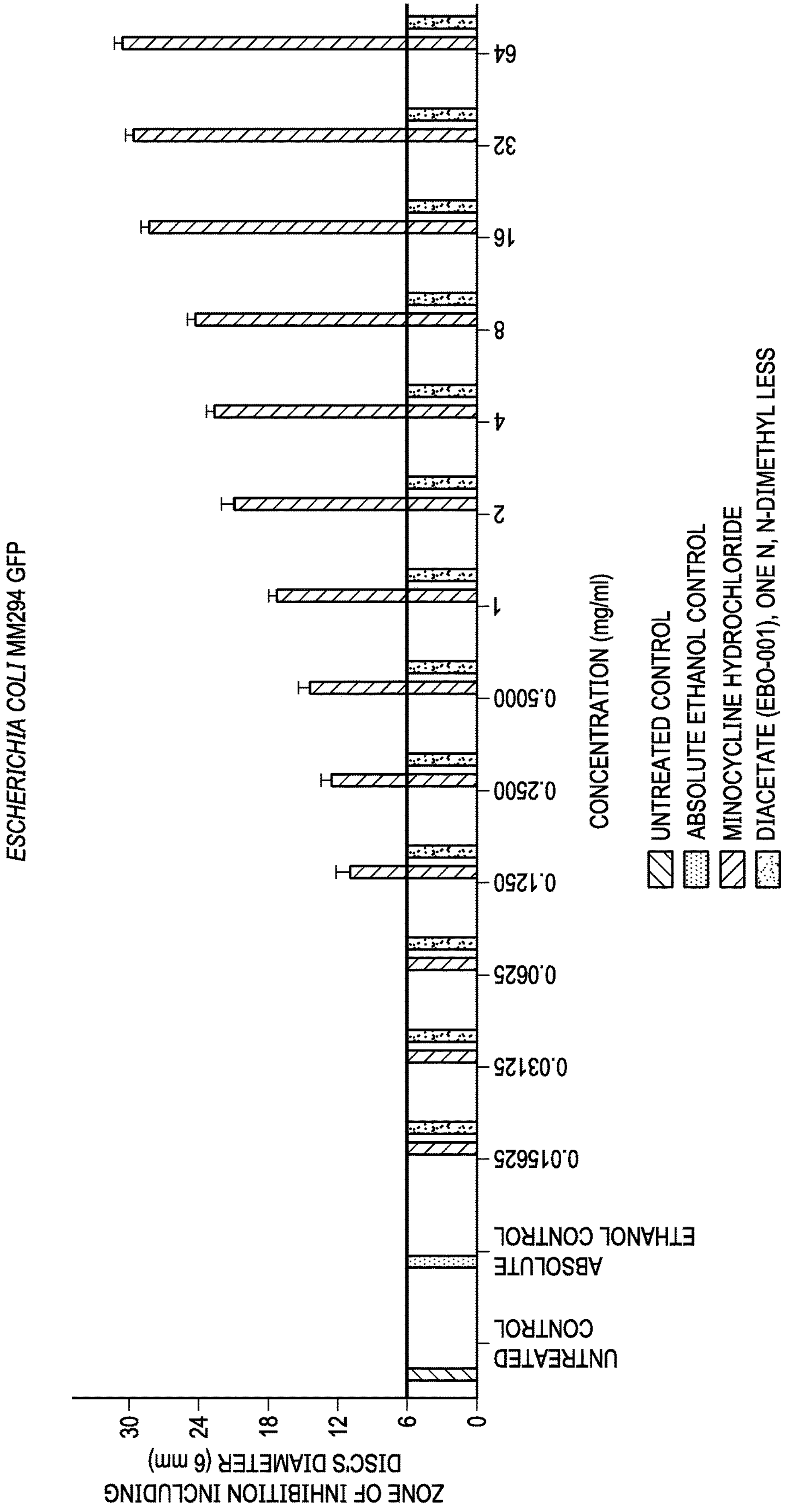
FIGS. 12A to 12C show the activity of De Methyl Diacetate Minocycline (Acetic acid 9-acetylcarbamoyl-4-dimethylamino-8,10,11-trihydroxy-12-oxo-5,5a,6,12-tetra-hydro-naphthacen-1-yl ester), as shown with FIG. 12A *E. coli* MM294 GFP zone of inhibition, FIG. 12B *E. coli* MM294 GFP CFU/disc, and FIG. 12C reduction of binge ethanol consumption.
Figure 12B:
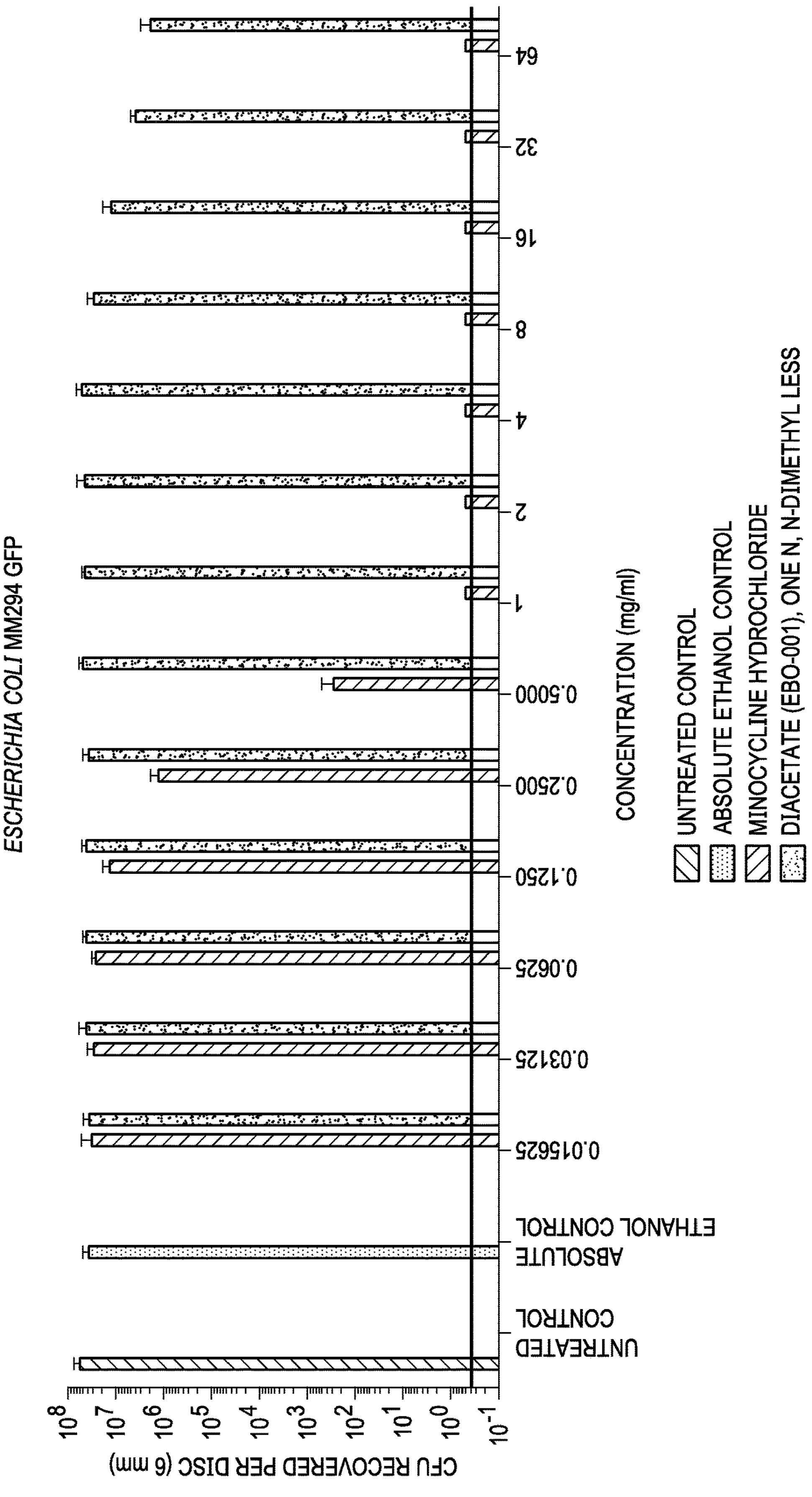
Figure 12C:
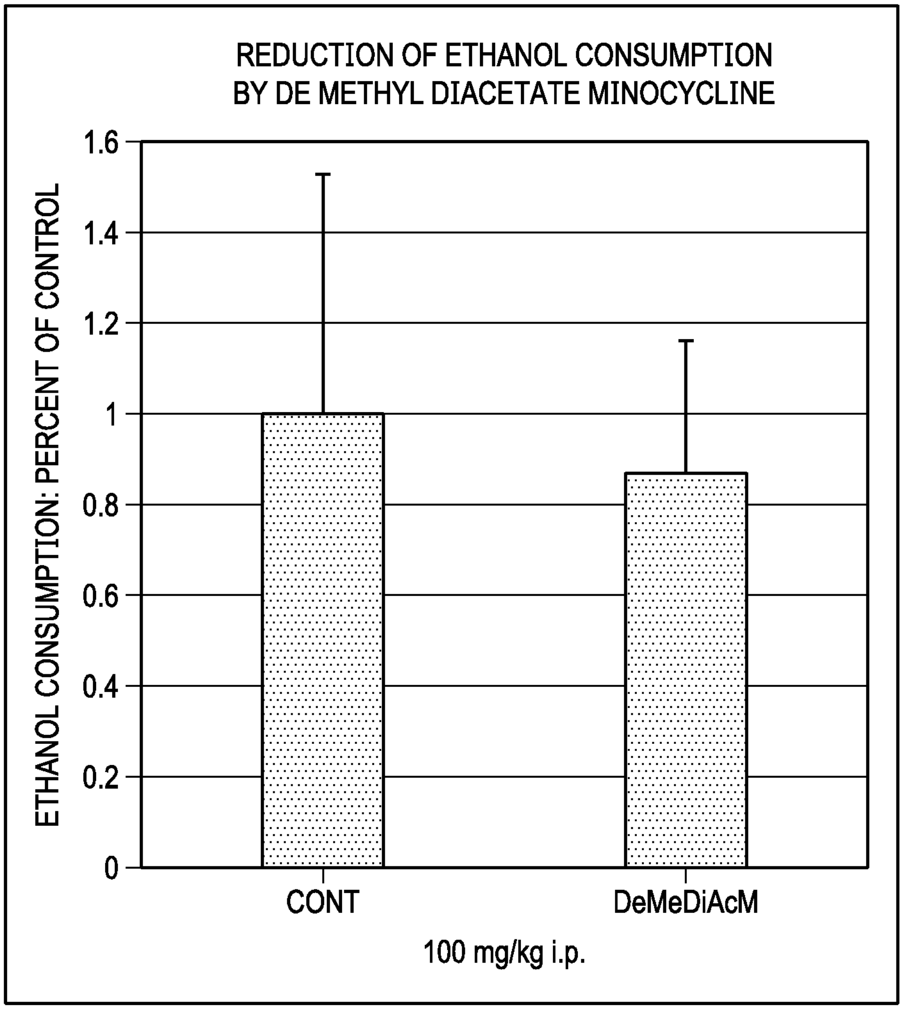

FIGS. 12A to 12C show the activity of De Methyl Diacetate Minocycline (Acetic acid 9-acetylcarbamoyl-4-dimethylamino-8,10,11-trihydroxy-12-oxo-5,5a,6,12-tetrahydro-naphthacen-1-yl ester), as shown with FIG. 12A *E. coli* MM294 GFP zone of inhibition, FIG. 12B *E. coli* MM294 GFP CFU/disc, and FIG. 12C reduction of binge ethanol consumption.

Figure 13A:
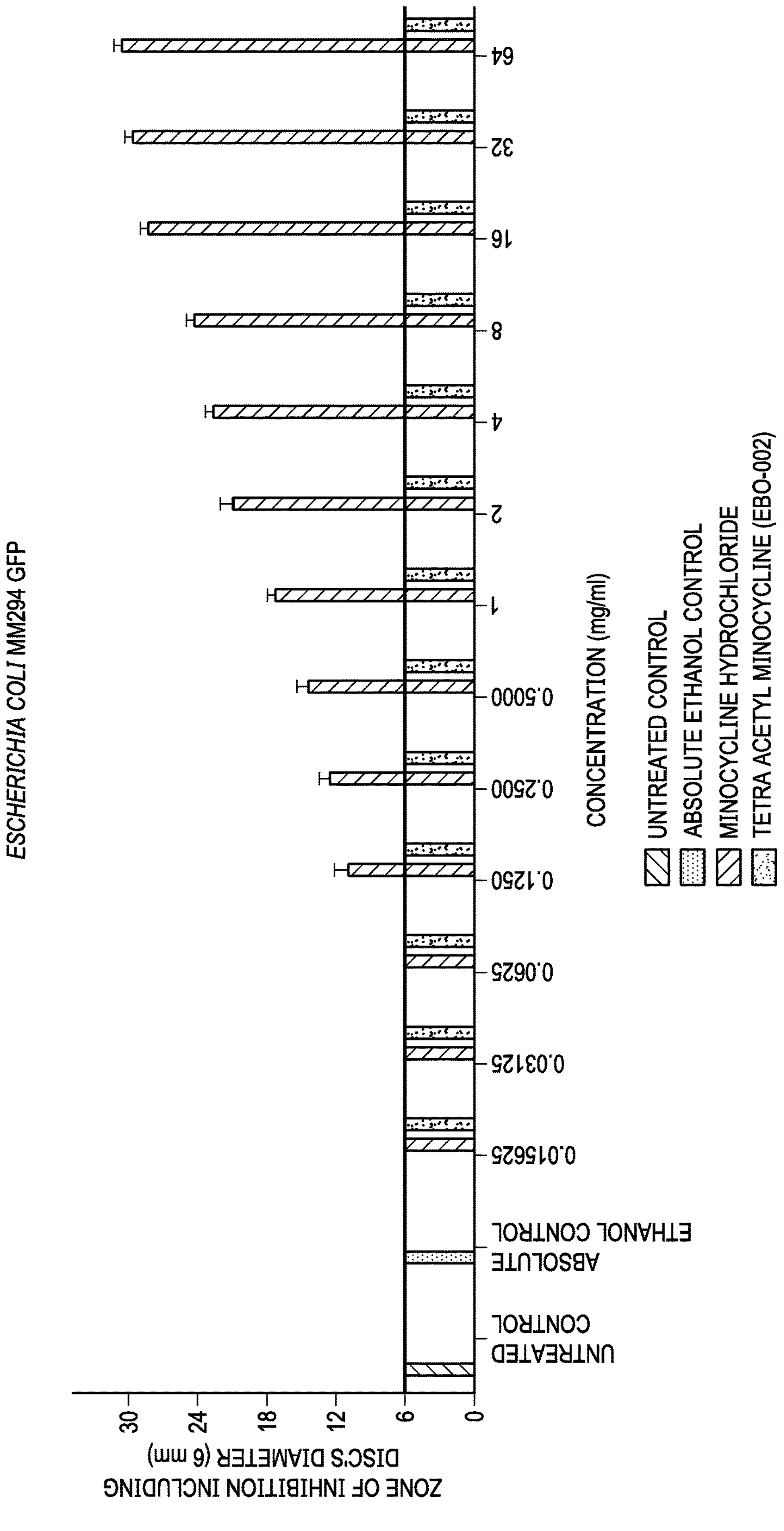
FIGS. 13A to 13C show the activity of Tetra Acetyl Minocycline (Acetic acid 3,10-diacetoxy-2-acetylcarbamoyl-4,7-bis-dimethylamino-12-hydroxy-11-oxo-5,5a,6,11-tetrahydro-naphthacen-1-yl ester), as shown with FIG. 13A *E. coli* MM294 GFP zone of inhibition, FIG. 13B *E. coli* MM294 GFP CFU/disc, and FIG. 13C reduction of binge ethanol consumption.
Figure 13B:
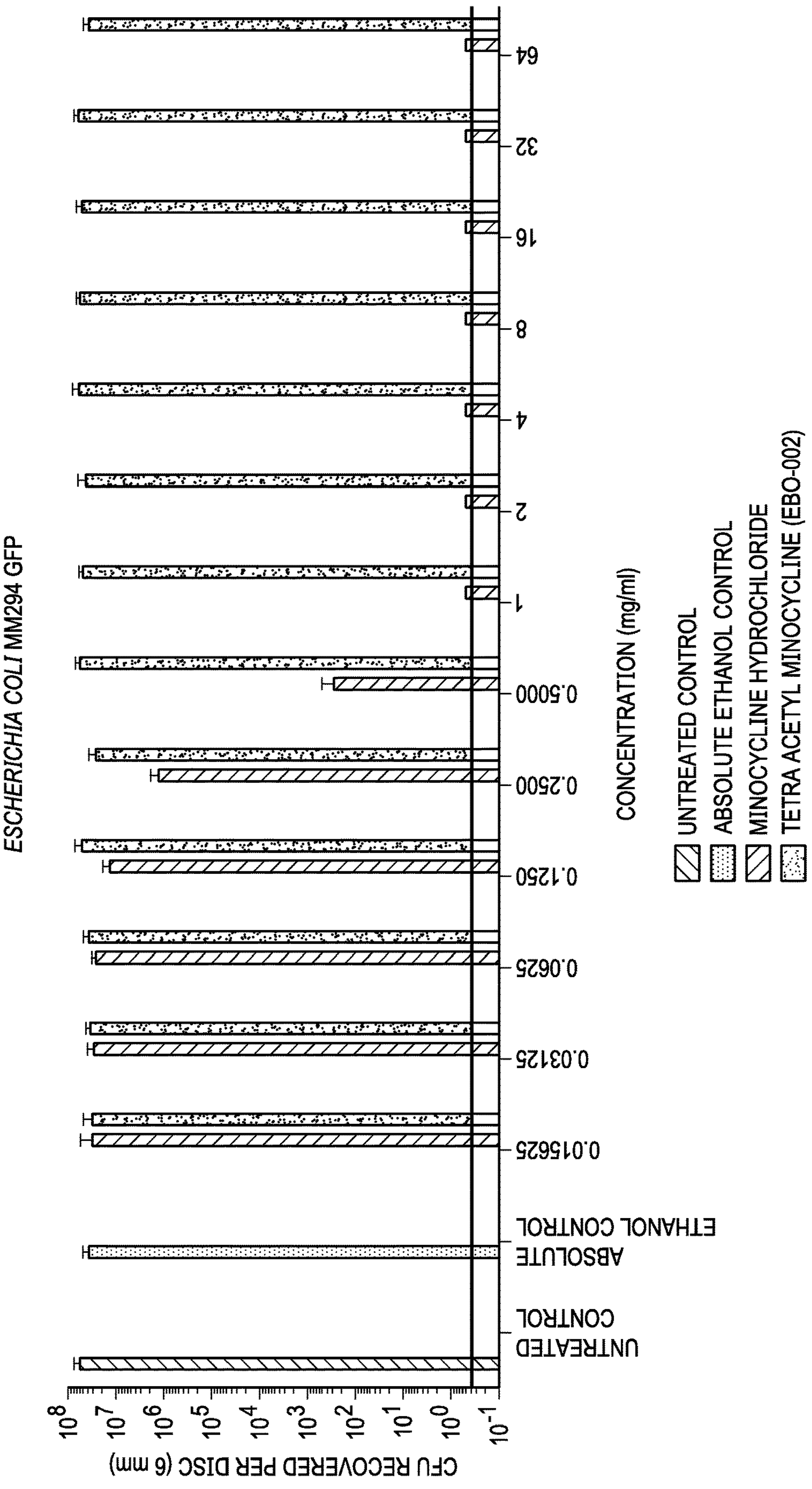
Figure 13C:
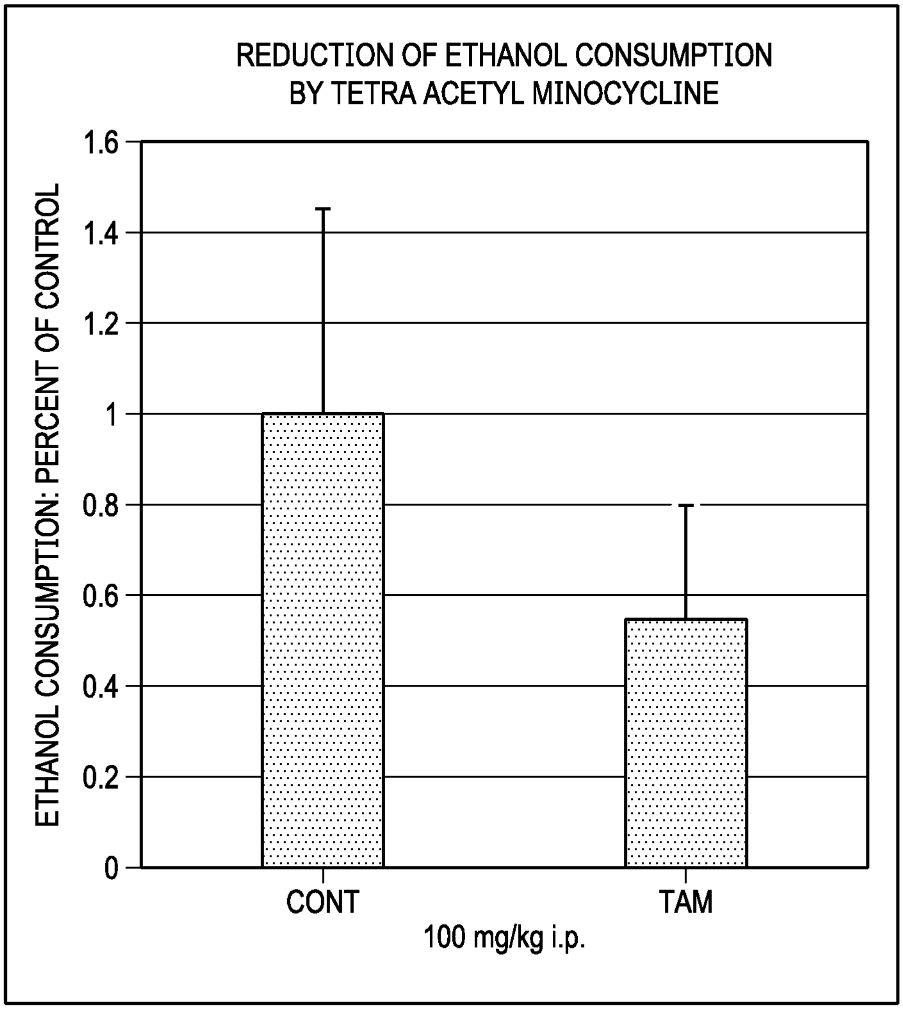

FIGS. 13A to 13C show the activity of Tetra Acetyl Minocycline (Acetic acid 3,10-diacetoxy-2-acetylcarbamoyl-4,7-bis-dimethylamino-12-hydroxy-11-oxo-5,5a,6,11-tetrahydro-naphthacen-1-yl ester), as shown with FIG. 13A *E. coli* MM294 GFP zone of inhibition, FIG. 13B *E. coli* MM294 GFP CFU/disc, and FIG. 13C reduction of binge ethanol consumption.

Figure 14A:
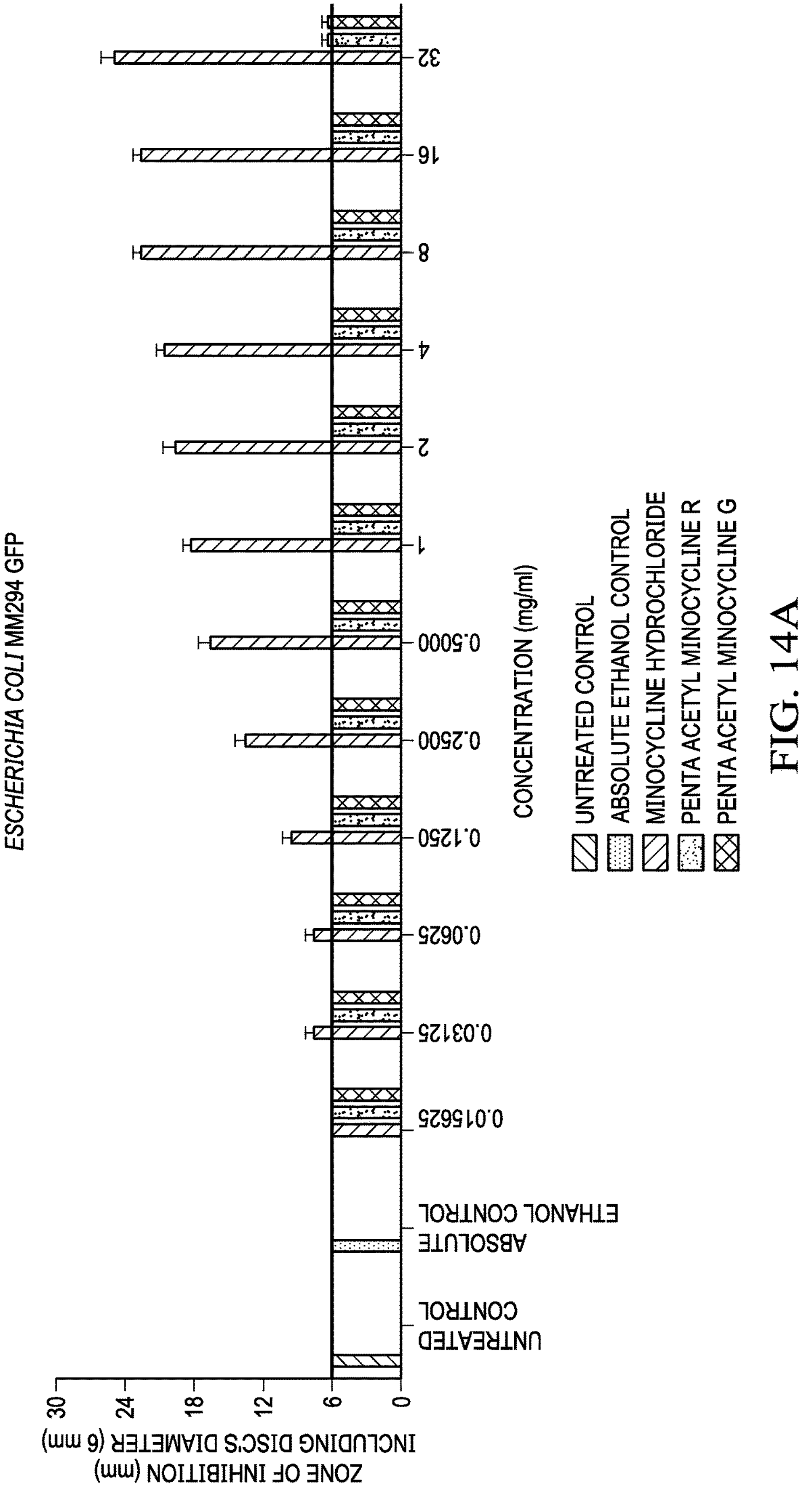
FIGS. 14A to 14C show the activity of Penta Acetyl Minocycline (Acetic acid 3,10,12-triacetoxy-2-acetylcarbamoyl-4,7-bis-dimethylamino-11-oxo-5,5a,6,11-tetra-hydro-naphthacen-1-yl ester), as shown with FIG. 14A *E. coli* MM294 GFP zone of inhibition, FIG. 14B *E. coli* MM294 GFP CFU/disc, and FIG. 14C reduction of binge ethanol consumption.
Figure 14B:
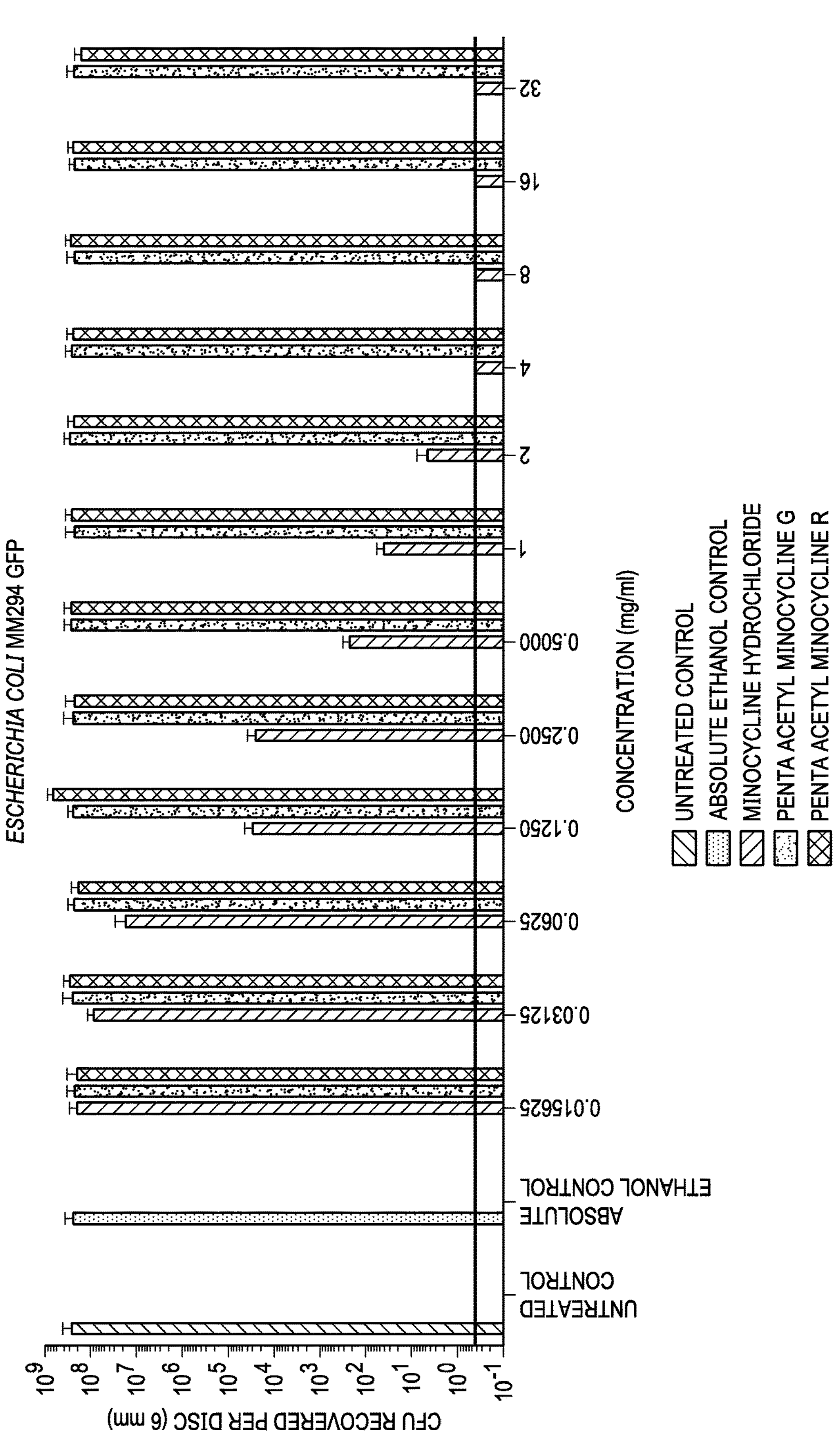
Figure 14C:
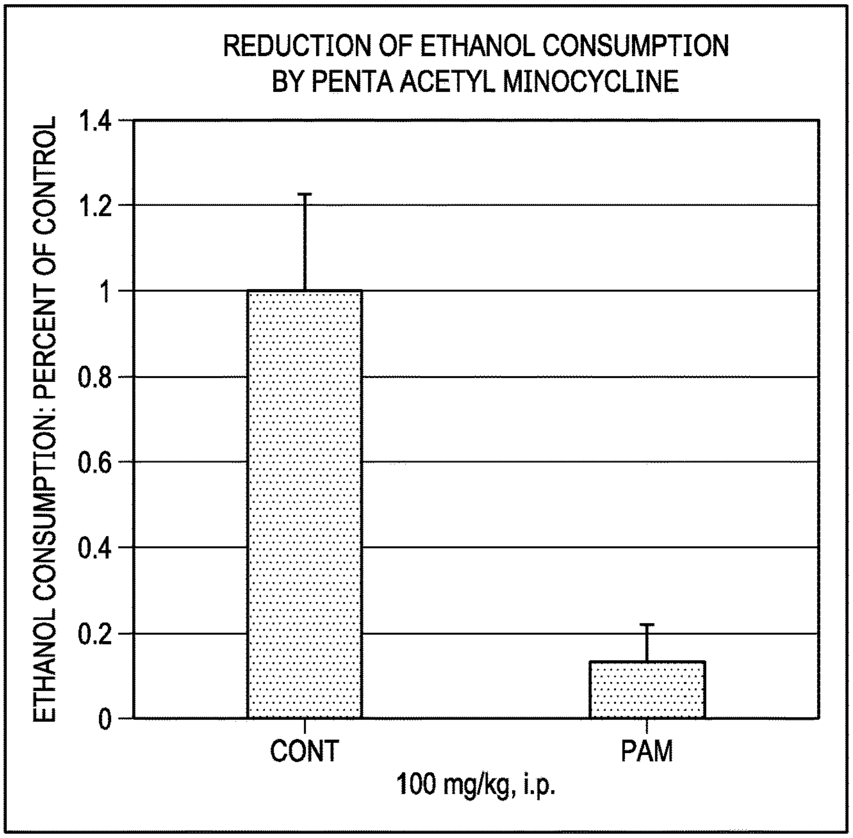

FIGS. 14A to 14C show the activity of Penta Acetyl Minocycline (Acetic acid 3,10,12-triacetoxy-2-acetylcarbamoyl-4,7-bis-dimethylamino-11-oxo-5,5a,6,11-tetra-hydro-naphthacen-1-yl ester), as shown with FIG. 14A *E. coli* MM294 GFP zone of inhibition, FIG. 14B *E. coli* MM294 GFP CFU/disc, and FIG. 14C reduction of binge ethanol consumption.

Figure 15A:
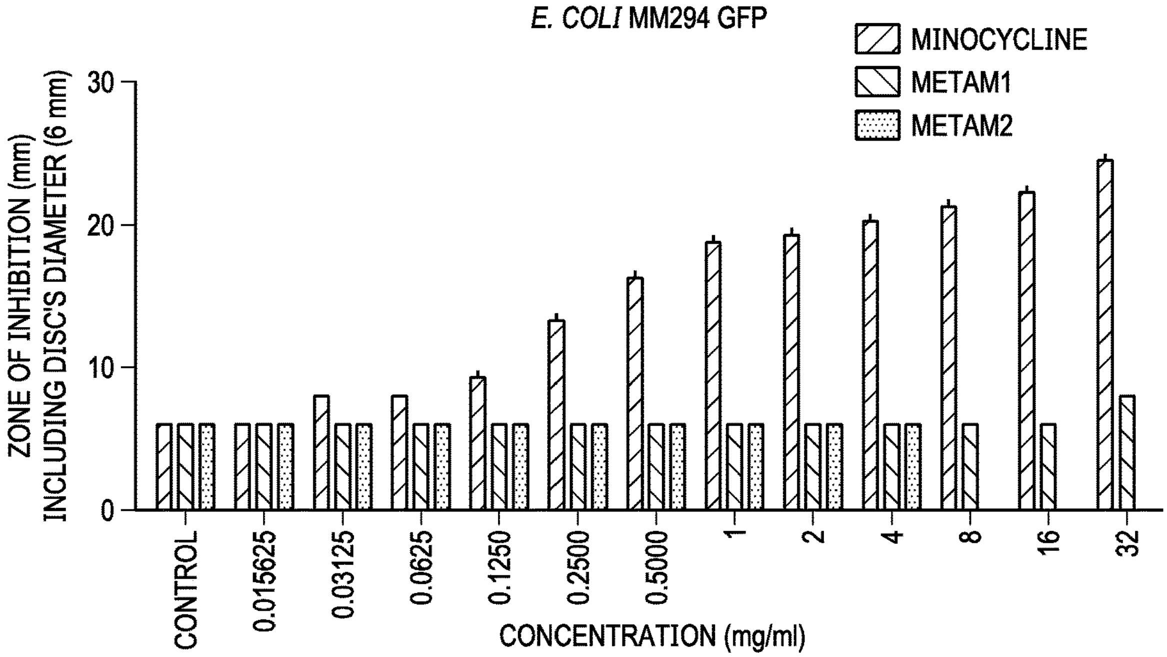
FIGS. 15A to 15C show the activity of Methyl Ether N-Monoacetate Minocycline (4,7-Bis-dimethylamino-1,3,12-trihydroxy-10-methoxy-11-oxo-5,5a,6,11-tetrahydro-naphthacene-2-carboxylic acid acetyl-amide) and Methyl Ether Tri Acetate Minocycline (Acetic acid 4-acetoxy-3-acetylcarbamoyl-1,10-bis-dimethylamino-5-hydroxy-7-methoxy-6-oxo-6,11,11a,12-tetrahydro-naphthacen-2-yl ester), as shown with FIG. 15A *E. coli* MM294 GFP zone of inhibition, FIG. 15B *E. coli* MM294 GFP CFU/disc, and FIG. 15C reduction of binge ethanol consumption.
Figure 15B:
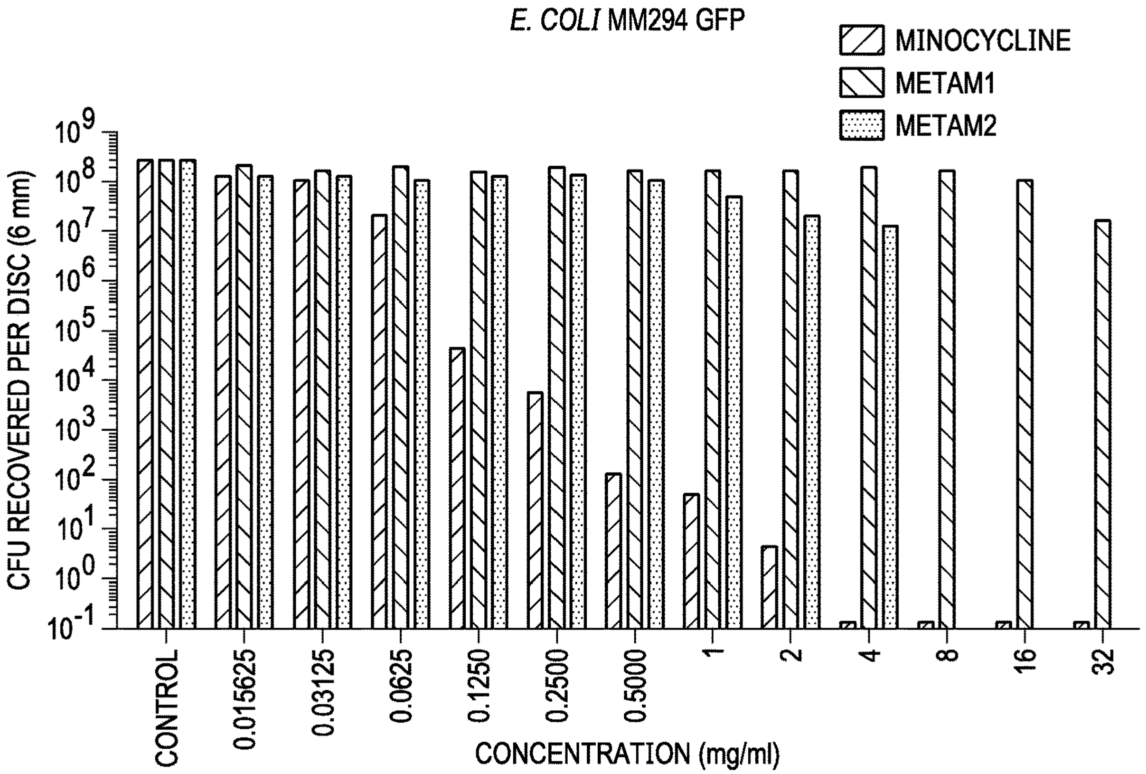
Figure 15C:
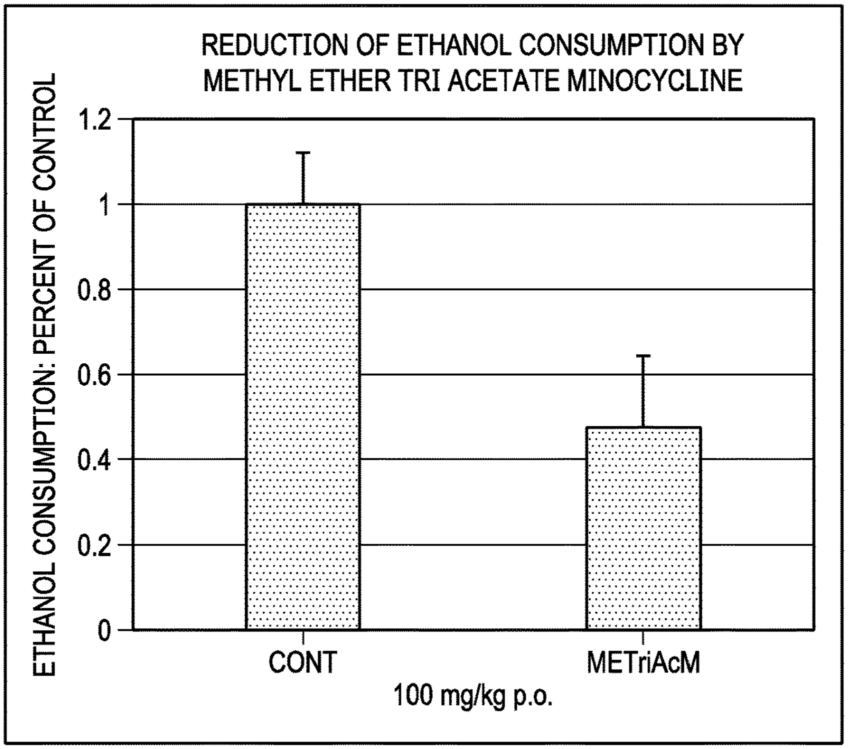

FIGS. 15A to 15C show the activity of Methyl Ether N-Monoacetate Minocycline (4,7-Bis-dimethylamino-1,3,12-trihydroxy-10-methoxy-11-oxo-5,5a,6,11-tetrahydro-naphthacene-2-carboxylic acid acetyl-amide) and Methyl Ether Tri Acetate Minocycline (Acetic acid 4-acetoxy-3-acetylcarbamoyl-1,10-bis-dimethylamino-5-hydroxy-7-methoxy-6-oxo-6,11,11a,12-tetrahydro-naphthacen-2-yl ester), as shown with FIG. 15A *E. coli* MM294 GFP zone of inhibition, FIG. 15B *E. coli* MM294 GFP CFU/disc, and FIG. 15C reduction of binge ethanol consumption.

Acetylated tetracycline with a hydrogen R-group at R6' has a loss of antibiotic properties with retention of the ability to reduce alcohol consumption in mice. These data demonstrate that that, in addition to acetylated minocycline, the modification effects also extend to doxycycline and tigecycline. Specifically, the present invention includes any modification that removes the ability of the tetracycline class molecules to bind to the bacterial ribosome, with retention of anti-AUD or SUD activity or an innate immune modulatory function. The traits include, but are not limited to: reduction of alcohol consumption (both binge and dependence related drinking), suppression of alcohol withdrawal symptoms, relief of alcohol-mediated pain and emotional distress.

Examples of salts that may be used with the compounds of the present invention include: sulfate, citrate, acetate, oxalate, chloride, bromide, iodide, nitrate, besylate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and/or pamoate.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), property(ies), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skill in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

To aid the Patent Office, and any readers of any patent issued on this application in interpreting the claims appended hereto, applicants wish to note that they do not intend any of the appended claims to invoke paragraph 6 of 35 U.S.C. § 112, U.S.C. § 112 paragraph (f), or equivalent, as it exists on the date of filing hereof unless the words “means for” or “step for” are explicitly used in the particular claim.

For each of the claims, each dependent claim can depend both from the independent claim and from each of the prior dependent claims for each and every claim so long as the prior claim provides a proper antecedent basis for a claim term or element.

REFERENCES

Agrawal, R. G., A. Hewetson, C. M. George, P. J. Syapin, and S. E. Bergeson. 2011. ‘Minocycline reduces ethanol drinking’, Brain, behavior, and immunity, 25 Suppl 1: S165-9.

Agrawal, R. G., J. A. Owen, P. S. Levin, A. Hewetson, A. E. Berman, S. R. Franklin, R. J. Hogue, Y. Chen, C. Walz, B. D. Colvard, J. Nguyen, O. Velasquez, Y. Al-Hasan, Y. A. Blednov, A. K. Fowler, P. J. Syapin, and S. E. Bergeson. 2014. ‘Bioinformatics analyses reveal age-specific neuroimmune modulation as a target for treatment of high ethanol drinking’, Alcoholism, clinical and experimental research, 38: 428-37.

Bergeson, S. E., H. Blanton, J. M. Martinez, D. C. Curtis, C. Sherfey, B. Seegmiller, P. C. Marquardt, J. A. Groot, C. L. Allison, C. Bezboruah, and J. Guindon. 2016. ‘Binge Ethanol Consumption Increases Inflammatory Pain Responses and Mechanical and Cold Sensitivity: Tigecycline Treatment Efficacy Shows Sex Differences’, Alcoholism, clinical and experimental research, 40: 2506-15.

Bergeson, S. E., M. A. Nipper, J. Jensen, M. L. Helms, and D. A. Finn. 2016. ‘Tigecycline Reduces Ethanol Intake in Dependent and Nondependent Male and Female C57BL/6J Mice’, Alcoholism, clinical and experimental research, 40: 2491-98.

Blednov, Y. A., J. M. Benavidez, C. Geil, S. Perra, H. Morikawa, and R. A. Harris. 2011. ‘Activation of inflammatory signaling by lipopolysaccharide produces a prolonged increase of voluntary alcohol intake in mice’, Brain, behavior, and immunity, 25 Suppl 1: S92-S105.

Martinez, J. M., J. A. Groot, D. C. Curtis, C. L. Allison, P. C. Marquardt, A. N. Holmes, D. S. Edwards, D. R. Trotter, P. J. Syapin, D. A. Finn, and S. E. Bergeson. 2016. ‘Effective Reduction of Acute Ethanol Withdrawal by the Tetracycline Derivative, Tigecycline, in Female and Male DBA/2J Mice’, Alcoholism, clinical and experimental research, 40: 2499-505.

Montesinos, J., S. Alfonso-Loeches, and C. Guerri. 2016. ‘Impact of the Innate Immune Response in the Actions of Ethanol on the Central Nervous System’, Alcoholism, clinical and experimental research, 40: 2260-70.

Rhodes, J. S., K. Best, J. K. Belknap, D. A. Finn, and J. C. Crabbe. 2005. ‘Evaluation of a simple model of ethanol drinking to intoxication in C57BL/6J mice’, Physiology & Behavior, 84: 53-63.

Schedlbauer, A., T. Kaminishi, B. Ochoa-Lizarralde, N. Dhimole, S. Zhou, J. P. Lopez-Alonso, S. R. Connell, and P. Fucini. 2015. ‘Structural characterization of an alternative mode of tigecycline binding to the bacterial ribosome’, Antimicrobial agents and chemotherapy, 59: 2849-54.

Syapin, P. J., J. M. Martinez, D. C. Curtis, P. C. Marquardt, C. L. Allison, J. A. Groot, C. Baby, Y. M. Al-Hasan, I. Segura-Ulate, M. J. Scheible, K. T. Nicholson, J. L. Redondo, D. R. Trotter, D. S. Edwards, and S. E. Bergeson. 2016. ‘Effective Reduction in High Ethanol Drinking by Semisynthetic Tetracycline Derivatives’, Alcoholism, clinical and experimental research, 40: 2482-90.

What is claimed is:

1. A modified tetracycline molecule, pharmaceutically acceptable salts, biologically active metabolites, and tautomers thereof selected from the formulas 1 to 71, and 74 to 78 and 80 to 85:

1.

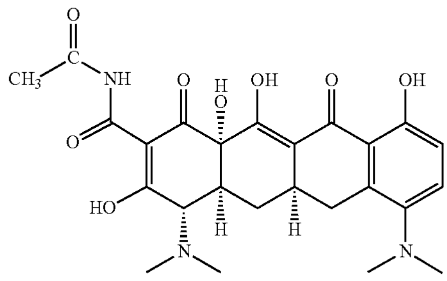

;

2.

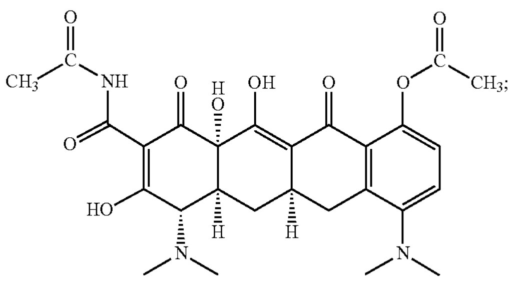

;

3.

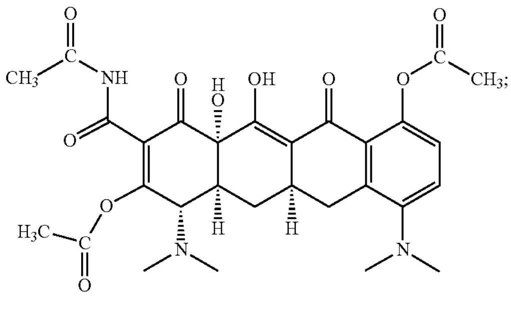

;

4.

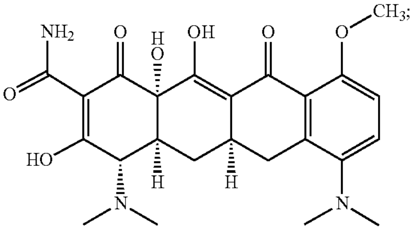

;

-continued
5.
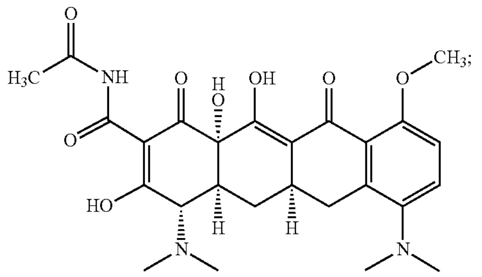
6.
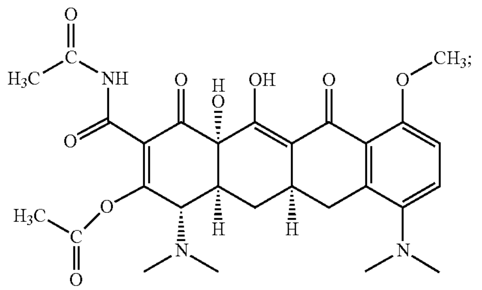
7.
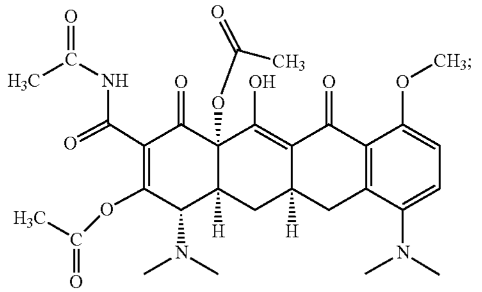
8.
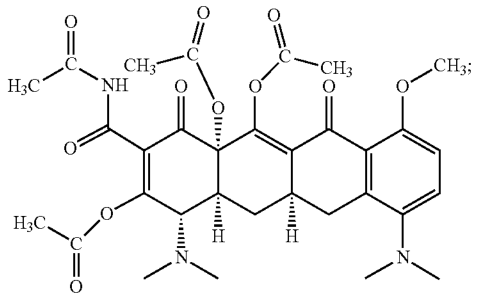
9.
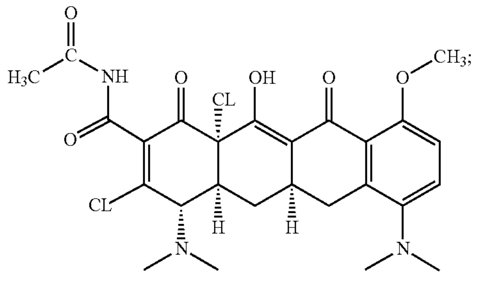
-continued
10.
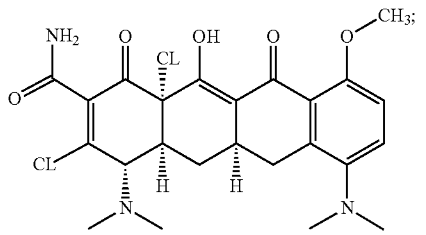
11.
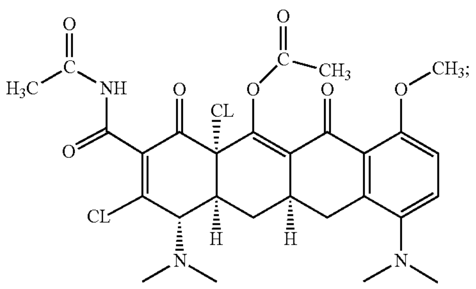
12.
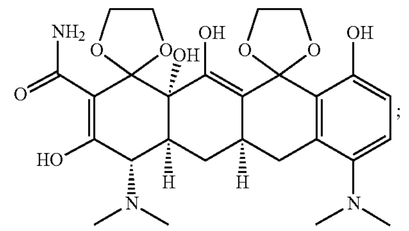
13.
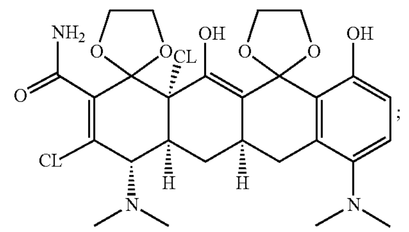
14.
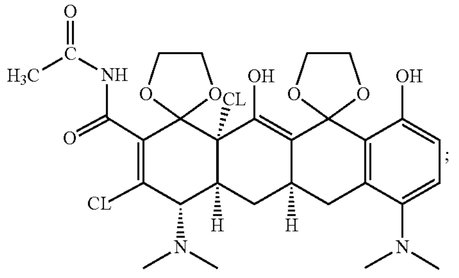
15.
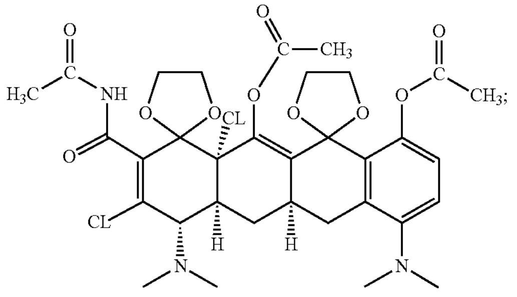

-continued
16.
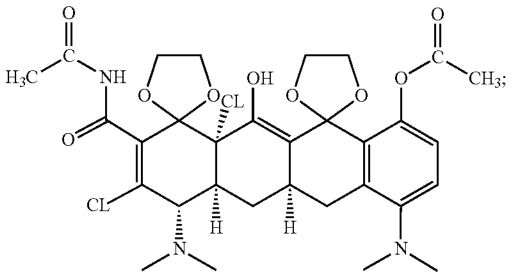
17.
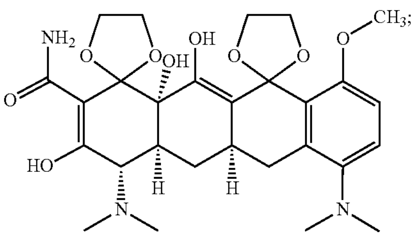
18.
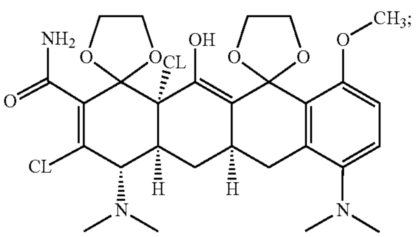
19.
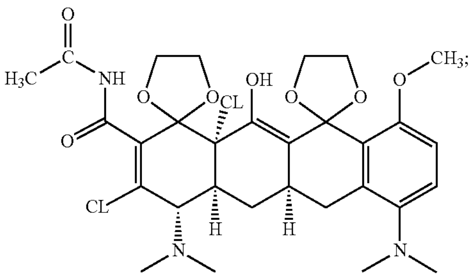
20.
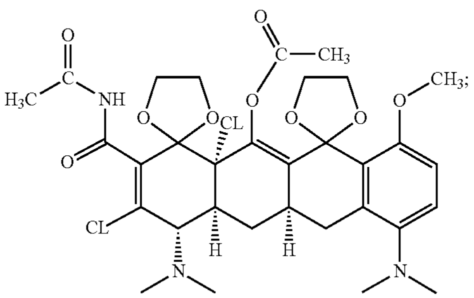
-continued
21.
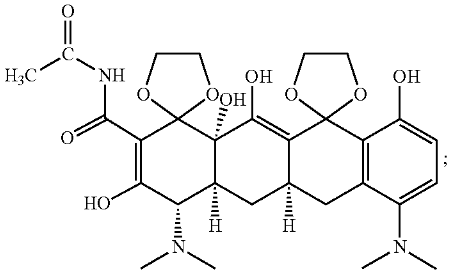
22.
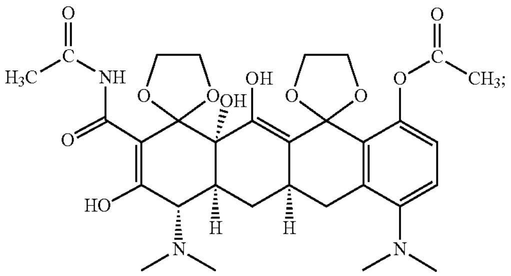
23.
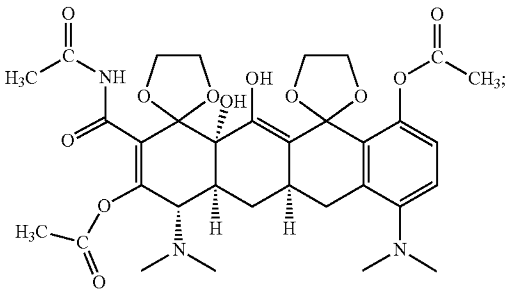
24.
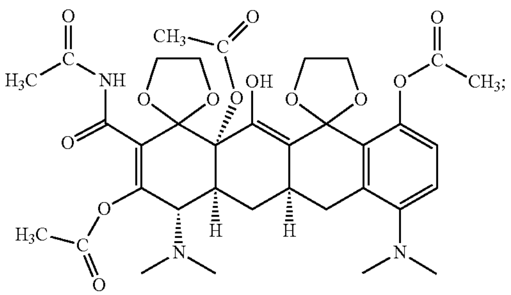
25.
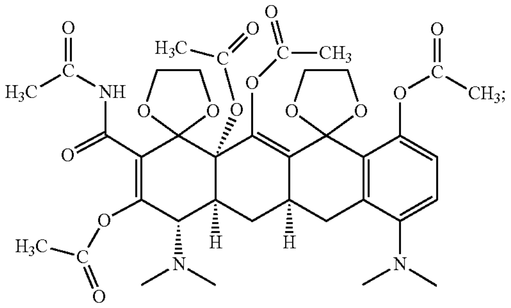

-continued
26.
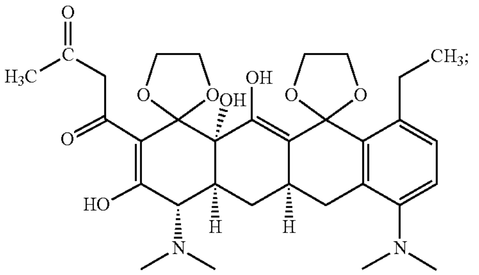
27.
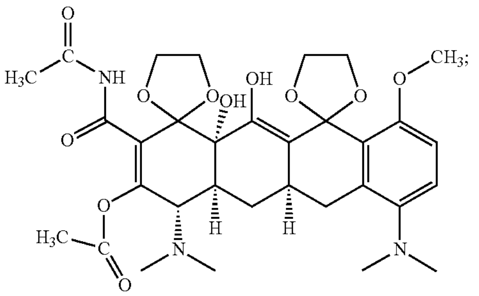
28.
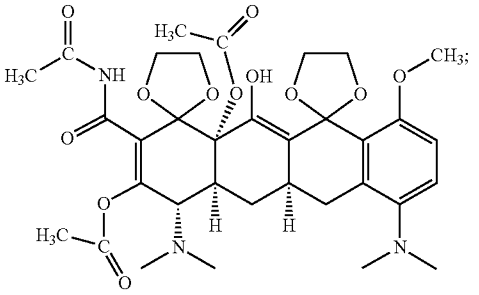
29.
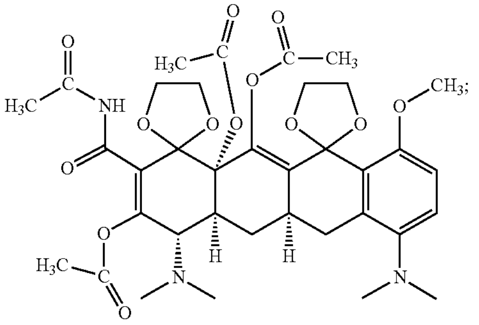
30.
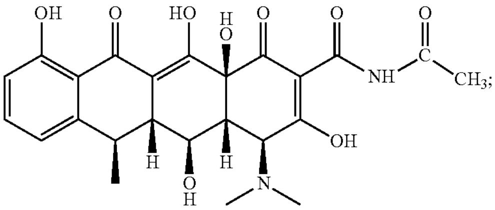
-continued
31.
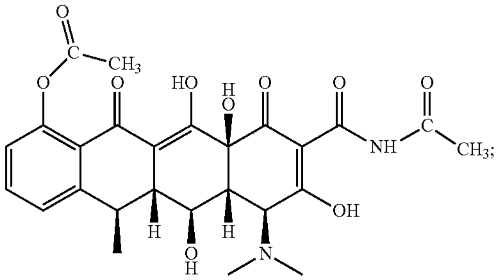
32.
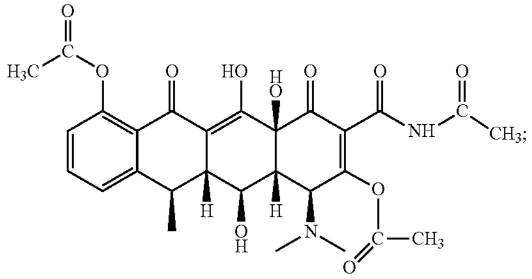
33.
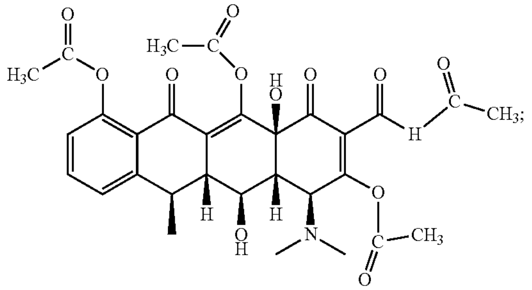
34.
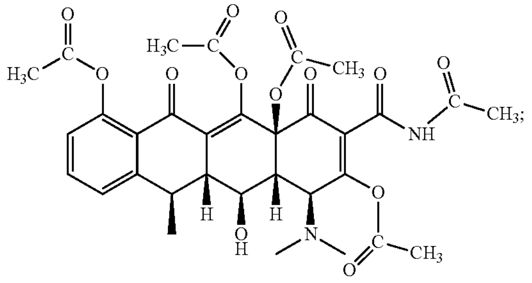
35.
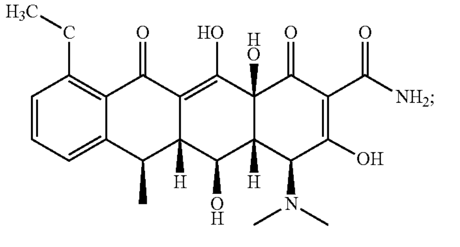
36.
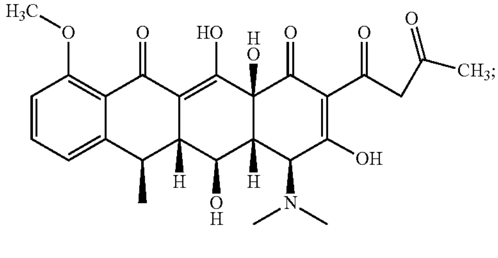

-continued
37.
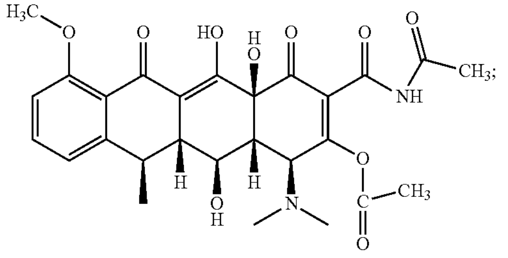
38.
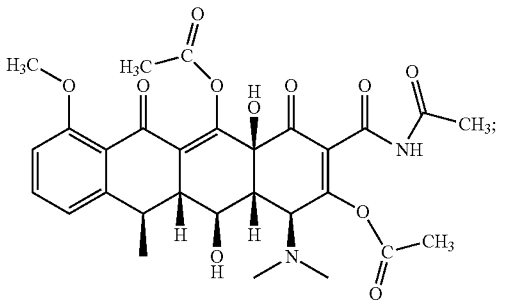
39.
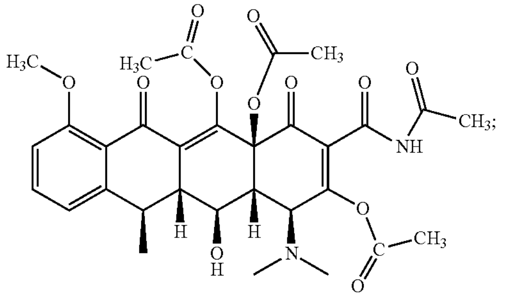
40.
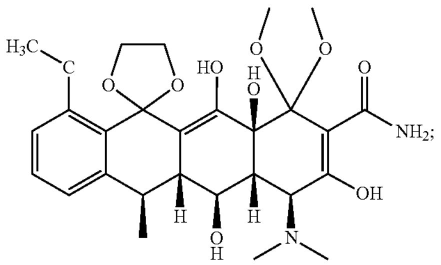
41.
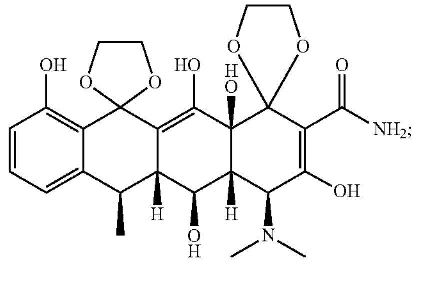
-continued
42.
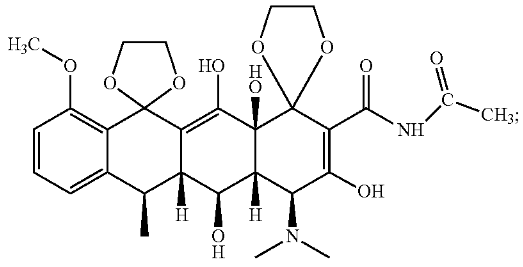
43.
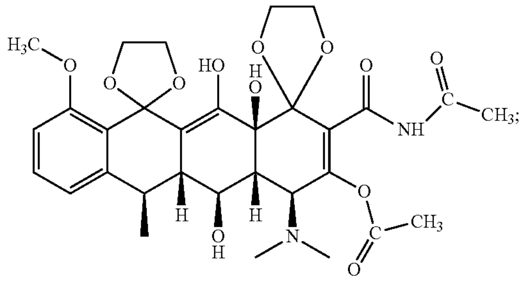
44.
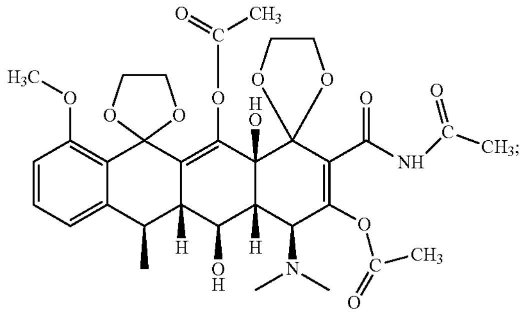
45.
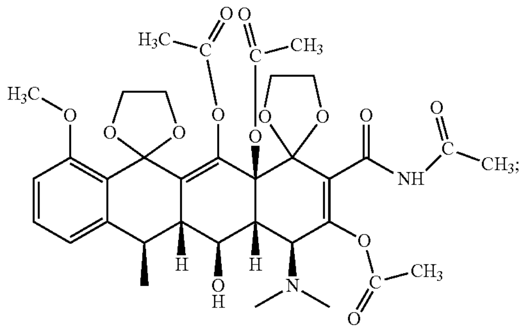
46.
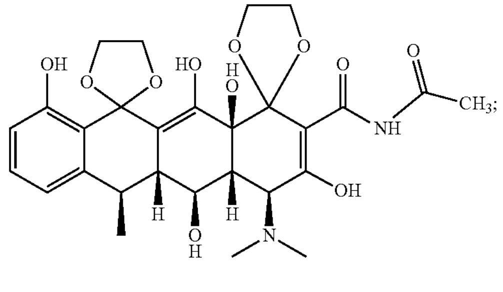

-continued
47.
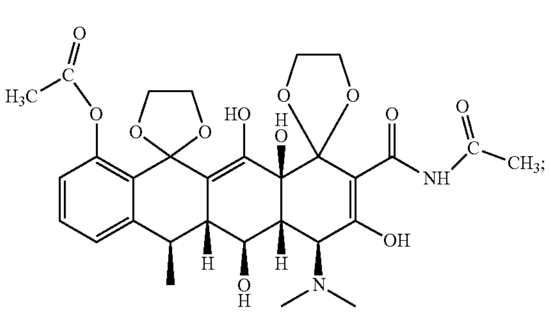
48.
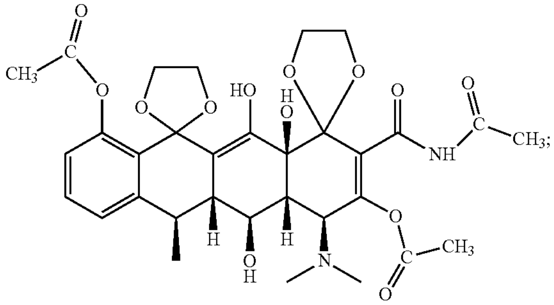
49.
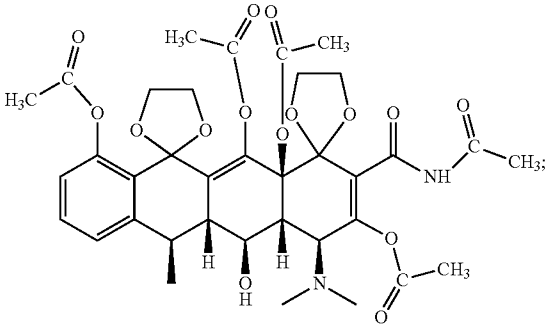
50.
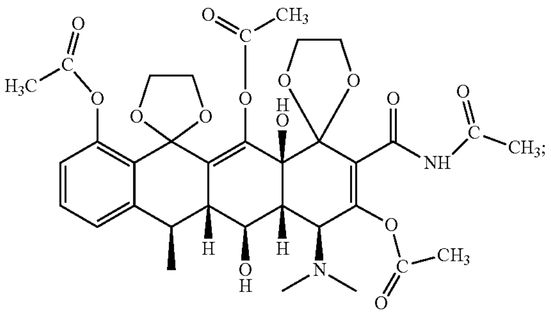
51.
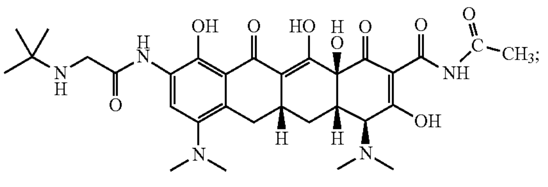
-continued
52.
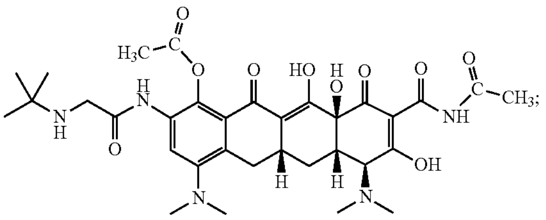
53.
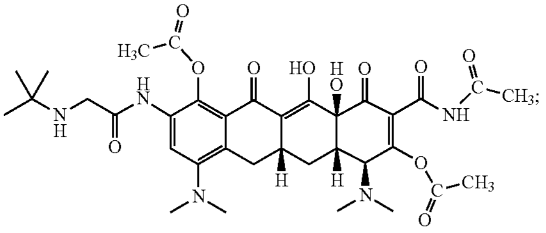
54.
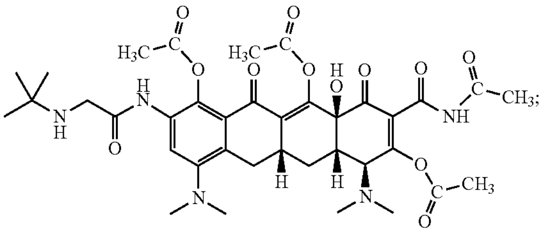
55.
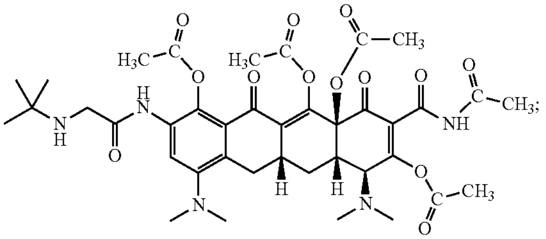
56.
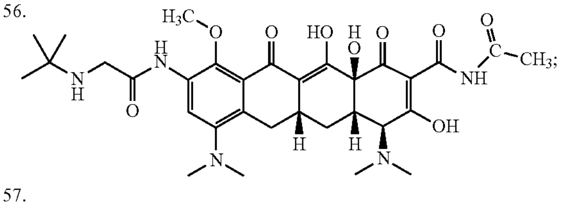
57.
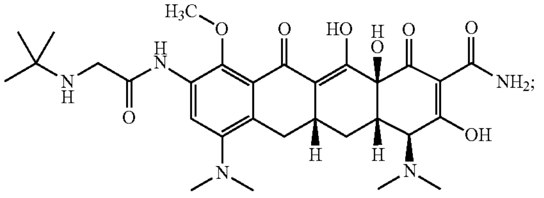
58.
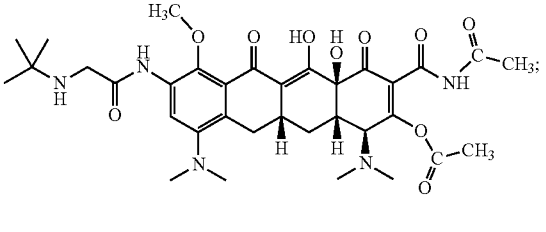

-continued
59.
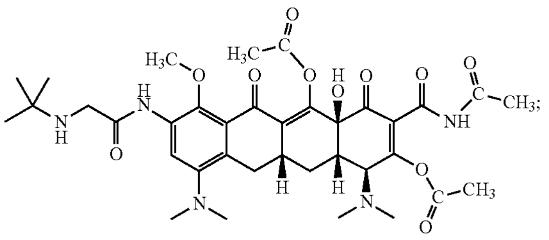
60.
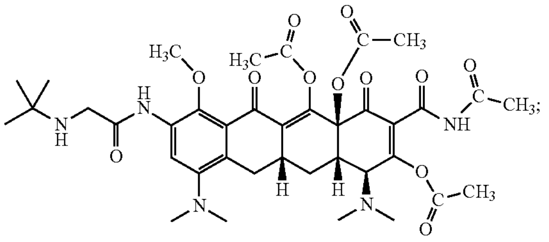
61.
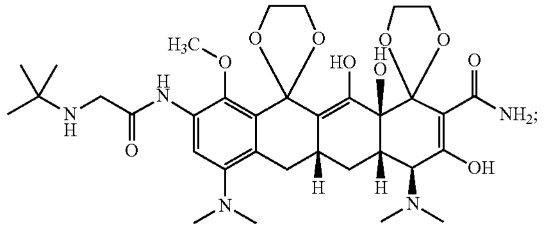
62.
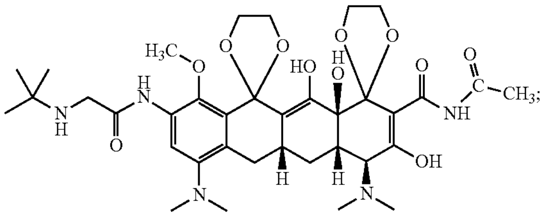
63.
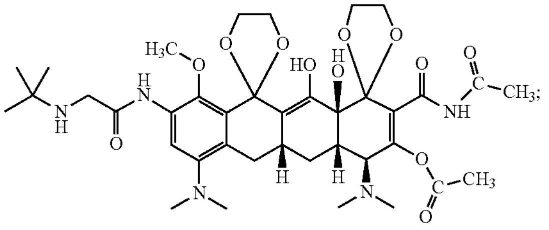
64.
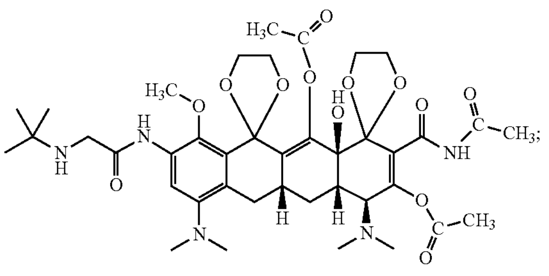
-continued
65.
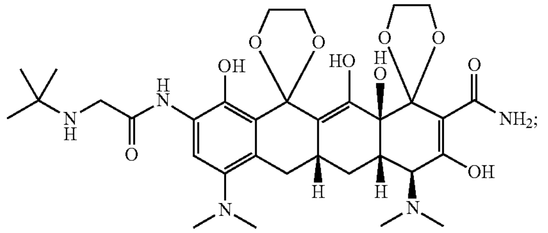
66.
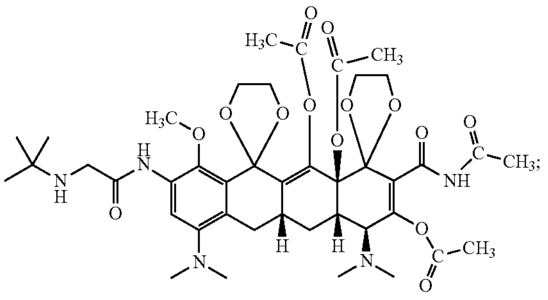
67.
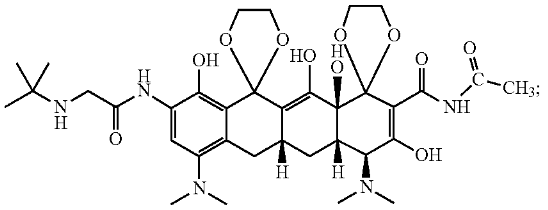
68.
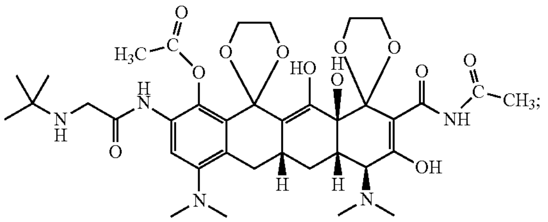
69.
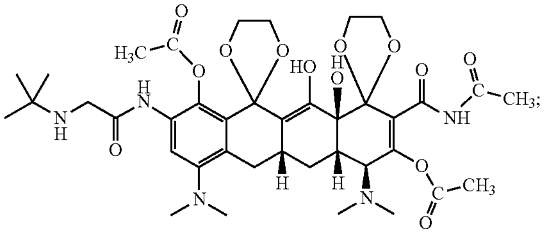
70.
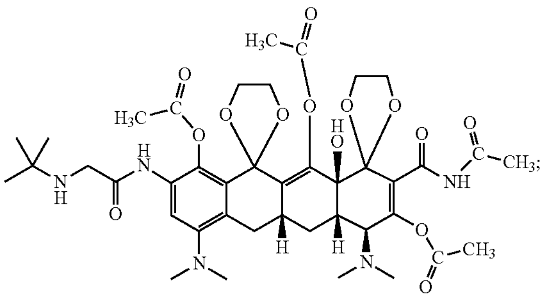

-continued

71.

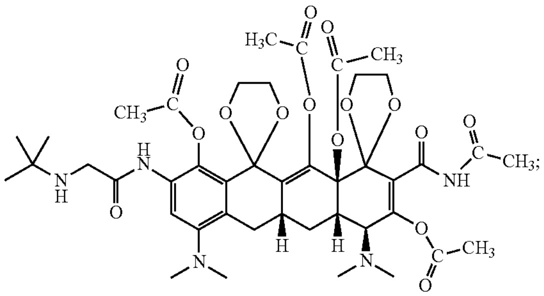

74.

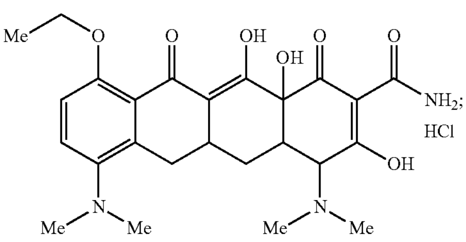

75.

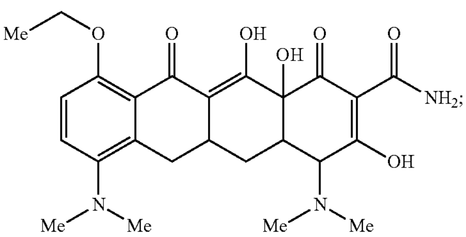

76.

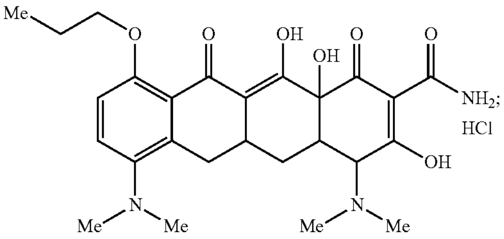

77.

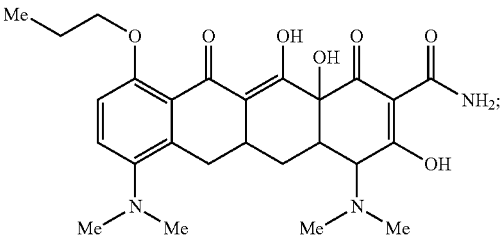

78.

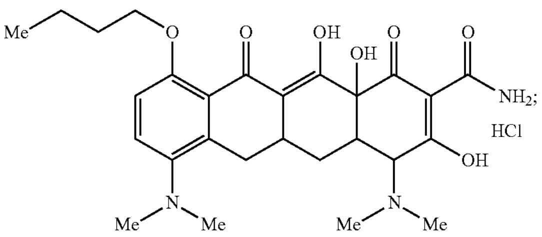

-continued

80.

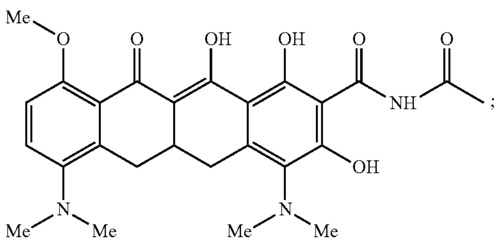

81.

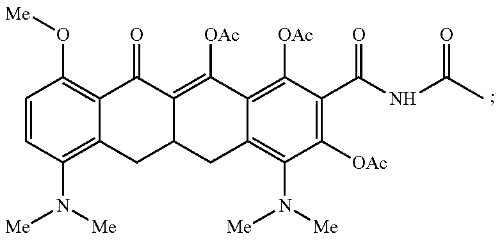

82.

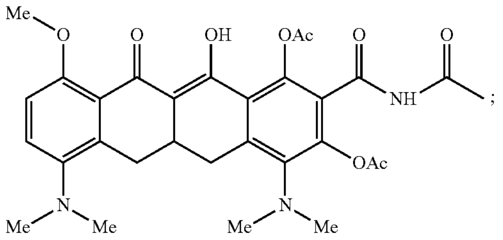

85.

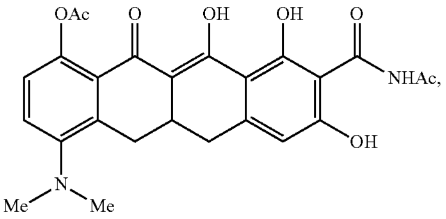

wherein the doxycycline, minocycline, and tigecycline structures are modified to prevent binding of the molecule to a ribosome; and a pharmaceutically acceptable salt, buffer, excipient, filler, or carrier.

2. The molecule of claim 1, wherein the molecule has a least one of: reduced or substantially no antibacterial activity, or reduced or substantially no antifungal activity, or both.

3. The molecule of claim 1, wherein the molecule is provided in an amount that at least one of: inhibits Alcohol Use Disorder (AUD), Substance Use Disorder (SUD), tobacco use, or pain and disorders involving potential inflammatory processes.

4. The molecule of claim 1, wherein the modification at least one of: produces steric hindrance, blocks hydrogen bonding, or charge coordination with divalent cations.

5. The molecule of claim 1, wherein the compound is formulated for administration orally, enterally, intramuscularly, parenterally, intravenously, or intraperitoneally.

6. A pharmaceutical composition comprising a compound of claim 1, pharmaceutically acceptable salts, biologically active metabolites, and tautomers thereof.

7. A method of treating Substance Use Disorder (SUD) comprising:

providing the subject with an effective amount of one or more modified tetracyclines of Formula 1 to 71, 74 to 78 and 80 to 85 of claim 1 to ameliorate or eliminate the SUD with reduced, or no, antimicrobial activity.

8. The method of claim 7, wherein the one or more modified tetracyclines has a least one of: reduced or substantially no antibacterial activity, or reduced or substantially no antifungal activity, or both.

9. The method of claim 7, wherein the modification at least one of: produces steric hindrance, blocks hydrogen bonding, or charge coordination with divalent cations.

10. The method of claim 7, further comprising providing the one or more modified tetracyclines in a pharmaceutically acceptable buffer, excipient, filler, or carrier or wherein the one or more modified tetracyclines is formulated for administration orally, enterally, intramuscularly, parenterally, intravenously, or intraperitoneally, or both.

11. A method of treating Substance Use Disorder (SUD), comprising:

identifying a subject in need of treatment for the SUD; and providing the subject with an effective amount of one or more modified tetracyclines of Formula 1 to 71, 74 to 78 and 80 to 85 of claim 1 to ameliorate or eliminate the SUD with reduced, or no, antimicrobial activity.

12. The method of claim 11, wherein the molecule has a least one of: no antibacterial activity, or no antifungal activity, or both.

13. The method of claim 11, wherein the modified molecule is a doxycycline, minocycline, or tigecycline or their tautomeric structures.

14. The method of claim 11, wherein the modification at least one of: produces steric hindrance, blocks hydrogen bonding, or charge coordination with divalent cations.

15. The method of claim 11, further comprising providing the molecule in a pharmaceutically acceptable buffer, excipient, filler, or carrier or wherein the molecule is formulated for administration orally, enterally, intramuscularly, parenterally, intravenously, or intraperitoneally, or both.

16. A method of evaluating a candidate drug believed to be useful in treating Substance Use Disorder (SUD), the method comprising:

a) measuring the SUD from a set of patients;

b) administering a candidate drug to a first subset of the patients, and a placebo to a second subset of the patients, wherein the candidate drug is Formula 1 to 71, 74 to 78 and 80 to 85 of claim 1;

c) repeating step a) after the administration of the candidate drug or the placebo; and d) determining if the candidate drug reduces the SUD that is statistically significant as compared to any reduction occurring in the second subset of patients, wherein a statistically significant reduction indicates that the candidate drug is useful in treating SUD.

17. The method of claim 16, wherein the candidate drug has a least one of: reduced or substantially no antibacterial activity, or reduced or substantially no antifungal activity, or both.

18. The method of claim 16, wherein the modification at least one of: produces steric hindrance, blocks hydrogen bonding, or charge coordination with divalent cations.

* * * * *